United States Patent
Chuang et al.

(10) Patent No.: US 10,167,258 B2
(45) Date of Patent: Jan. 1, 2019

(54) INHIBITORS OF MITOCHONDRIAL PYRUVATE DEHYDROGENASE KINASE ISOFORMS 1-4 AND USES THEREOF

(71) Applicant: The Board of Regents of the University of Texas System, Austin, TX (US)

(72) Inventors: David T. Chuang, Dallas, TX (US); Shih-Chia Tso, Carrolton, TX (US); Xiangbing Qi, Beijing (CN); Wen-Jun Gui, Dallas, TX (US); Cheng-Yang Wu, Dallas, TX (US); Jacinta L. Chuang, Dallas, TX (US); Uttam K. Tambar, Dallas, TX (US); R. Max Wynn, Hurst, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/103,619

(22) PCT Filed: Dec. 12, 2014

(86) PCT No.: PCT/US2014/069913
§ 371 (c)(1),
(2) Date: Jun. 10, 2016

(87) PCT Pub. No.: WO2015/089360
PCT Pub. Date: Jun. 18, 2015

(65) Prior Publication Data
US 2017/0001958 A1    Jan. 5, 2017

Related U.S. Application Data

(60) Provisional application No. 61/915,814, filed on Dec. 13, 2013.

(51) Int. Cl.
| | | |
|---|---|---|
| C07D 209/44 | (2006.01) | |
| C07D 401/14 | (2006.01) | |
| C07D 401/06 | (2006.01) | |
| C07D 401/12 | (2006.01) | |
| C07D 487/08 | (2006.01) | |

(52) U.S. Cl.
CPC ......... C07D 209/44 (2013.01); C07D 401/06 (2013.01); C07D 401/12 (2013.01); C07D 401/14 (2013.01); C07D 487/08 (2013.01)

(58) Field of Classification Search
CPC ............................ C07D 209/44; C07D 401/06
See application file for complete search history.

(56) References Cited

U.S. PATENT DOCUMENTS

2011/0201643 A1    8/2011  Maier et al.
2012/0108631 A1    5/2012  Becker et al.

FOREIGN PATENT DOCUMENTS

| WO | WO 1996-036611 | 11/1996 |
|---|---|---|
| WO | WO 2006-117669 | 11/2006 |
| WO | WO 2011-050210 | 4/2011 |

OTHER PUBLICATIONS

Montana, et al. Document No. 126:59877, retrieved from STN; Nov. 21, 1996.*
Bromidge, et al. Document No. 130:125095, retrieved from STN; Jan. 21, 1999.*
Schunk, et al. Document No. 153:311106, retrieved from STN; Aug. 12, 2010.*
Shultz, et al. Document No. 155:380086, retrieved from STN; 2011.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Aicher et al., "Secondary amides of (R)-3,3,3-trifluoro-2-hydroxy-2-methylpropionic acid as inhibitors of pyruvate dehydrogenase kinase," *J Medicinal Chemistry*, 43:236-249, 2000.
Bonnet et al., "A mitochondria-K+ channel axis is suppressed in cancer and its normalization promotes apoptosis and inhibits cancer growth," *Cancer Cell*, 11:37-51, 2007.
Dymock et al., "Novel, potent small-molecule inhibitors of the molecular chaperone Hsp90 discovered through structure-based design," *J Medicinal Chemistry*, 48:4212-4215, 2005.
Feldman et al., "Potent triazolothione inhibitor of heat-shock protein-90," *Chem Biol Drug Des.*, 74(1):43-50, 2009.
Ferriero et al., "Phenylbutyrate therapy for pyruvate dehydrogenase complex deficiency and lactic acidosis," *Science Translational Medicine*, 5(175):175ra31, 2013.
Fujiwara et al., "PDK1 inhibition is a novel therapeutic target in multiple myeloma," *British Journal of Cancer*, 108:170-178, 2013.
Hitosugi et al., "Tyrosine phosphorylation of mitochondrial pyruvate dehydrogenase kinase 1 is important for cancer metabolism," *Molecular Cell*, 44:864-877, 2011.
Iannitti et al., "Clinical and experimental applications of sodium phenylbutyrate," *Drugs in R&D*, 11:227-249, 2011.
Jeoung and Harris, "Pyruvate dehydrogenase kinase-4 deficiency lowers blood glucose and improves glucose tolerance in diet-induced obese mice.," *American Journal of Physiology. Endocrinology and Metabolism*, 295:E46-E54, 2008.

(Continued)

*Primary Examiner* — Shawquia Jackson
(74) *Attorney, Agent, or Firm* — Parker Highlander PLLC

(57) ABSTRACT

The present disclosure relates to the identification of PDK inhibitors and their use in the treatment of diseases such as diabetes, cardiovascular disease and cancer. The invention relates to the development of robust PDK inhibitors that can be used to improve glucose metabolism and correct metabolic dysfunction in vivo. Based on the unique structural features present in the ATP-binding pocket of PDK2, a single functional-group change was made in a known Hsp90 inhibitor that binds to the corresponding pocket of the latter protein from the GHKL family. This approach efficiently converted the Hsp90 inhibitor to a highly specific inhibitor for all PDK isoforms. These final PDK inhibitors of this series robustly augments PDC activity with reduced phosphorylation in tissues.

23 Claims, 14 Drawing Sheets

(56) References Cited

OTHER PUBLICATIONS

Jiang et al., "Genetic variants in STAT4 and HLA-DQ genes confer risk of hepatitis B virus-related hepatocellular carcinoma," *Nature Genetics*, 45:72-75, 2013.

Kaplon et al., "A key role for mitochondrial gatekeeper pyruvate dehydrogenase in oncogene-induced senescence," *Nature*, 498:109-112, 2013.

Kato et al., "Crystal structure of pyruvate dehydrogenase kinase 3 bound to lipoyl domain 2 of human pyruvate dehydrogenase complex," *Embo J*, 24:1763-1774, 2005.

Kato et al., "Distinct structural mechanisms for inhibition of pyruvate dehydrogenase kinase isoforms by AZD7545, dichloroacetate, and radicicol," *Structure*, 15:992-1004, 2007.

Kato et al., "Structural basis for inactivation of the human pyruvate dehydrogenase complex by phosphorylation: role of disordered phosphorylation loops," *Structure*, 16:1849-1859, 2008.

Kim et al., "HIF-1-mediated expression of pyruvate dehydrogenase kinase: a metabolic switch required for cellular adaptation to hypoxia," *Cell Metabolism*, 3:177-185, 2006.

Knoechel et al., "Regulatory roles of the N-terminal domain based on crystal structures of human pyruvate dehydrogenase kinase 2 containing physiological and synthetic ligands," *Biochemistry*, 45:402-415, 2006.

Korotchkina et al., "R-lipoic acid inhibits mammalian pyruvate dehydrogenase kinase," *Free Radical Res*, 38:1083-1092, 2004.

Kung et al.,"Dihydroxyphenylisoindoline amides as orally bioavailable inhibitors of the heat shock protein 90 (hsp90) molecular chaperone," *J Medicinal Chemistry*, 53:499-503, 2010.

Kuzuya et al. ,"Regulation of branched-chain amino acid catabolism in rat models for spontaneous type 2 diabetes mellitus," *Biochemical and Biophysical Research Communications*, 373:94-98, 2008.

Mayers et al.,"AZD7 545, a novel inhibitor of pyruvate dehydrogenase kinase 2 (PDHK2), activates pyruvate dehydrogenase in vivo and improves blood glucose control in obese (fa/fa) Zucker rats," *Biochemical Society Transactions*, 31: 1165-1167, 2003.

Meng et al., "Discovery and optimization of 4,5-diarylisoxazoles as potent dual inhibitors of pyruvate dehydrogenase kinase and heat shock protein 90," *Journal of Medicinal Chemistry*, 57(23):9832-9843, 2014.

Moore et al., "VER-246608, a novel pan-isoform ATP competitive inhibitor of pyruvate dehydrogenase kinase, disrupts Warburg metabolism and induces context-dependent cytostasis in cancer cells," *Oncotarget*, 5(24):12862-12876, 2014.

Murray et al., "Fragment-based drug discovery applied to Hsp90. Discovery of two lead series with high ligand efficiency," *J Medicinal Chemistry*, 53:5942-5955, 2010.

Papandreou et al., "HIF-1 mediates adaptation to hypoxia by actively downregulating mitochondrial oxygen consumption," *Cell Metabolism*, 3:187-197, 2006.

PCT International Preliminary Report on Patentability issued in International Application No. PCT/US2014/069913, dated Jun. 23, 2016.

PCT International Search Report and Written Opinion issued in International Application No. PCT/US2014/069913, dated May 18, 2015.

Piao et al., "FOXO1-mediated upregulation of pyruvate dehydrogenase kinase-4 (PDK4) decreases glucose oxidation and impairs right ventricular function in pulmonary hypertension: therapeutic benefits of dichloroacetate," *J Mol Med*, 91:333-346, 2013.

Rosa et al., "Reduced PDK4 expression associates with increased insulin sensitivity in postobese patients," *Obesity Research*, 11:176-182, 2003.

Stacpoole et al., "Metabolic effects of dichloroacetate in patients with diabetes mellitus and hyperlipoproteinemia," *The New England Journal of Medicine*, 298:526-530, 1978.

Stacpoole et al., "Treatment of congenital lactic acidosis with dichloroacetate ," *Arch Dis Child.*, 77(6):535-41, 1997.

Tso et al.. "Structure-guided development of specific pyruvate dehydrogenase kinase inhibitors. targeting the ATP-binding pocket," *J Biol Chem.*, 289(7):4432-4443, 2014.

Tuganova et al.,"Recognition of the inner lipoyl-bearing domain of dihydrolipoyl transacetylase and of the blood glucose-lowering compound AZD7545 by pyruvate dehydrogenase kinase 2," *Biochemistry*, 46: 8592-8602, 2007.

Wolff et al., "Metabolic approaches to the treatment of ischemic heart disease: the clinicians' perspective," *Heart Failure Reviews*, 7:187-203, 2002.

Wu et al., "Mechanism responsible for inactivation of skeletal muscle pyruvate dehydrogenase complex in starvation and diabetes," *Diabetes*, 48:1593-1599, 1999.

Wynn et al., "Pyruvate dehydrogenase kinase-4 structures reveal a metastable open conformation fostering robust core-free basal activity," *J Biol Chem.*, 283(37):25305-25315, 2008.

\* cited by examiner

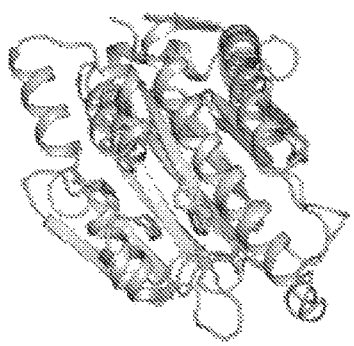
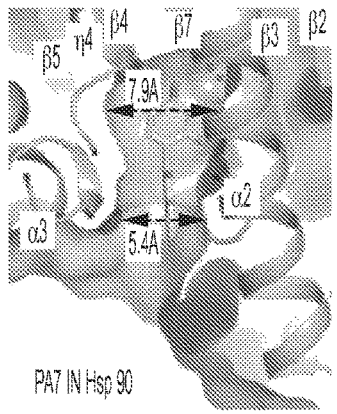
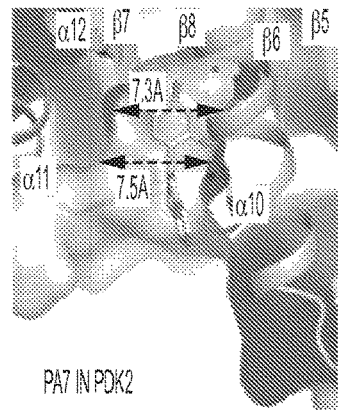
FIG. 2A  FIG. 2B  FIG. 2C
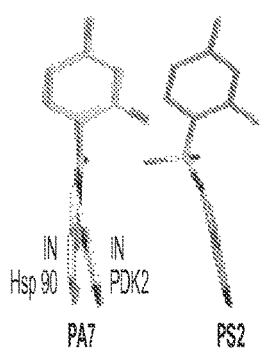
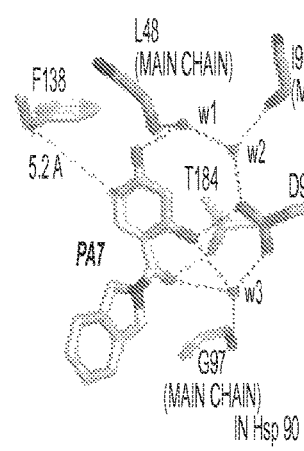
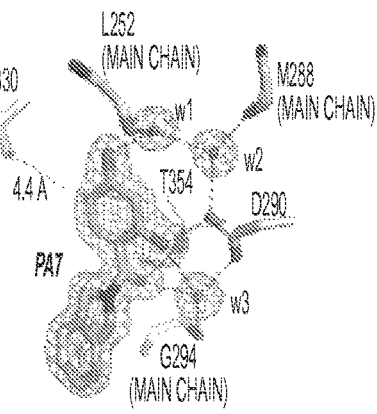
FIG. 2D  FIG. 2E  FIG. 2F
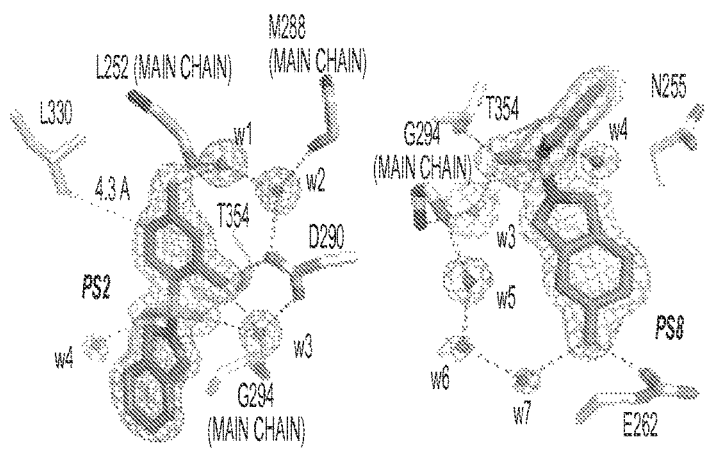
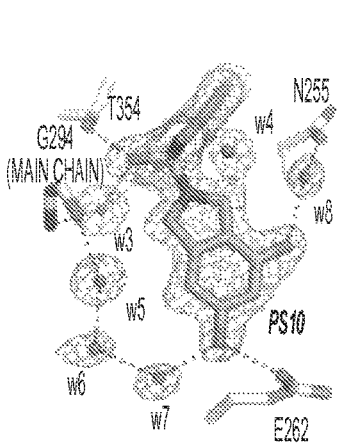
FIG. 2G  FIG. 2H  FIG. 2I

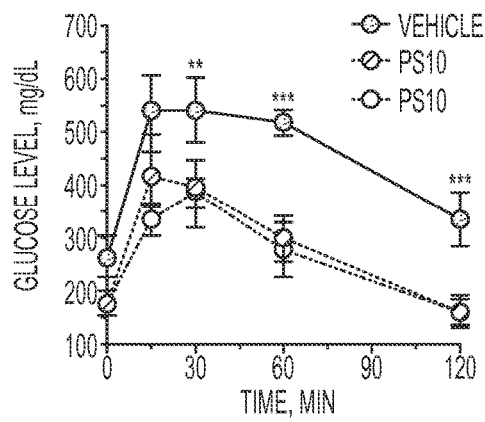
FIG. 9A
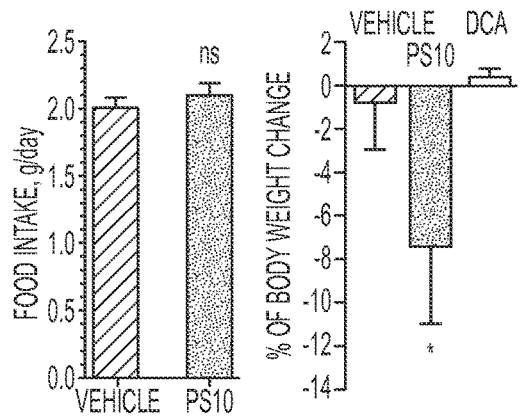
FIG. 9B    FIG. 9C
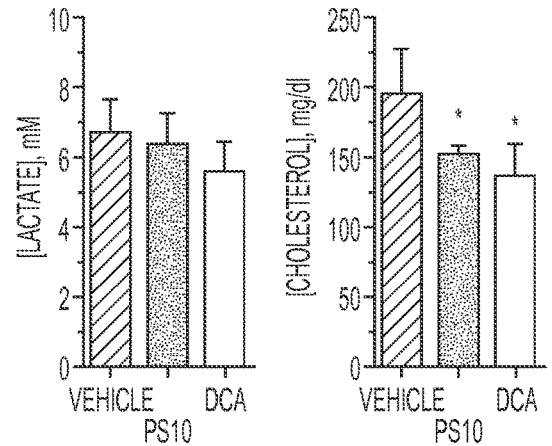
FIG. 9D    FIG. 9E
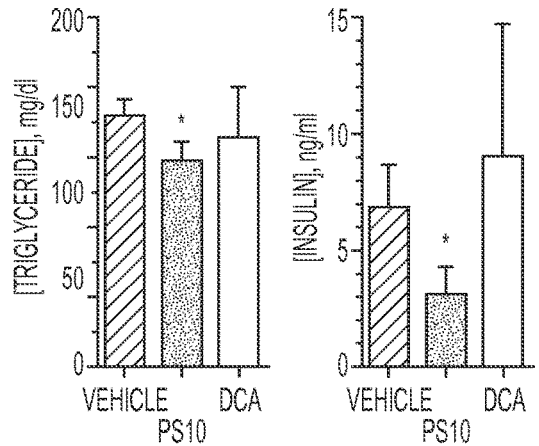
FIG. 9F    FIG. 9G
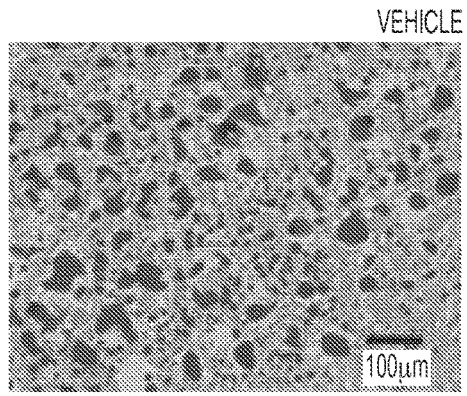
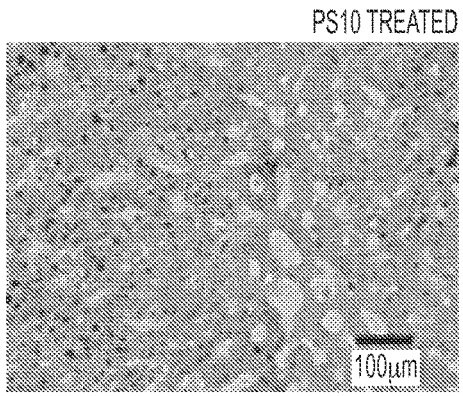
FIG. 9H

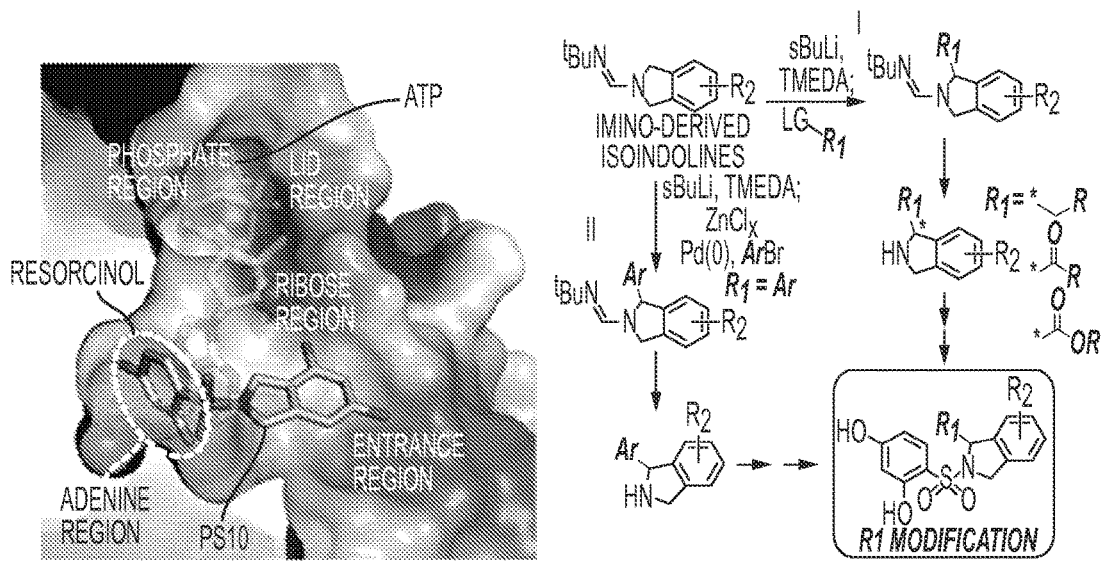
FIG. 15A  FIG. 15B
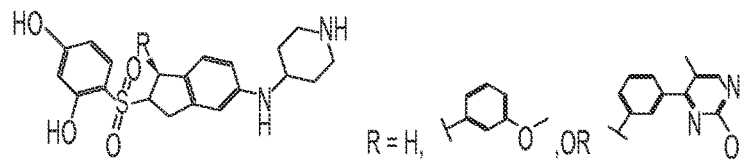
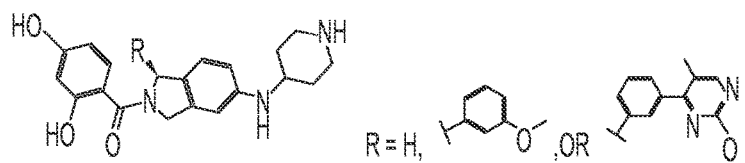
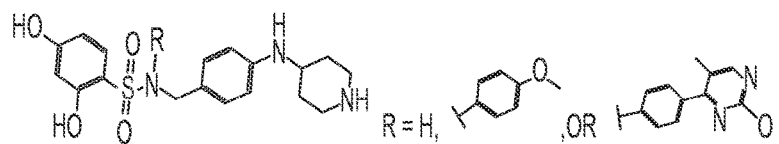
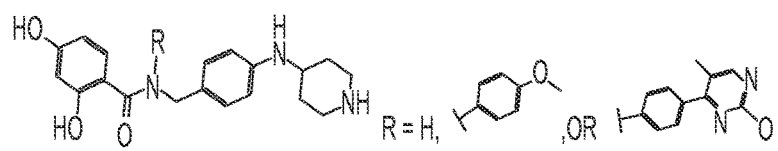
FIG. 16

INHIBITORS OF MITOCHONDRIAL PYRUVATE DEHYDROGENASE KINASE ISOFORMS 1-4 AND USES THEREOF

This application is a national phase application under 35 U.S.C. § 371 of International Application No. PCT/US2014/069913, filed Dec. 12, 2014, which claims benefit of priority to U.S. Provisional Application Ser. No. 61/915,814, filed Dec. 13, 2013, the entire contents of each of which are hereby incorporated by reference.

The invention was made with government support under grant 2R01DK062306 awarded by the National Institutes of Health. The government has certain rights in the invention.

BACKGROUND

1. Field of Endeavor

The present invention relates generally to the fields of cell biology, medicine and pathology. More particularly, it concerns methods and compositions relating to PDK inhibitors and their use to treat diseases ranging from diabetes to cardiovascular disease and cancer.

2. Description of Related Art

The mitochondrial pyruvate dehydrogenase complex (PDC) catalyzes the oxidative decarboxylation of pyruvate to give rise to acetyl-CoA, and is the gate-keeping enzyme linking glycolysis and the Krebs cycle. The mammalian PDC is a 9.5 million-dalton protein machine organized about a 60-meric core consisting of dihydrolipoyl transacetylase (E2) and the E3-binding protein (E3BP), to which multiple copies of pyruvate dehydrogenase (E1) and dihydrolipoyl transacetylase (E2), dihydrolipoamide dehydrogenase (E3), as well as isoforms of pyruvate dehydrogenase kinase (PDKs 1-4) and pyruvate dehydrogenase phosphatase (PDPs 1-2) are attached through ionic interactions (Reed 2001). Due to its strategic location, the regulation of PDC activity is critical for glucose homeostasis and fuel selection in the glucose-fatty acid cycle (Randle 1995). The mammalian PDC is acutely regulated by reversible phosphorylation (Harris et al., 1997). The phosphorylation of PDC by PDK results in inactivation; and dephosphorylation by PDP restores PDC activity. When glucose levels are low during fasting, PDC is highly phosphorylated and inactive, so as to preserve the substrates (pyruvate, lactate and alanine) for gluconeogenesis (Randle 1995).

The PDKs are potential therapeutic targets because of increased PDK expression in disease states such as diabetes, cancer and heart failure. PDK4, but not PDK2, is drastically induced in muscle and heart in streptozotocin-induced diabetes (Wu et al., 1999), obesity (Rosa et al., 2003) and type 2 diabetes (Kuzuya et al., 2008), which attenuates PDC activity leading to reduced glucose oxidation. The accumulated evidence has established that the upregulation of PDK4 is mediated through the PPARα-FOXO3α-PGC-1α complex (Wu et al., 1999). The PDK2/PDK4 double knockout mice fed a high-fat diet show marked improvements in glucose tolerance and insulin sensitivity over wild-type mice on the same diet (Jeoung et al., 2012). The expression of PDK1 (Papandreou et al., 2006; Kim et al., 2006 and Kaplon et al., 2013), PDK2 (Michelakis et al., 2010), and PDK3 (Lu et al., 2008) is significantly elevated in certain cancers. Tyrosine phosphorylation of PDK1 with increased kinase activity is essential for tumor cell proliferation and hypoxia (Hitosugi et al., 2011). Inhibition of PDK activity with dichloroacetate (DCA) or siRNA promotes apoptosis in cancer cells and impedes tumor growth (Bonnet et al., 2007).

The classic PDK inhibitor DCA, an analogue of the PDC substrate pyruvate, has been used since early 1970 to inhibit PDK activity and increase the PDC flux, with concomitant reduction in glucose levels in animals (Whitehouse and Randle 1973). DCA exerts its inhibitory effects by binding to an allosteric site in the N-terminal domain of PDK isoforms (Kato et al., 2007 and Knoechel et al., 2006). However, DCA is a non-specific low-potency PDK inhibitor and requires high doses for its therapeutic effects (Jiang et al., 2013), which leads to peripheral neurological toxicity and tumor growth (Stacpoole et al., 1997). R-lipoic acid in mM concentrations abates PDK activity in vitro (Korotchkina et al., 2004), but its function as a PDK inhibitor in vivo is uncertain. Phenylbutyrate enhances PDC activity in vitro and in vivo (Ferriero et al., 2013); but the compound is a modest PDK inhibitor (Ki=0.3 mM) with multiple targets and diverse clinical applications (Iannitti et al., 2011). Dihydrolipoamide mimetics including AZD7545 (Mayers et al., 2003) and secondary amides of SDZ048-619 (Aicher et al., 2000) have also been developed. This family of compounds inhibits PDK2 activity by impeding PDK binding to the E2/E3BP core of PDC (Kato et al., 2008). Paradoxically, these dihydrolipoamide mimetics strongly stimulates PDC core-free PDK4 activity in vitro, which precludes these compounds as bona fide PDK inhibitors (Wynn et al., 2008). To date, there have been no effective PDK inhibitors for novel therapeutic approaches to cancer, obesity and type 2 diabetes as well as heart disease.

Mitochondrial PDK isoforms are members of the GHKL ATPase/kinase superfamily that includes DNA gyrase B, heat-shock protein 90 (Hsp90), histidine kinases CheA and EnvZ as well as the DNA-repair enzyme MutL (Dutta and Inouye 2000). Members of this superfamily share four conserved motifs (N-, G1-, G2- and G3-boxes) that build a unique Bergerat ATP-binding fold consisting of a four-stranded mixed β-sheet and three α helices, and is located in the C-terminal domains of PDK isoforms (Steussy et al., 2001 and Kato et al., 2005). This signature fold also contains a unique structural element known as the "ATP lid", whose conformational change is coupled to ATP hydrolysis and protein-protein interactions (Kato et al., 2005).

SUMMARY

Thus, in accordance with the present invention, there is provided a compound of the formula:

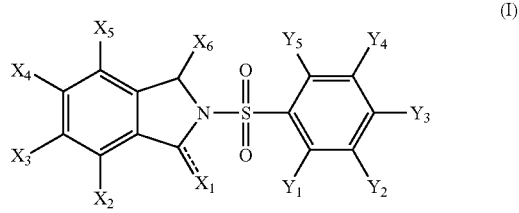

(I)

wherein:
$X_1$ is hydrogen, halogen, hydroxy, amino, cyano, nitro, or oxo, or alkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heterocycloalkyl$_{(C \leq 12)}$, heteroaryl$_{(C \leq 12)}$, acyl$_{(C \leq 12)}$, —C(O)-alkoxy$_{(C \leq 12)}$, alkoxy$_{(C \leq 12)}$, alkenyloxy$_{(C \leq 12)}$, alkynyloxy$_{(C \leq 12)}$, aryloxy$_{(C \leq 18)}$, aralkyloxy$_{(C \leq 18)}$, heterocycloalkyloxy$_{(C \leq 12)}$, heteroaryloxy$_{(C \leq 12)}$, acyloxy$_{(C \leq 12)}$, alkylamine$_{(C \leq 12)}$, dialkylamine$_{(C \leq 12)}$, alkenylamine$_{(C \leq 12)}$, alkynylamine$_{(C \leq 12)}$, arylamine$_{(C \leq 18)}$, aralkylamine$_{(C≤18)}$, heterocycloalkylamine$_{(C≤12)}$, heteroarylamine$_{(C≤12)}$, amido$_{(C≤12)}$, -arenediyl$_{(C≤6)}$-heteroaryl$_{(C≤12)}$, or a substituted version of any of these groups, or is taken together with X$_6$ as defined below;

X$_2$, X$_3$, X$_4$, X$_5$ are each independently hydrogen, halogen, hydroxy, nitro, cyano, or amino, or
alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylthio$_{(C≤12)}$, alkenylthio$_{(C≤12)}$, alkynylthio$_{(C≤12)}$, arylthio$_{(C≤18)}$, aralkylthio$_{(C≤18)}$, heterocycloalkylthio$_{(C≤12)}$, heteroarylthio$_{(C≤12)}$, acylthio$_{(C≤12)}$, alkylamine$_{(C≤12)}$, dialkylamine$_{(C≤12)}$, alkenylamine$_{(C≤12)}$, alkynylamine$_{(C≤12)}$, arylamine$_{(C≤18)}$, aralkylamine$_{(C≤18)}$, heterocycloalkylamine$_{(C≤12)}$, heteroarylamine$_{(C≤12)}$, amido$_{(C≤12)}$, -alkanediyl$_{(C≤6)}$-heterocycloalkyl$_{(C≤12)}$, or a substituted version of any of these groups; or

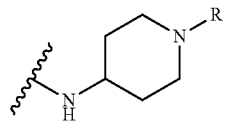

wherein: R is hydrogen; or alkyl$_{(C≤12)}$, alkenyl$_{(C≤12)}$, acyl$_{(C≤12)}$, aryl$_{(C≤12)}$, aralkyl$_{(C≤12)}$, or a substituted version of any of these groups;

X$_6$ is hydrogen, halogen, hydroxy, amino, nitro, or cyano, or
alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylamine$_{(C≤12)}$, dialkylamine$_{(C≤12)}$, alkenylamine$_{(C≤12)}$, alkynylamine$_{(C≤12)}$, arylamine$_{(C≤18)}$, aralkylamine$_{(C≤18)}$, heterocycloalkylamine$_{(C≤12)}$, heteroarylamine$_{(C≤12)}$, or amido$_{(C≤12)}$, or a substituted version of any of these groups, or when is taken together with X$_1$ as defined below;

Y$_1$, Y$_2$, Y$_3$, Y$_4$, and Y$_5$ are each independently hydrogen, amino, cyano, halo, hydroxy, or nitro, or
alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, or a substituted version of any of these groups;

X$_1$ and X$_6$ when taken together have the formula:

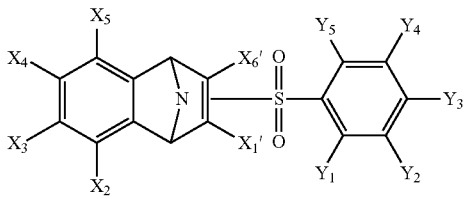

(II)

wherein:
X$_1$' and X$_6$' are each independently hydrogen, hydroxy, halo, or amino;
alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, acyl$_{(C≤12)}$, or a substituted version of any of these groups;
provided that at least one of Y$_1$, Y$_2$, Y$_3$, Y$_4$, or Y$_5$ are hydroxy or alkoxy$_{(C≤12)}$ and that X$_2$, X$_3$, X$_4$, and X$_5$ are not all hydrogen, or that when X$_1$ is oxo then X$_6$ is not aryl$_{(C≤8)}$;
or a pharmaceutically acceptable salt thereof.

The compound may be further defined by the formula:

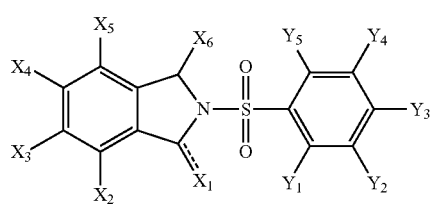

(I)

wherein:
X$_1$ is hydrogen, hydroxy, amino, or oxo, or
alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, —C(O)-alkoxy$_{(C≤12)}$, alkoxy$_{(C≤12)}$, alkylamine$_{(C≤12)}$, dialkylamine$_{(C≤12)}$, -arenediyl$_{(C≤6)}$-heteroaryl$_{(C≤12)}$, or a substituted version of any of these groups, or is taken together with X$_6$ as defined below;

X$_2$, X$_3$, X$_4$, X$_5$ are each independently hydrogen, hydroxy, or amino, or alkyl$_{(C≤12)}$, alkoxy$_{(C≤12)}$, heterocycloalkoxy$_{(C≤12)}$, alkylthio$_{(C≤12)}$, heterocycloalkylthio$_{(C≤12)}$, alkylamine$_{(C≤12)}$, dialkylamine$_{(C≤12)}$, heterocycloalkylamine$_{(C≤12)}$, -alkanediyl$_{(C≤6)}$-heterocycloalkyl$_{(C≤12)}$, or a substituted version of any of these groups; or

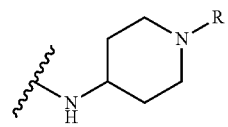

wherein: R is hydrogen; or alkyl$_{(C≤12)}$, alkenyl$_{(C≤12)}$, acyl$_{(C≤12)}$, aryl$_{(C≤12)}$, aralkyl$_{(C≤12)}$, or a substituted version of any of these groups;

X$_6$ is hydrogen, hydroxy, amino, or
alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylamine$_{(C≤12)}$, dialkylamine$_{(C≤12)}$, alkenylamine$_{(C≤12)}$, alkynylamine$_{(C≤12)}$, arylamine$_{(C≤18)}$, aralkylamine$_{(C≤18)}$, heterocycloalkylamine$_{(C≤12)}$, heteroarylamine$_{(C≤12)}$, or amido$_{(C≤12)}$, or a substituted version of any of these groups, or is taken together with X$_1$ as defined below;

Y$_1$, Y$_2$, Y$_3$, Y$_4$, and Y$_5$ are each independently hydrogen, amino, cyano, halo, hydroxy, or nitro, or
alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, or a substituted version of any of these groups;

X$_1$ and X$_6$ when taken together have the formula:

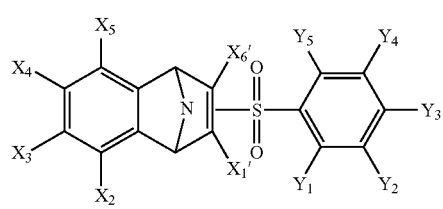

(II)

wherein:

$X_1'$ and $X_6'$ are each independently hydrogen, hydroxy, halo, or amino;

alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, acyl$_{(C \leq 12)}$, or a substituted version of any of these groups;

provided that at least one of $Y_1$, $Y_2$, $Y_3$, $Y_4$, or $Y_5$ are hydroxy or alkoxy$_{(C \leq 12)}$ and that $X_2$, $X_3$, $X_4$, and $X_5$ are not all hydrogen, or that when $X_1$ is oxo then $X_6$ is not aryl$_{(C \leq 8)}$;

or a pharmaceutically acceptable salt thereof.

$X_1$ may be hydrogen. Alternatively, $X_1$ may be oxo. $X_2$ and $X_5$ may each independently be hydrogen. $X_2$ and $X_5$ nat each independently be hydroxy or alkoxy$_{(C \leq 12)}$. $X_2$ and $X_5$ may each independently be methoxy. $X_3$ and $X_4$ may each independently be hydrogen. $X_3$ and $X_4$ may each independently be hydroxy or alkoxy$_{(C \leq 12)}$. $X_3$ and $X_4$ may each independently be methoxy. $X_3$ and $X_4$ may each independently be amino, alkylamino$_{(C \leq 12)}$, heterocycloalkylamino$_{(C \leq 12)}$, substituted alkylamino$_{(C \leq 12)}$, or substituted heterocycloalkylamino$_{(C \leq 12)}$. $X_3$ and $X_4$ may each independently be amino, cyclohexylamine,

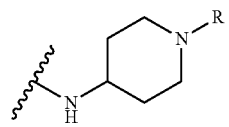

wherein: R is hydrogen; or alkyl$_{(C \leq 12)}$, alkenyl$_{(C \leq 12)}$, acyl$_{(C \leq 12)}$, aryl$_{(C \leq 12)}$, aralkyl$_{(C \leq 12)}$, or a substituted version of any of these groups. $X_6$ may be hydrogen. Alternatively, $X_6$ may be alkyl$_{(C \leq 12)}$, alkenyl$_{(C \leq 12)}$, aryl$_{(C \leq 12)}$, or a substituted version of any of these groups.

$Y_1$, $Y_2$, $Y_3$, $Y_4$, and $Y_5$ may each independently be hydrogen. $Y_1$, $Y_2$, $Y_3$, $Y_4$, and $Y_5$ may each independently be halo, hydroxy, or alkoxy$_{(C \leq 12)}$. $Y_1$, $Y_2$, $Y_3$, $Y_4$, and $Y_5$ may each independently be hydroxy. $Y_1$, $Y_2$, $Y_3$, $Y_4$, and $Y_5$ may each independently be methoxy. $Y_1$ and $Y_3$ may both be hydroxy or methoxy.

The compound may be further defined as:

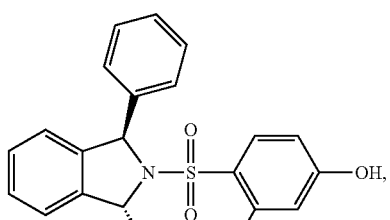

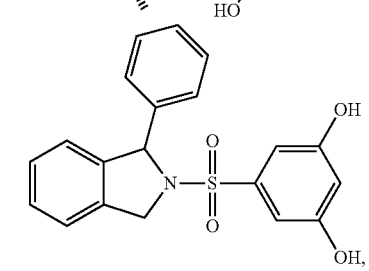

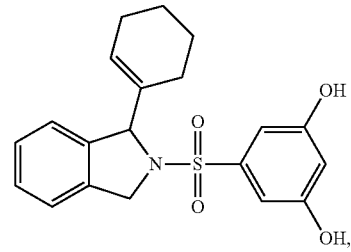

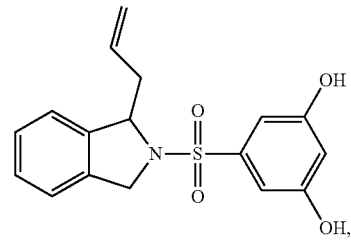

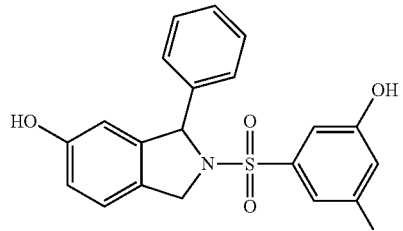

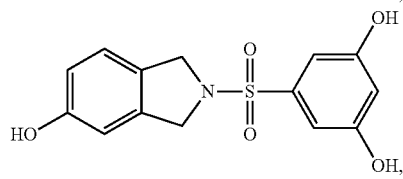

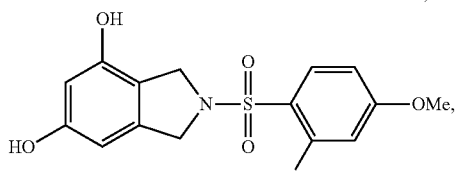

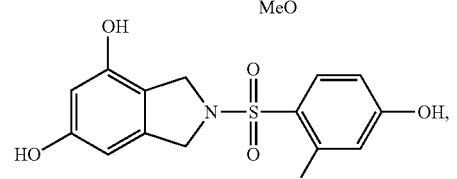

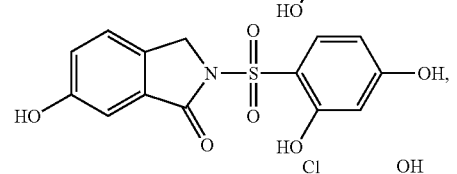

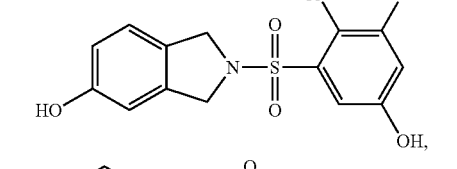

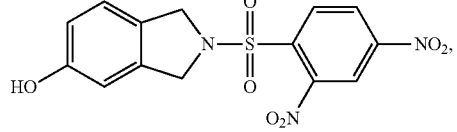

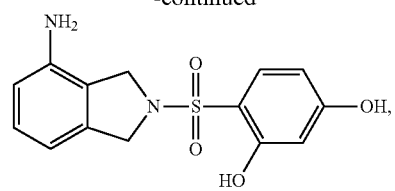
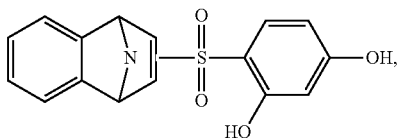
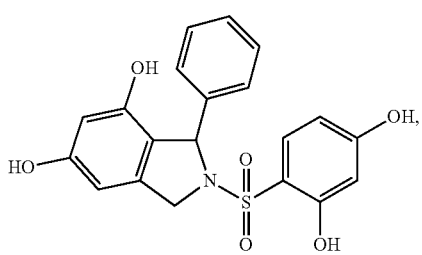
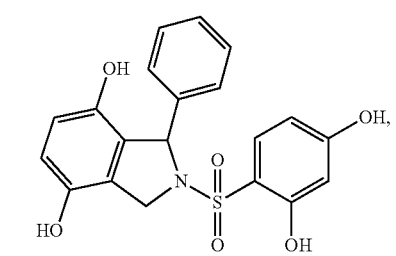
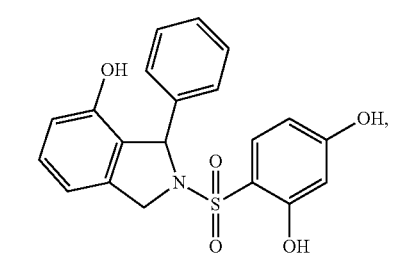
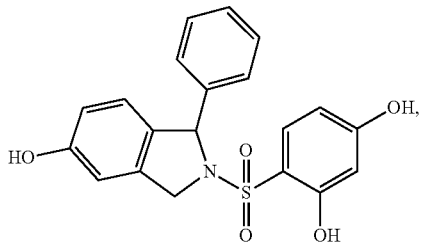
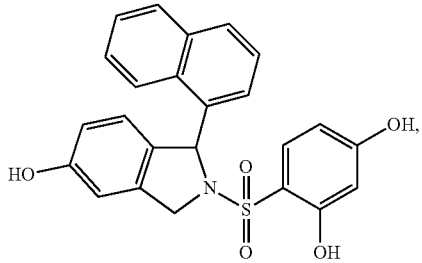
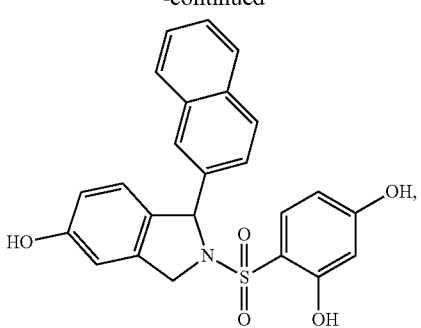
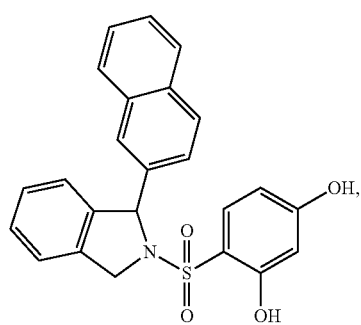
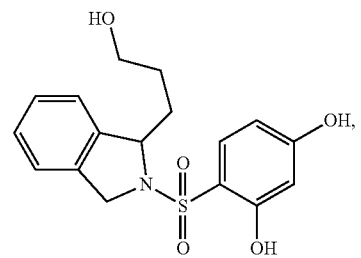
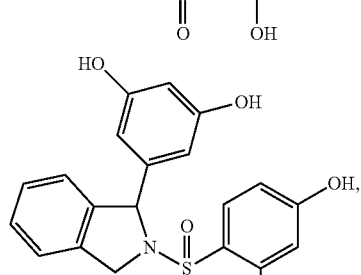
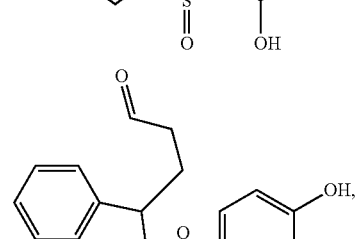
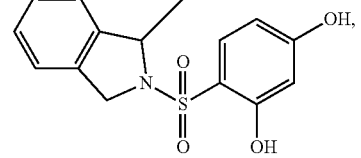

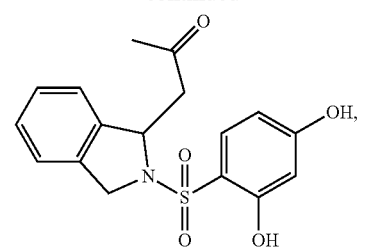
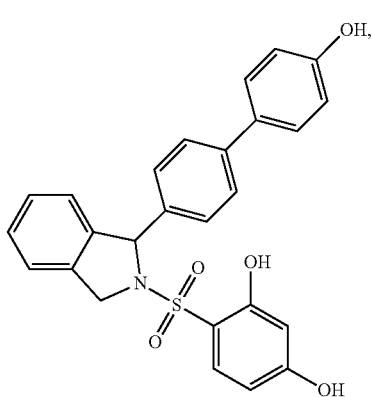
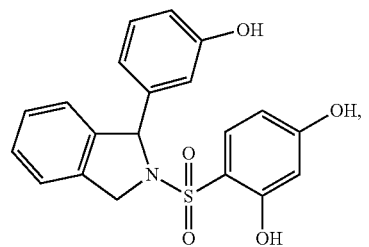
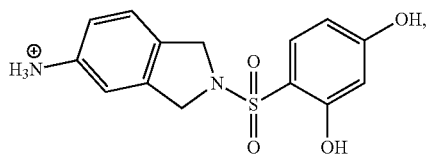
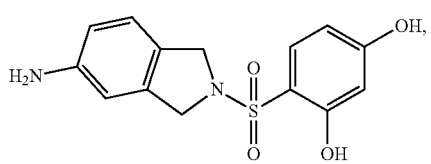
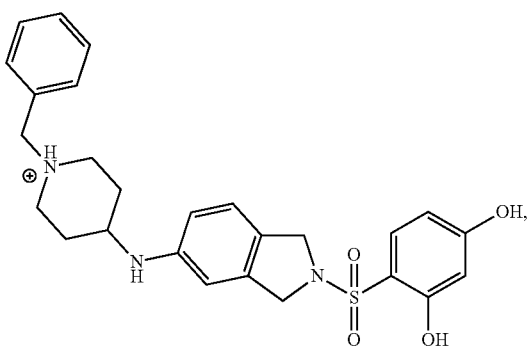
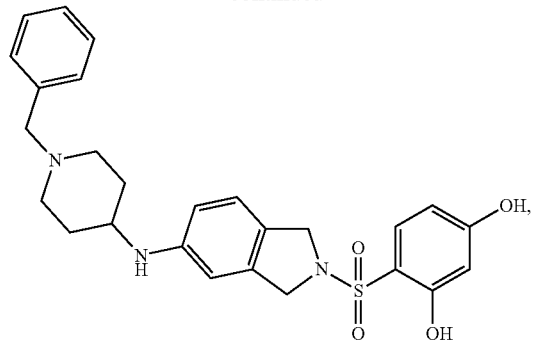
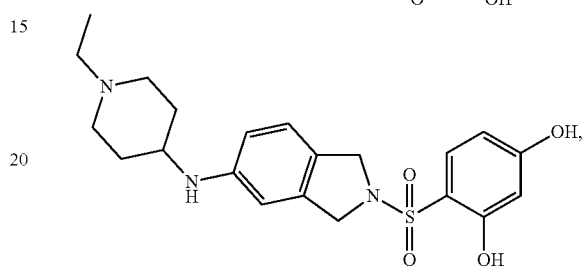
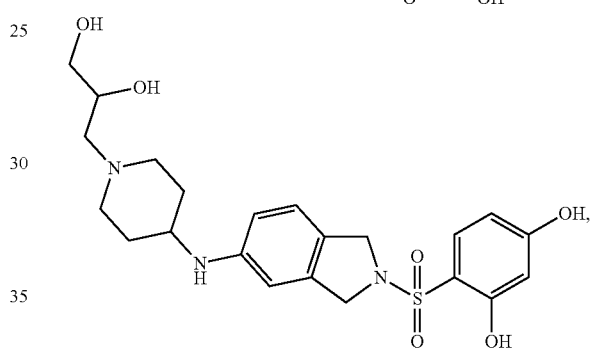
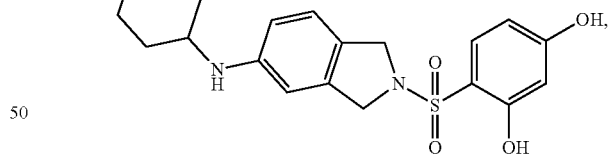
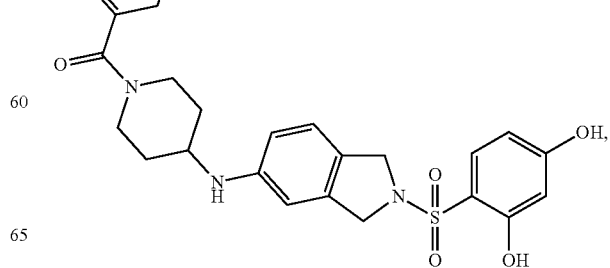

-continued
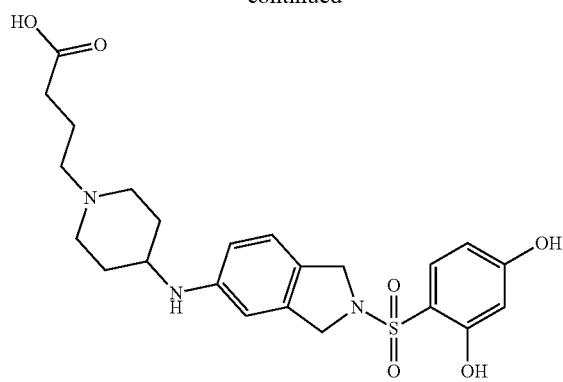
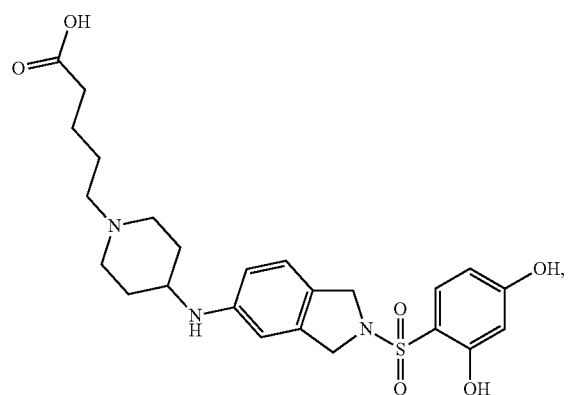
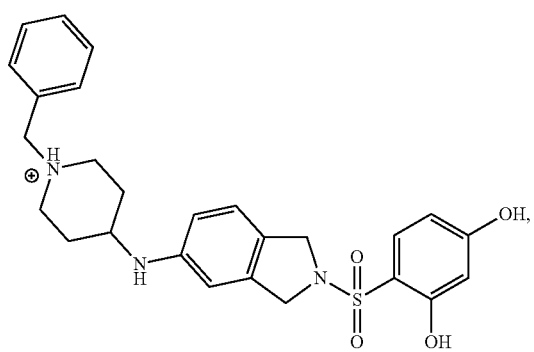
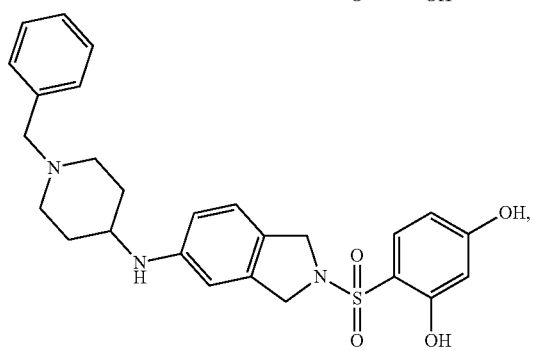
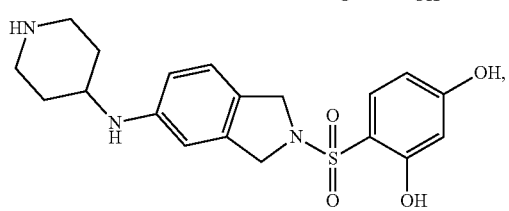
-continued
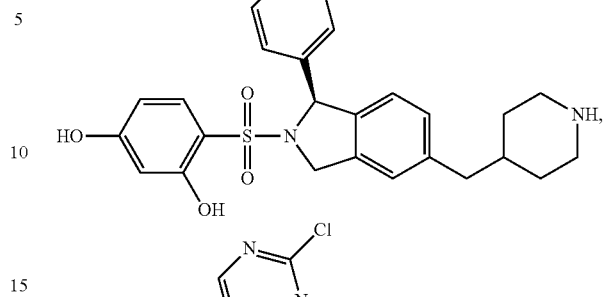
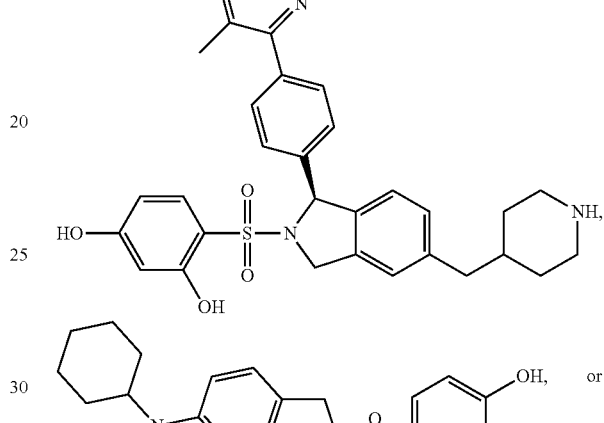
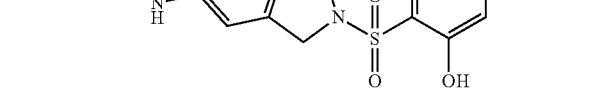
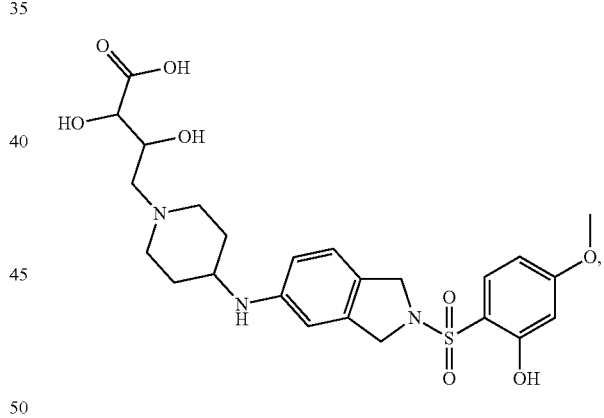
or a pharmaceutically acceptable salt, thereof.
Also provided is a method for inhibiting the activity of a pyruvate dehydrogenase kinase comprising administering a compound of the formula:
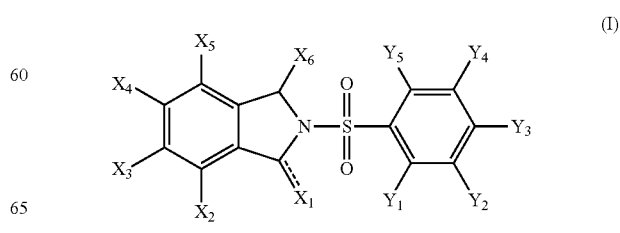
(I)

wherein:

$X_1$ is hydrogen, halogen, hydroxy, amino, cyano, nitro, or oxo, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, —C(O)-alkoxy$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, amido$_{(C\leq12)}$, -arenediyl$_{(C\leq6)}$-heteroaryl$_{(C\leq12)}$, or a substituted version of any of these groups, or taken together with $X_6$ as defined below;

$X_2$, $X_3$, $X_4$, $X_5$ are each independently hydrogen, halogen, hydroxy, nitro, cyano, or amino, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylthio$_{(C\leq12)}$, alkenylthio$_{(C\leq12)}$, alkynylthio$_{(C\leq12)}$, arylthio$_{(C\leq18)}$, aralkylthio$_{(C\leq18)}$, heterocycloalkylthio$_{(C\leq12)}$, heteroarylthio$_{(C\leq12)}$, acylthio$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, amido$_{(C\leq12)}$, or a substituted version of any of these groups;

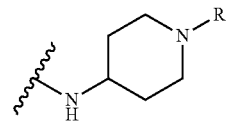

wherein: R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups;

$X_6$ is hydrogen, halogen, hydroxy, amino, nitro, or cyano, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, or amido$_{(C\leq12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, or a substituted version of any of these groups;

$X_1$ and $X_6$ when taken together have the formula:

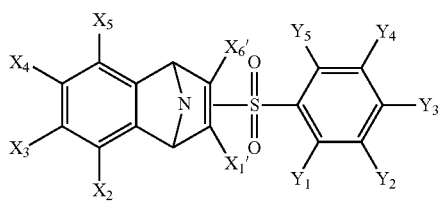

wherein:

$X_1'$ and $X_6'$ are each independently hydrogen, hydroxy, halo, or amino;

alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, acyl$_{(C\leq12)}$, or a substituted version of any of these groups;

or a pharmaceutically acceptable salt thereof.

The method may include a compound further defined as:

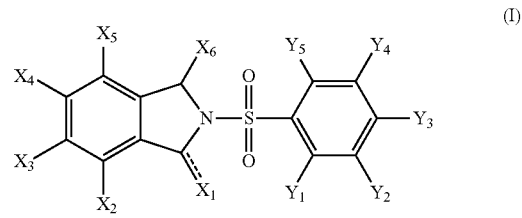

(I)

wherein:

$X_1$ is hydrogen, hydroxy, amino, or oxo, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, —C(O)-alkoxy$_{(C\leq12)}$, alkoxy$_{(C\leq12)}$, alkylamine$_{(C\leq12)}$, dialkylamine$_{(C\leq12)}$, -arenediyl$_{(C\leq6)}$-heteroaryl$_{(C\leq12)}$, or a substituted version of any of these groups, or is taken together with $X_6$ as defined below;

$X_2$, $X_3$, $X_4$, $X_5$ are each independently hydrogen, hydroxy, or amino, or alkyl$_{(C\leq12)}$, alkoxy$_{(C\leq12)}$, heterocycloalkoxy$_{(C\leq12)}$, alkylthio$_{(C\leq12)}$, heterocycloalkylthio$_{(C\leq12)}$, alkylamine$_{(C\leq12)}$, dialkylamine$_{(C\leq12)}$, heterocycloalkylamine$_{(C\leq12)}$, -alkanediyl$_{(C\leq6)}$-heterocycloalkyl$_{(C\leq12)}$, or a substituted version of any of these groups; or

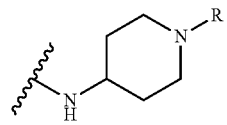

wherein: R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups;

$X_6$ is hydrogen, hydroxy, amino, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, or amido$_{(C\leq12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, or a substituted version of any of these groups;

$X_1$ and $X_6$ when taken together have the formula:

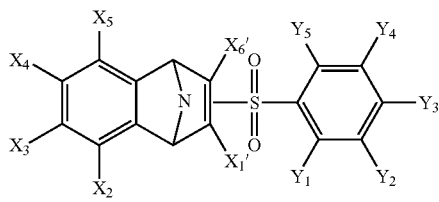

(II)

wherein:
$X_1'$ and $X_6'$ are each independently hydrogen, hydroxy, halo, or amino;
alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, acyl$_{(C\leq 12)}$, or a substituted version of any of these groups;
provided that at least one of $Y_1$, $Y_2$, $Y_3$, $Y_4$, or $Y_5$ are hydroxy or alkoxy$_{(C\leq 12)}$ and that $X_2$, $X_3$, $X_4$, and $X_5$ are not all hydrogen, or that when $X_1$ is oxo then $X_6$ is not aryl$_{(C\leq 8)}$;
or a pharmaceutically acceptable salt thereof.

$X_1$ may be hydrogen. Alternatively, $X_1$ may be oxo. $X_2$ and $X_5$ may each independently be hydrogen. $X_2$ and $X_5$ nat each independently be hydroxy or alkoxy$_{(C\leq 12)}$. $X_2$ and $X_5$ may each independently be methoxy. $X_3$ and $X_4$ may each independently be hydrogen. $X_3$ and $X_4$ may each independently be hydroxy or alkoxy$_{(C\leq 12)}$. $X_3$ and $X_4$ may each independently be methoxy. $X_3$ and $X_4$ may each independently be amino, alkylamino$_{(C\leq 12)}$, heterocycloalkylamino$_{(C\leq 12)}$, substituted alkylamino$_{(C\leq 12)}$, or substituted heterocycloalkylamino$_{(C\leq 12)}$. $X_3$ and $X_4$ may each independently be amino, cyclohexylamine, or

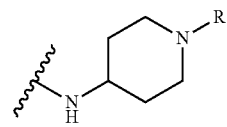

wherein: R is hydrogen; or alkyl$_{(C\leq 12)}$, alkenyl$_{(C\leq 12)}$, acyl$_{(C\leq 12)}$, aryl$_{(C\leq 12)}$, aralkyl$_{(C\leq 12)}$, or a substituted version of any of these groups.

$X_6$ may be hydrogen. Alternatively, $X_6$ may be alkyl$_{(C\leq 12)}$, alkenyl$_{(C\leq 12)}$, aryl$_{(C\leq 12)}$, or a substituted version of any of these groups.

$Y_1$, $Y_2$, $Y_3$, $Y_4$, and $Y_5$ may each independently be hydrogen. $Y_1$, $Y_2$, $Y_3$, $Y_4$, and $Y_5$ may each independently be halo, hydroxy, or alkoxy$_{(C\leq 12)}$. $Y_1$, $Y_2$, $Y_3$, $Y_4$, and $Y_5$ may each independently be hydroxy. $Y_1$, $Y_2$, $Y_3$, $Y_4$, and $Y_5$ may each independently be methoxy. $Y_1$ and $Y_3$ may both be hydroxy or methoxy.

The method may include a compound further defined as:

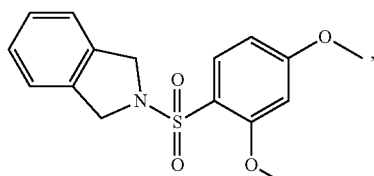

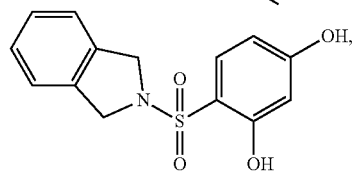

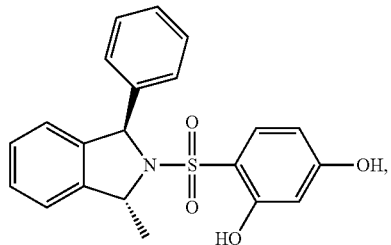

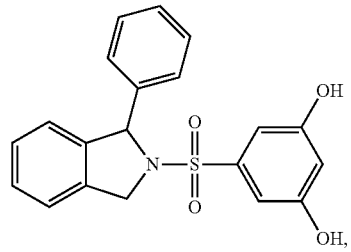

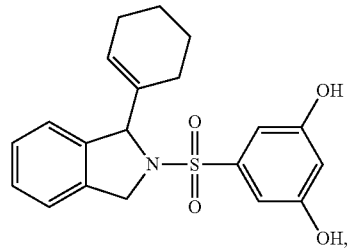

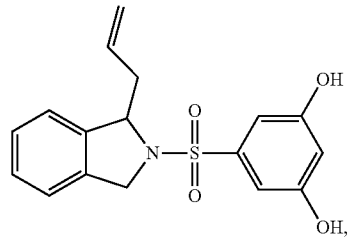

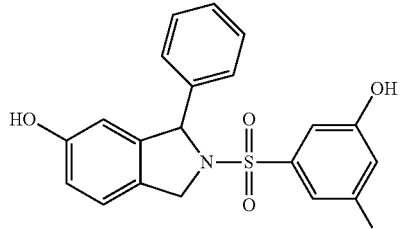

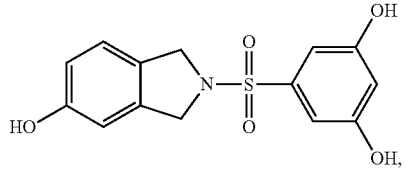

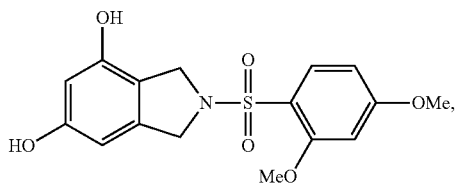

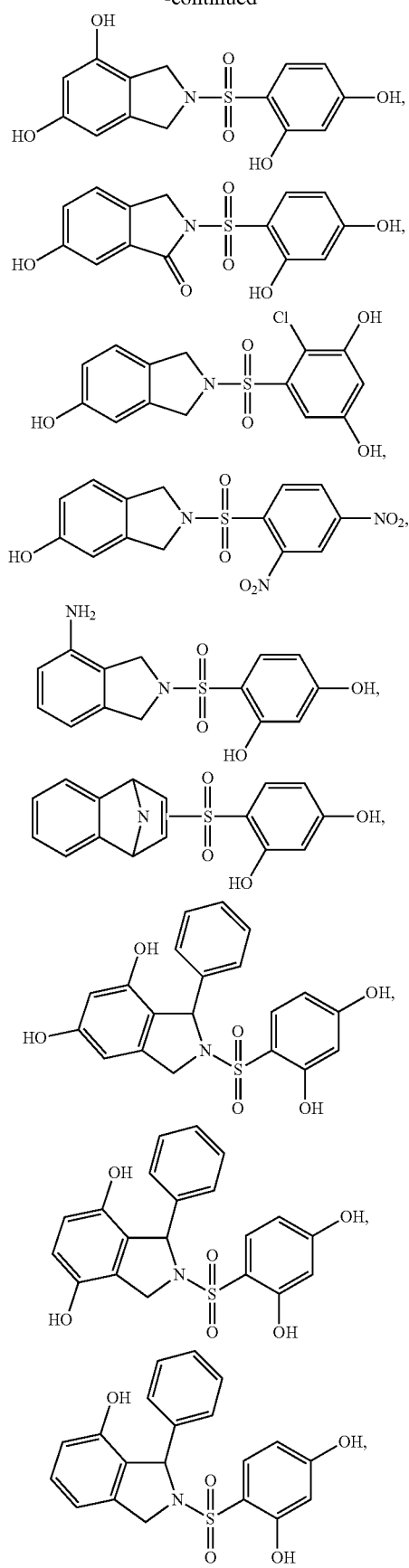
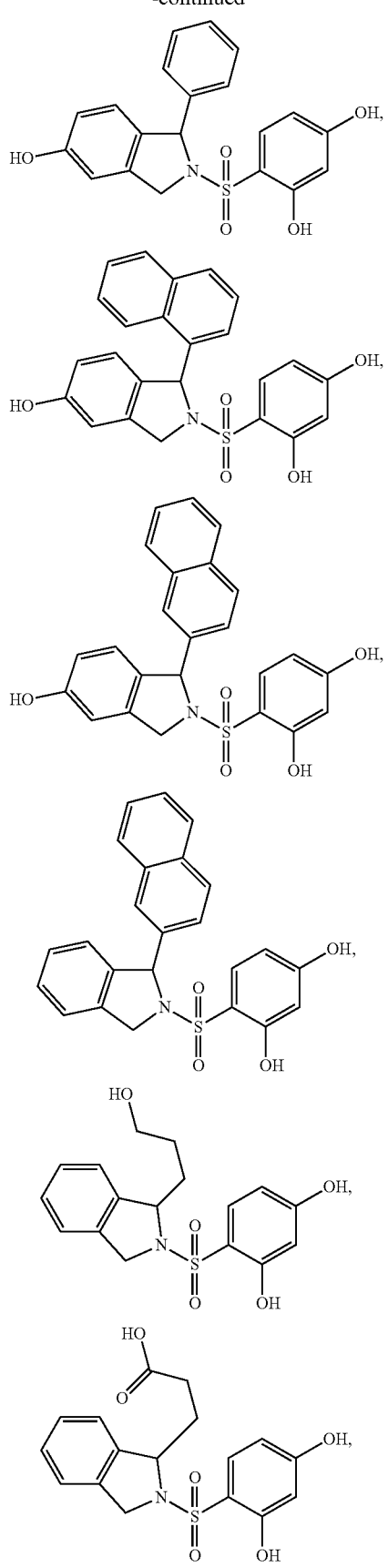

-continued
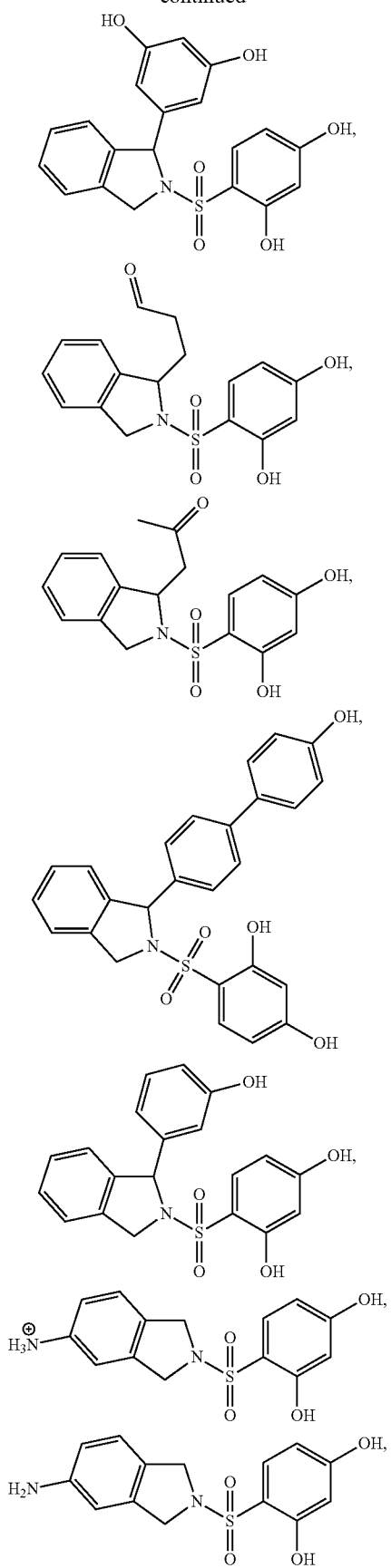
-continued
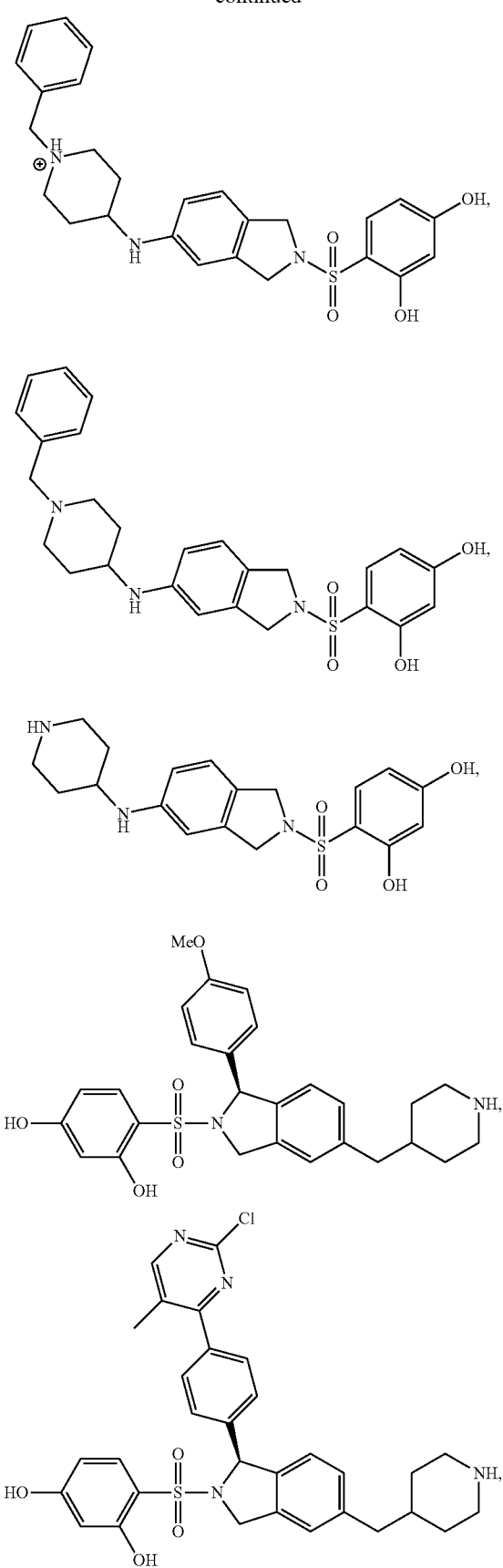

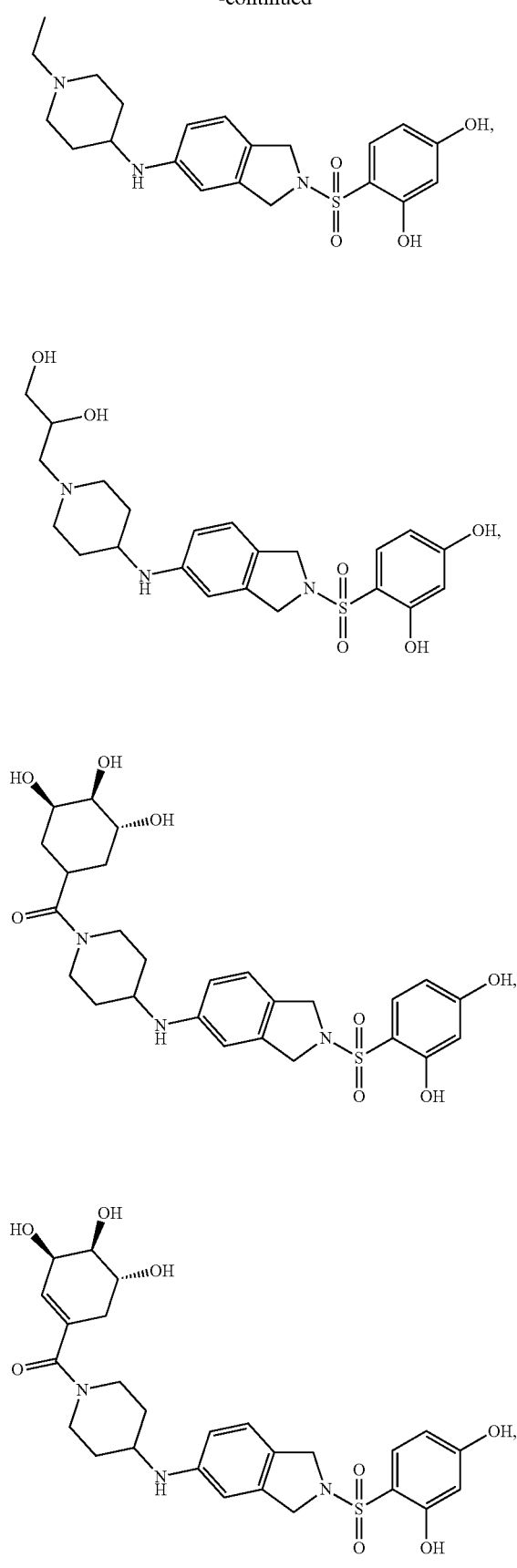
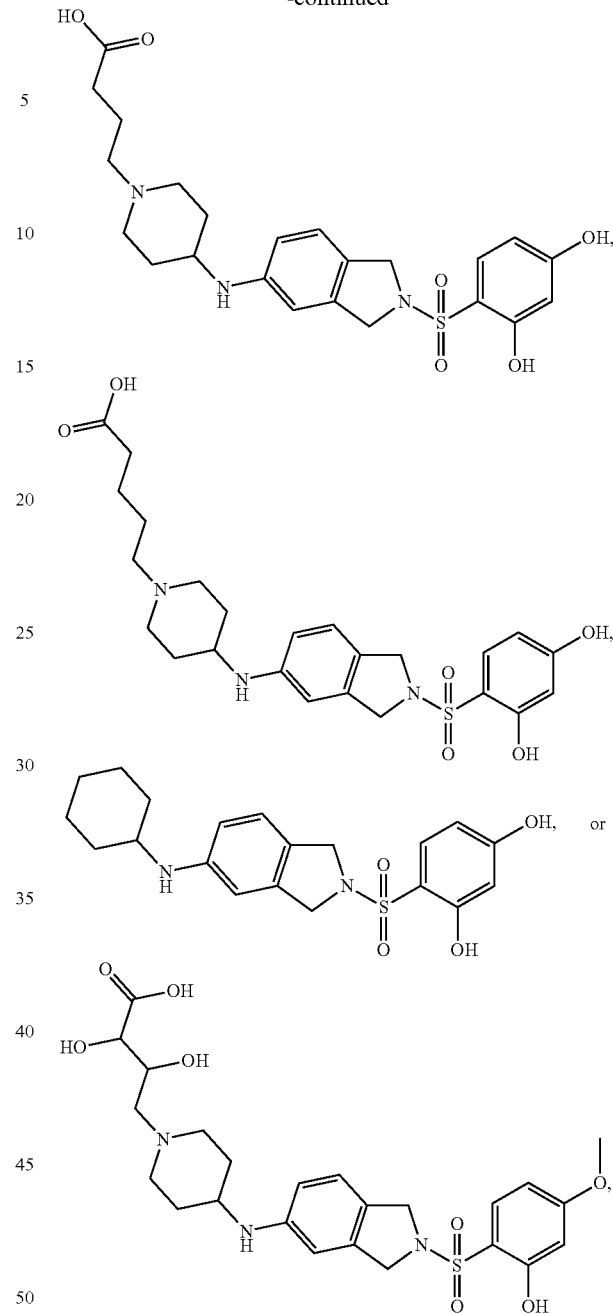
or a pharmaceutically acceptable salt, thereof.
In still another embodiment, there is provided a method for treating diabetes or a complication associated with diabetes in a subject comprising administering to the subject a therapeutically effective amount of a compound of the formula:
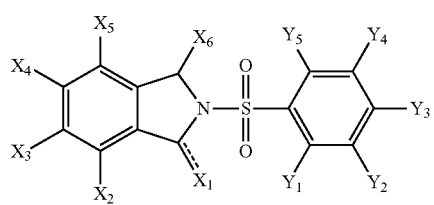
(I)

wherein:

$X_1$ is hydrogen, halogen, hydroxy, amino, cyano, nitro, or oxo, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, —C(O)-alkoxy$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, amido$_{(C\leq12)}$, -arenediyl$_{(C\leq6)}$-heteroaryl$_{(C\leq12)}$, or a substituted version of any of these groups, or is taken together with $X_6$ as defined below;

$X_2$, $X_3$, $X_4$, $X_5$ are each independently hydrogen, hydroxy, nitro, cyano, or amino, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylthio$_{(C\leq12)}$, alkenylthio$_{(C\leq12)}$, alkynylthio$_{(C\leq12)}$, arylthio$_{(C\leq18)}$, aralkylthio$_{(C\leq18)}$, heterocycloalkylthio$_{(C\leq12)}$, heteroarylthio$_{(C\leq12)}$, acylthio$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, amido$_{(C\leq12)}$, -alkanediyl$_{(C\leq6)}$-heterocycloalkyl$_{(C\leq12)}$, or a substituted version of any of these groups; or

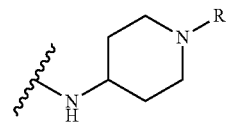

wherein: R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups;

$X_6$ is hydrogen, halogen, hydroxy, amino, nitro, or cyano, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, or amido$_{(C\leq12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, or a substituted version of any of these groups;

$X_1$ and $X_6$ when taken together have the formula:

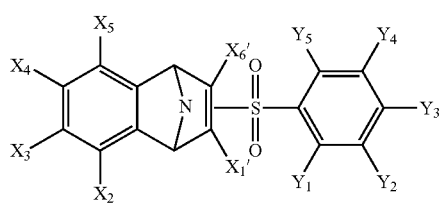

wherein:

$X_1'$ and $X_6'$ are each independently hydrogen, hydroxy, halo, or amino;

alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, acyl$_{(C\leq12)}$, or a substituted version of any of these groups;

provided that when $X_1$ is oxo, then $X_6$ is not aryl$_{(C\leq8)}$;

or a pharmaceutically acceptable salt thereof.

The method may include a compound further defined as:

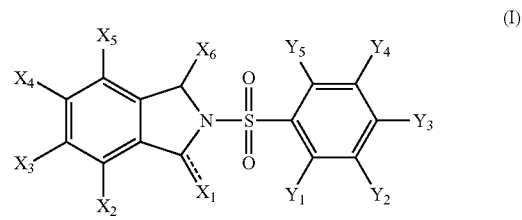

wherein:

$X_1$ is hydrogen, hydroxy, amino, or oxo, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, —C(O)-alkoxy$_{(C\leq12)}$, alkoxy$_{(C\leq12)}$, alkylamine$_{(C\leq12)}$, dialkylamine$_{(C\leq12)}$, -arenediyl$_{(C\leq6)}$-heteroaryl$_{(C\leq12)}$, or a substituted version of any of these groups, or is taken together with $X_6$ as defined below;

$X_2$, $X_3$, $X_4$, $X_5$ are each independently hydrogen, hydroxy, or amino, or alkyl$_{(C\leq12)}$, alkoxy$_{(C\leq12)}$, heterocycloalkoxy$_{(C\leq12)}$, alkylthio$_{(C\leq12)}$, heterocycloalkylthio$_{(C\leq12)}$, alkylamine$_{(C\leq12)}$, dialkylamine$_{(C\leq12)}$, heterocycloalkylamine$_{(C\leq12)}$, -alkanediyl$_{(C\leq6)}$-heterocycloalkyl$_{(C\leq12)}$; or a substituted version of any of these groups; or

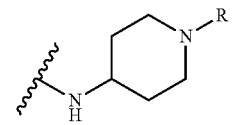

wherein: R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups;

$X_6$ is hydrogen, hydroxy, amino, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, or amido$_{(C\leq12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$; heterocycloalkyl$_{(C\leq12)}$, acyl$_{(C\leq12)}$, or a substituted version of any of these groups;

$X_1$ and $X_6$ when taken together have the formula:

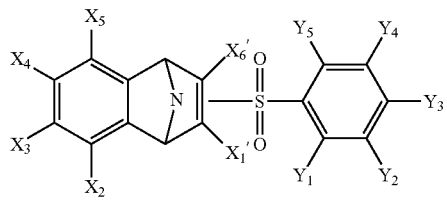

(II)

wherein:

$X_1{'}$ and $X_6{'}$ are each independently hydrogen, hydroxy, halo, or amino;

alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, acyl$_{(C≤12)}$, or a substituted version of any of these groups;

provided that when $X_1$ is oxo, then $X_6$ is not aryl$_{(C≤8)}$;

or a pharmaceutically acceptable salt thereof.

$X_1$ may be hydrogen. Alternatively, $X_1$ may be oxo. $X_2$ and $X_5$ may each independently be hydrogen. $X_2$ and $X_5$ nat each independently be hydroxy or alkoxy$_{(C≤12)}$. $X_2$ and $X_5$ may each independently be methoxy. $X_3$ and $X_4$ may each independently be hydrogen. $X_3$ and $X_4$ may each independently be hydroxy or alkoxy$_{(C≤12)}$. $X_3$ and $X_4$ may each independently be methoxy. $X_3$ and $X_4$ may each independently be amino, alkylamino$_{(C≤12)}$, heterocycloalkylamino$_{(C≤12)}$, substituted alkylamino$_{(C≤12)}$, or substituted heterocycloalkylamino$_{(C≤12)}$. $X_3$ and $X_4$ may each independently be amino, cyclohexylamine, or

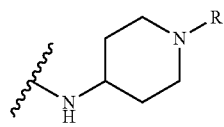

wherein: R is hydrogen; or alkyl$_{(C≤12)}$, alkenyl$_{(C≤12)}$, acyl$_{(C≤12)}$, aryl$_{(C≤12)}$, aralkyl$_{(C≤12)}$, or a substituted version of any of these groups.

$X_6$ may be hydrogen. Alternatively, $X_6$ may be alkyl$_{(C≤12)}$, alkenyl$_{(C≤12)}$, aryl$_{(C≤12)}$, or a substituted version of any of these groups.

$Y_1$, $Y_2$, $Y_3$, $Y_4$, and $Y_5$ may each independently be hydrogen. $Y_1$, $Y_2$, $Y_3$, $Y_4$, and $Y_5$ may each independently be halo, hydroxy, or alkoxy$_{(C≤12)}$. $Y_1$, $Y_2$, $Y_3$, $Y_4$, and $Y_5$ may each independently be hydroxy. $Y_1$, $Y_2$, $Y_3$, $Y_4$, and $Y_5$ may each independently be methoxy. $Y_1$ and $Y_3$ may both be hydroxy or methoxy.

The method may include a compound further defined as:

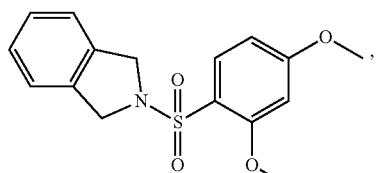

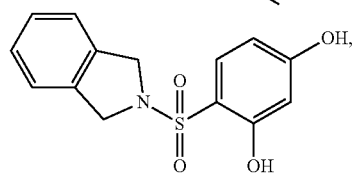

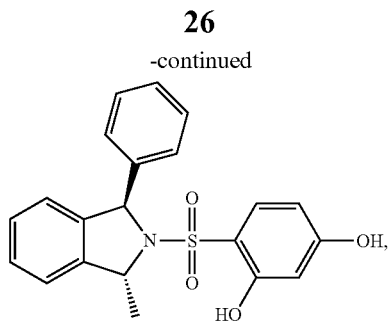

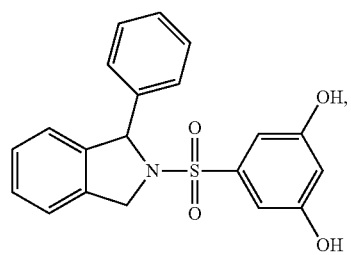

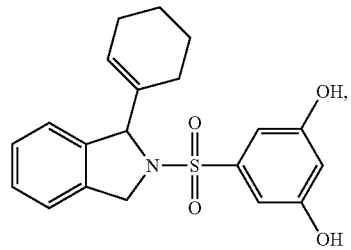

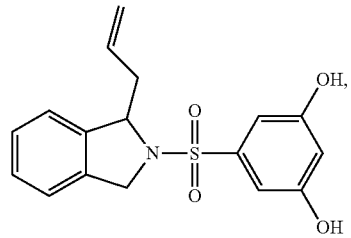

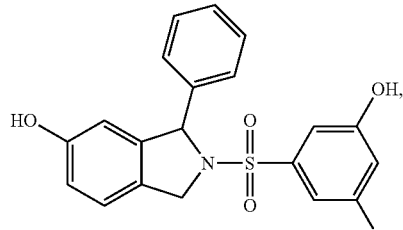

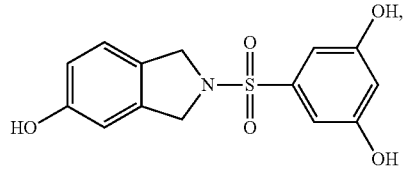

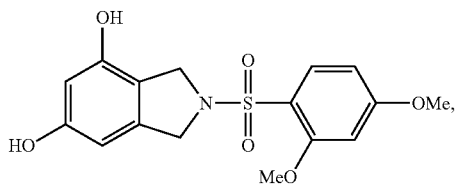

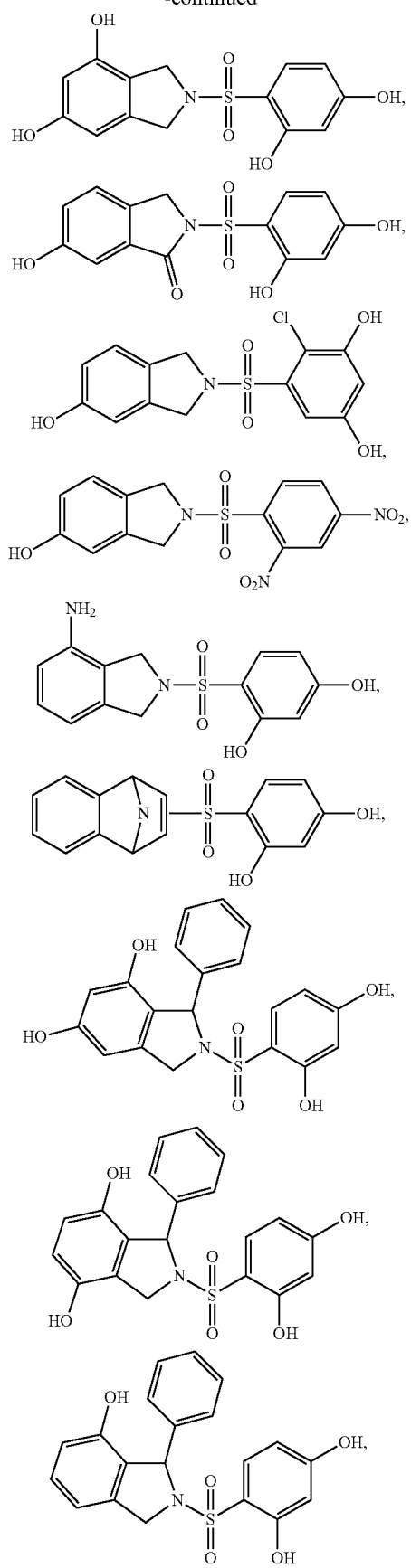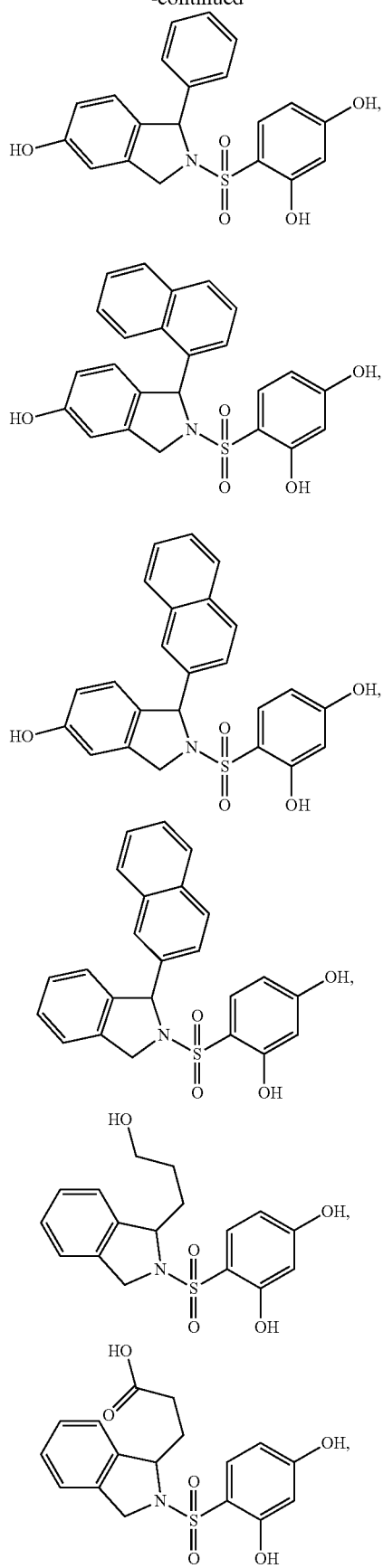

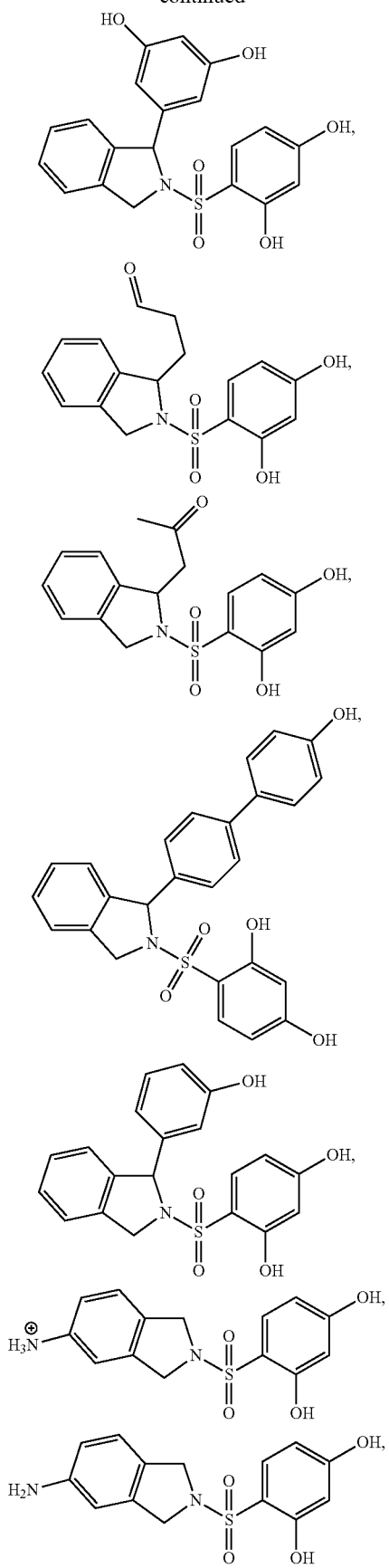
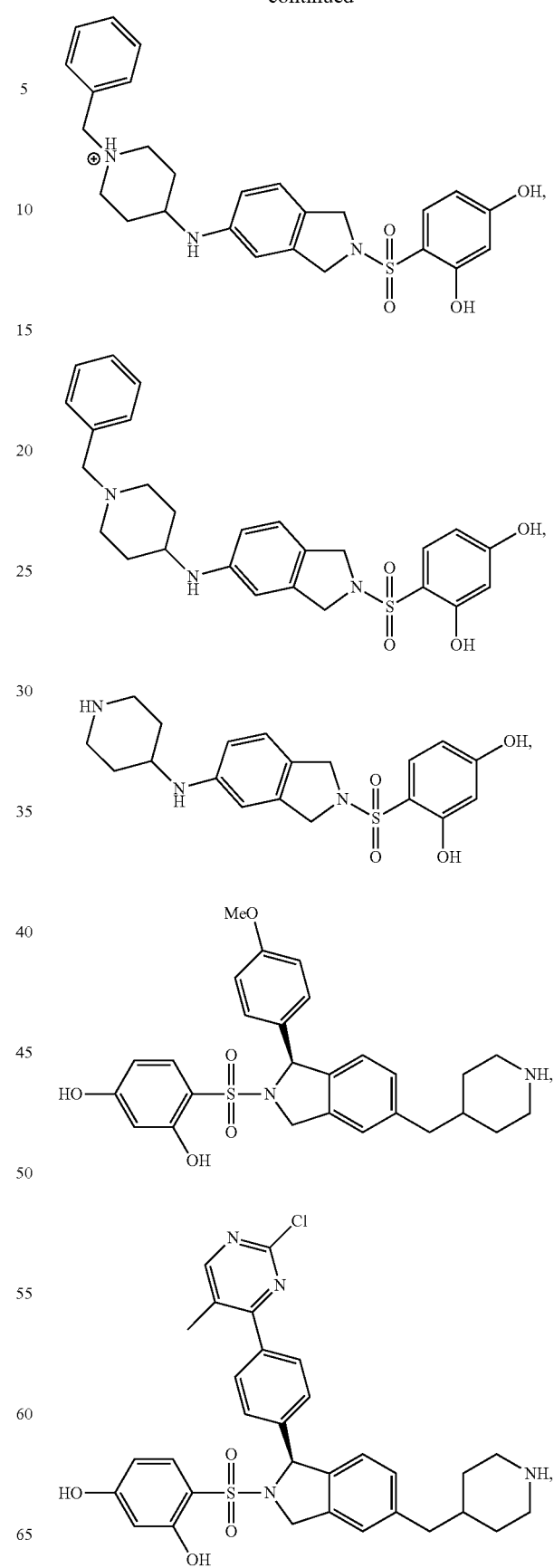

31
-continued

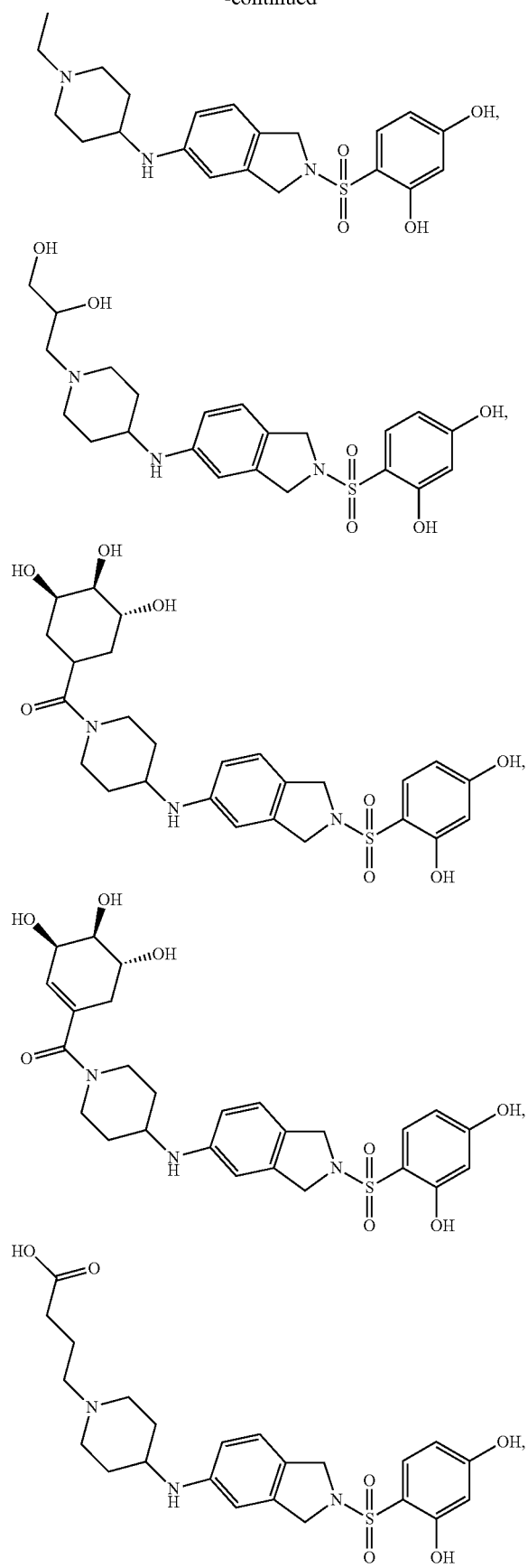

32
-continued

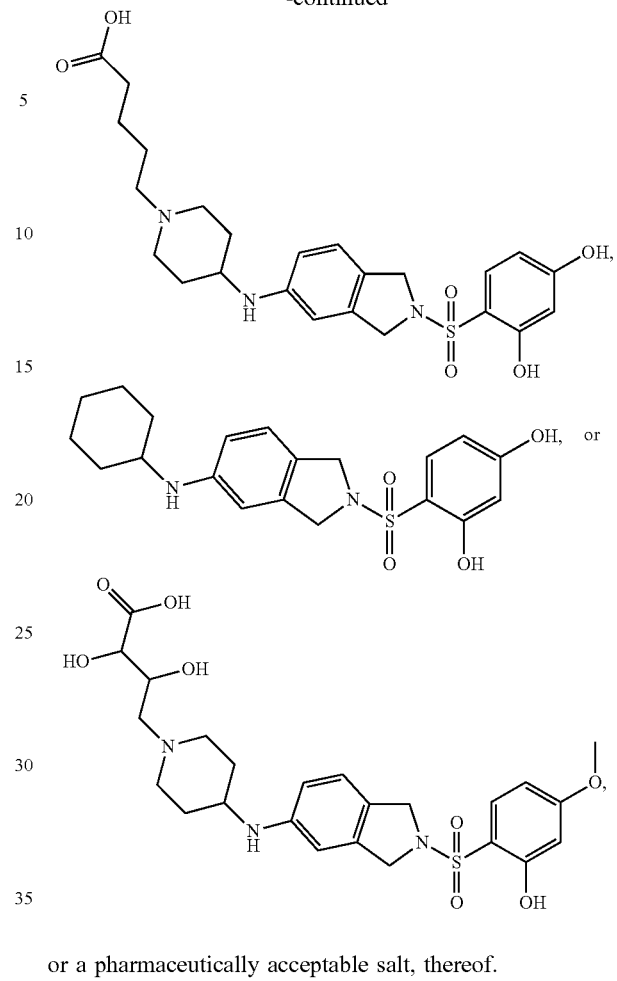

or a pharmaceutically acceptable salt, thereof.

In an even further embodiment, there is provided a method for treating cancer in a subject comprising administering to the subject a therapeutically effective amount of a compound of the formula:

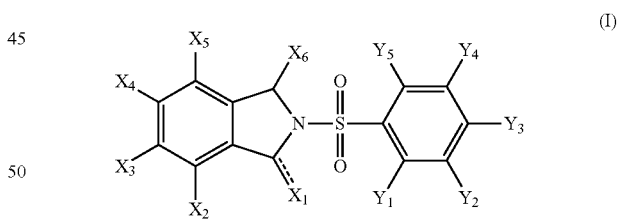

(I)

wherein:
$X_1$ is hydrogen, halogen, hydroxy, amino, cyano, nitro, or oxo, or
alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, —C(O)-alkoxy$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, amido$_{(C\leq12)}$, -arenediyl$_{(C\leq6)}$-heteroaryl$_{(C\leq12)}$, or a substituted version of any of these groups, or is taken together with $X_6$ as defined below;

$X_2$, $X_3$, $X_4$, $X_5$ are each independently hydrogen, halogen, hydroxy, nitro, cyano, or amino, or alkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heterocycloalkyl$_{(C \leq 12)}$, heteroaryl$_{(C \leq 12)}$, acyl$_{(C \leq 12)}$, alkoxy$_{(C \leq 12)}$, alkenyloxy$_{(C \leq 12)}$, alkynyloxy$_{(C \leq 12)}$, aryloxy$_{(C \leq 18)}$, aralkyloxy$_{(C \leq 18)}$, heterocycloalkyloxy$_{(C \leq 12)}$, heteroaryloxy$_{(C \leq 12)}$, acyloxy$_{(C \leq 12)}$, alkylthio$_{(C \leq 12)}$, alkenylthio$_{(C \leq 12)}$, alkynylthio$_{(C \leq 12)}$, arylthio$_{(C \leq 18)}$, aralkylthio$_{(C \leq 18)}$, heterocycloalkylthio$_{(C \leq 12)}$, heteroarylthio$_{(C \leq 12)}$, acylthio$_{(C \leq 12)}$, alkylamine$_{(C \leq 12)}$, dialkylamine$_{(C \leq 12)}$, alkenylamine$_{(C \leq 12)}$, alkynylamine$_{(C \leq 12)}$, arylamine$_{(C \leq 18)}$, aralkylamine$_{(C \leq 18)}$, heterocycloalkylamine$_{(C \leq 12)}$, heteroarylamine$_{(C \leq 12)}$, amido$_{(C \leq 12)}$, -alkanediyl$_{(C \leq 6)}$-heterocycloalkyl$_{(C \leq 12)}$, or a substituted version of any of these groups; or

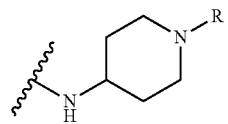

wherein: R is hydrogen; or alkyl$_{(C \leq 12)}$, alkenyl$_{(C \leq 12)}$, acyl$_{(C \leq 12)}$, aryl$_{(C \leq 12)}$, aralkyl$_{(C \leq 12)}$, or a substituted version of any of these groups;

$X_6$ is hydrogen, halogen, hydroxy, amino, nitro, or cyano, or alkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heterocycloalkyl$_{(C \leq 12)}$, heteroaryl$_{(C \leq 12)}$, acyl$_{(C \leq 12)}$, alkoxy$_{(C \leq 12)}$, alkenyloxy$_{(C \leq 12)}$, alkynyloxy$_{(C \leq 12)}$, aryloxy$_{(C \leq 18)}$, aralkyloxy$_{(C \leq 18)}$, heterocycloalkyloxy$_{(C \leq 12)}$, heteroaryloxy$_{(C \leq 12)}$, acyloxy$_{(C \leq 12)}$, alkylamine$_{(C \leq 12)}$, dialkylamine$_{(C \leq 12)}$, alkenylamine$_{(C \leq 12)}$, alkynylamine$_{(C \leq 12)}$, arylamine$_{(C \leq 18)}$, aralkylamine$_{(C \leq 18)}$, heterocycloalkylamine$_{(C \leq 12)}$, heteroarylamine$_{(C \leq 12)}$, or amido$_{(C \leq 12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, or a substituted version of any of these groups;

$X_1$ and $X_6$ when taken together have the formula:

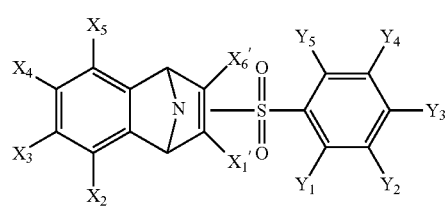

wherein:

$X_1'$ and $X_6'$ are each independently hydrogen, hydroxy, halo, or amino;

alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, acyl$_{(C \leq 12)}$, or a substituted version of any of these groups;

provided that when $X_3$ and $X_4$ are methoxy, then $Y_3$ is not methyl or when $Y_1$ and $Y_3$ are hydroxy or methoxy, then $X_1$, $X_2$, $X_3$, $X_4$, $X_5$, and $X_6$ are not all hydrogen;

or a pharmaceutically acceptable salt thereof.

The method may include a compound further defined as:

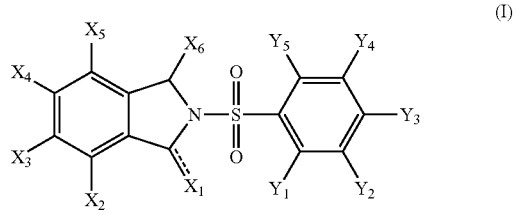

wherein:

$X_1$ is hydrogen, hydroxy, amino, or oxo, or alkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heterocycloalkyl$_{(C \leq 12)}$, heteroaryl$_{(C \leq 12)}$, acyl$_{(C \leq 12)}$, —C(O)-alkoxy$_{(C \leq 12)}$, alkoxy$_{(C \leq 12)}$, alkylamine$_{(C \leq 12)}$, dialkylamine$_{(C \leq 12)}$, -arenediyl$_{(C \leq 6)}$-heteroaryl$_{(C \leq 12)}$, or a substituted version of any of these groups, or is taken together with $X_6$ as defined below;

$X_2$, $X_3$, $X_4$, $X_5$ are each independently hydrogen, hydroxy, or amino, or alkyl$_{(C \leq 12)}$, alkoxy$_{(C \leq 12)}$, heterocycloalkoxy$_{(C \leq 12)}$, alkylthio$_{(C \leq 12)}$, heterocycloalkylthio$_{(C \leq 12)}$, alkylamine$_{(C \leq 12)}$, dialkylamine$_{(C \leq 12)}$, heterocycloalkylamine$_{(C \leq 12)}$, -alkanediyl$_{(C \leq 6)}$-heterocycloalkyl$_{(C \leq 12)}$, or a substituted version of any of these groups; or

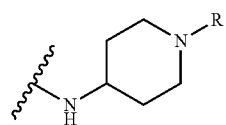

wherein: R is hydrogen; or alkyl$_{(C \leq 12)}$, alkenyl$_{(C \leq 12)}$, acyl$_{(C \leq 12)}$, aryl$_{(C \leq 12)}$, aralkyl$_{(C \leq 12)}$, or a substituted version of any of these groups;

$X_6$ is hydrogen, hydroxy, amino, or alkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heterocycloalkyl$_{(C \leq 12)}$, heteroaryl$_{(C \leq 12)}$, acyl$_{(C \leq 12)}$, alkoxy$_{(C \leq 12)}$, alkenyloxy$_{(C \leq 12)}$, alkynyloxy$_{(C \leq 12)}$, aryloxy$_{(C \leq 18)}$, aralkyloxy$_{(C \leq 18)}$, heterocycloalkyloxy$_{(C \leq 12)}$, heteroaryloxy$_{(C \leq 12)}$, acyloxy$_{(C \leq 12)}$, alkylamine$_{(C \leq 12)}$, dialkylamine$_{(C \leq 12)}$, alkenylamine$_{(C \leq 12)}$, alkynylamine$_{(C \leq 12)}$, arylamine$_{(C \leq 18)}$, aralkylamine$_{(C \leq 18)}$, heterocycloalkylamine$_{(C \leq 12)}$, heteroarylamine$_{(C \leq 12)}$, or amido$_{(C \leq 12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, or a substituted version of any of these groups;

$X_1$ and $X_6$ when taken together have the formula:

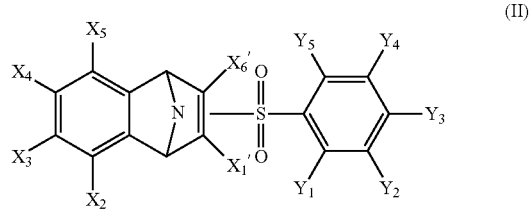

wherein:

$X_1'$ and $X_6'$ are each independently hydrogen, hydroxy, halo, or amino;

alkyl$_{(C \le 12)}$, alkenyl$_{(C \le 12)}$, alkynyl$_{(C \le 12)}$, aryl$_{(C \le 12)}$, aralkyl$_{(C \le 12)}$, heteroaryl$_{(C \le 12)}$, acyl$_{(C \le 12)}$, or a substituted version of any of these groups;

provided that when $X_3$ and $X_4$ are methoxy, then $Y_3$ is not methyl or when $Y_1$ and $Y_3$ are hydroxy or methoxy, then $X_2$, $X_3$, $X_4$, and $X_5$ are not hydrogen;

or a pharmaceutically acceptable salt thereof.

$X_1$ may be hydrogen. Alternatively, $X_1$ may be oxo. $X_2$ and $X_5$ may each independently be hydrogen. $X_2$ and $X_5$ nat each independently be hydroxy or alkoxy$_{(C \le 12)}$. $X_2$ and $X_5$ may each independently be methoxy. $X_3$ and $X_4$ may each independently be hydrogen. $X_3$ and $X_4$ may each independently be hydroxy or alkoxy$_{(C \le 12)}$. $X_3$ and $X_4$ may each independently be methoxy. $X_3$ and $X_4$ may each independently be amino, alkylamino$_{(C \le 12)}$, heterocycloalkylamino$_{(C \le 12)}$, substituted alkylamino$_{(C \le 12)}$, or substituted heterocycloalkylamino$_{(C \le 12)}$. $X_3$ and $X_4$ may each independently be amino, cyclohexylamine, or

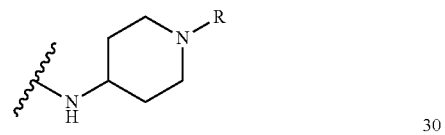

wherein: R is hydrogen; or alkyl$_{(C \le 12)}$, alkenyl$_{(C \le 12)}$, acyl$_{(C \le 12)}$, aryl$_{(C \le 12)}$, aralkyl$_{(C \le 12)}$, or a substituted version of any of these groups.

$X_6$ may be hydrogen. Alternatively, $X_6$ may be alkyl$_{(C \le 12)}$, alkenyl$_{(C \le 12)}$, aryl$_{(C \le 12)}$, or a substituted version of any of these groups.

$Y_1$, $Y_2$, $Y_3$, $Y_4$, and $Y_5$ may each independently be hydrogen. $Y_1$, $Y_2$, $Y_3$, $Y_4$, and $Y_5$ may each independently be halo, hydroxy, or alkoxy$_{(C \le 12)}$. $Y_1$, $Y_2$, $Y_3$, $Y_4$, and $Y_5$ may each independently be hydroxy. $Y_1$, $Y_2$, $Y_3$, $Y_4$, and $Y_5$ may each independently be methoxy. $Y_1$ and $Y_3$ may both be hydroxy or methoxy.

The method may include a compound further defined as:

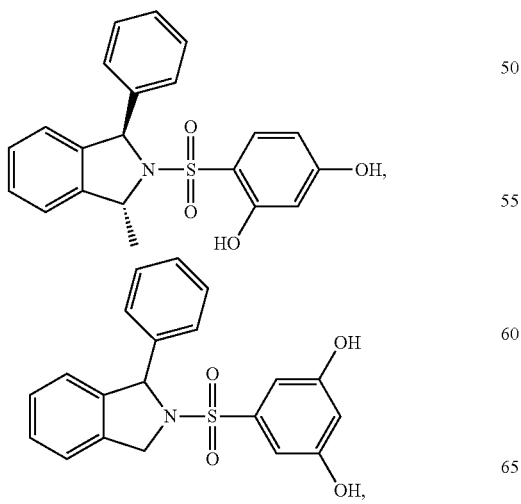

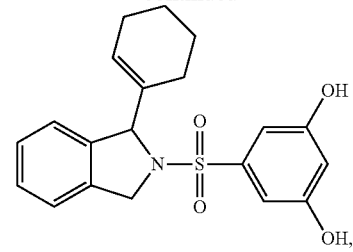

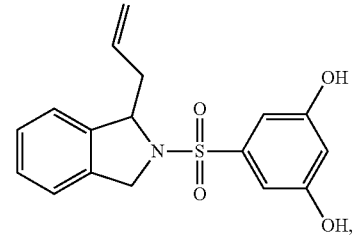

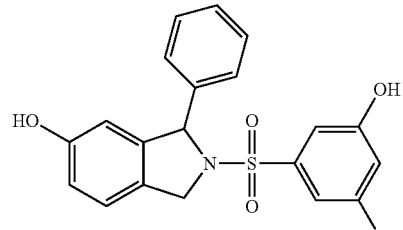

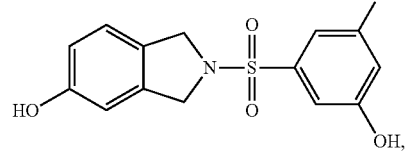

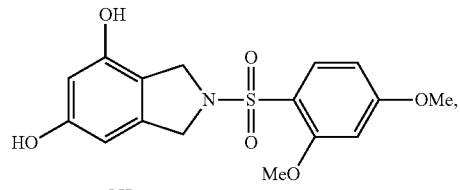

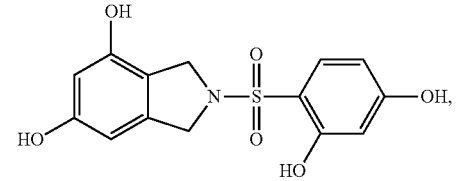

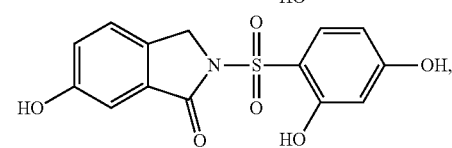

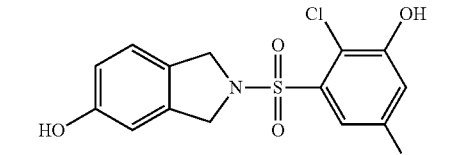

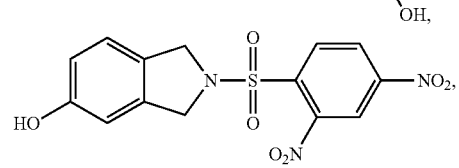

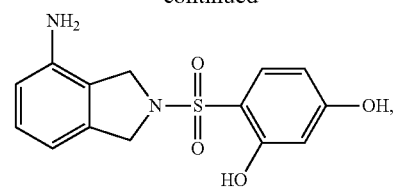
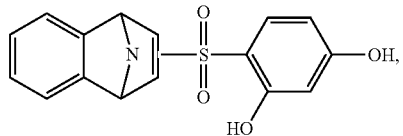
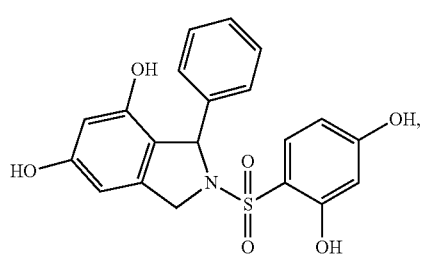
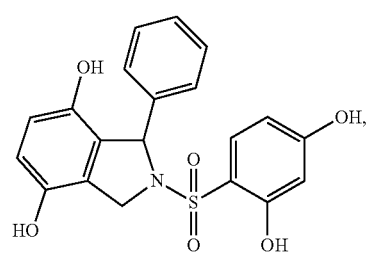
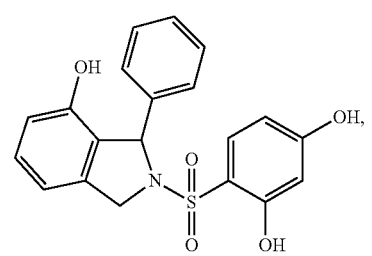
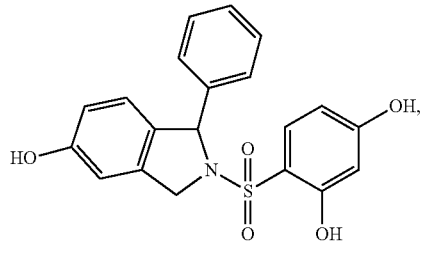
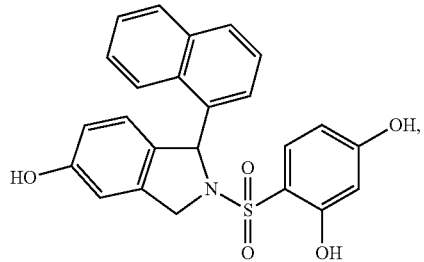
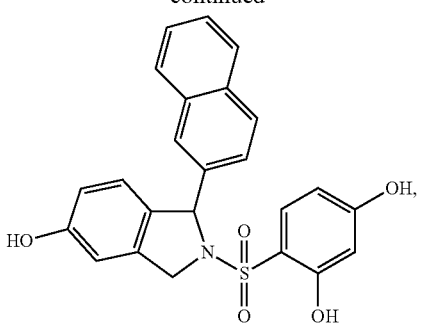
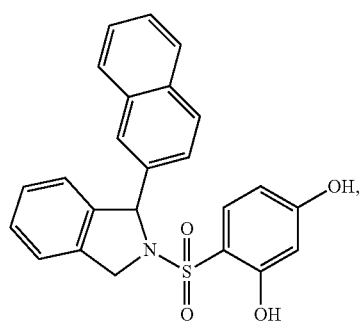
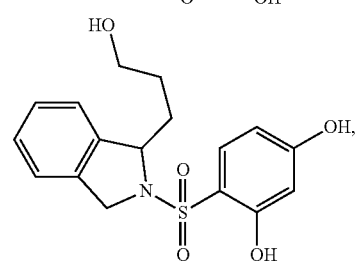
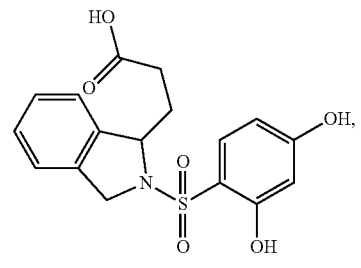
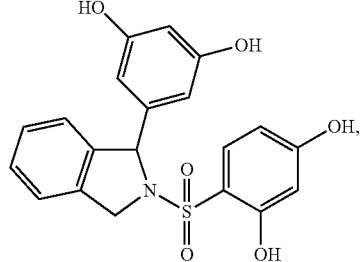
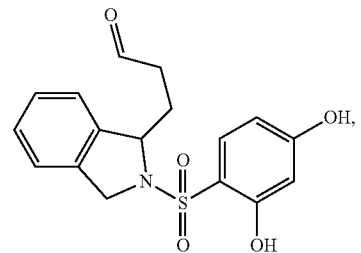

-continued
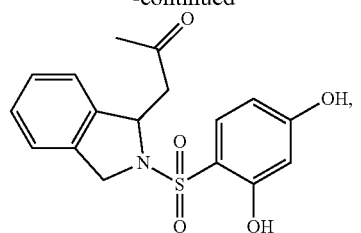
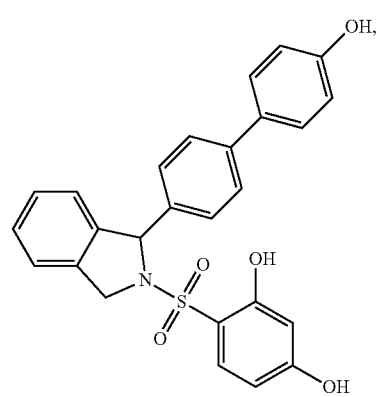
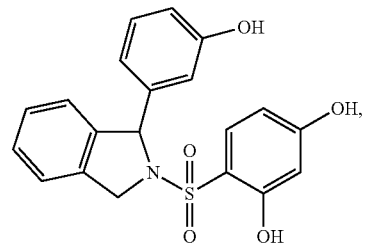
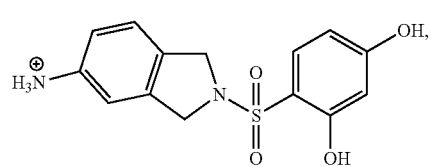
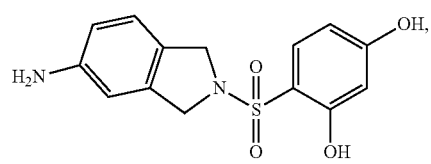
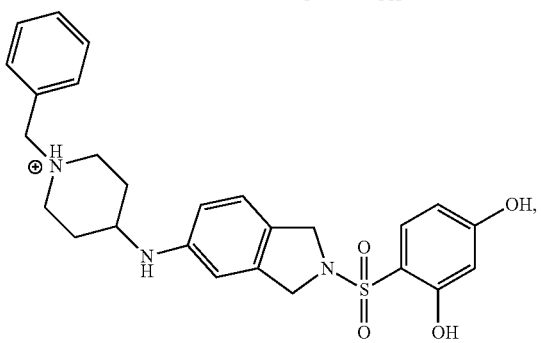
-continued
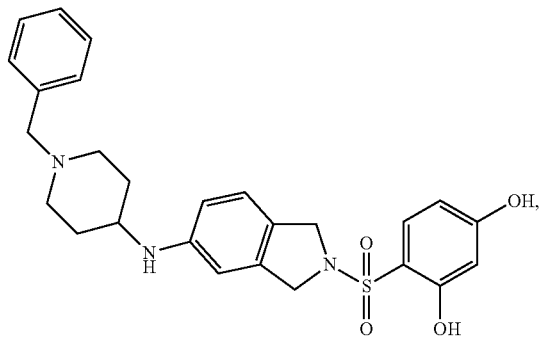
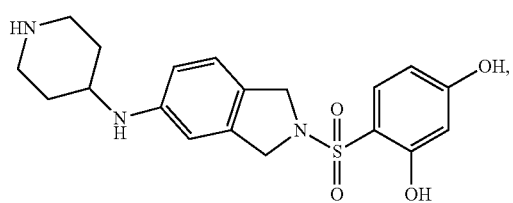
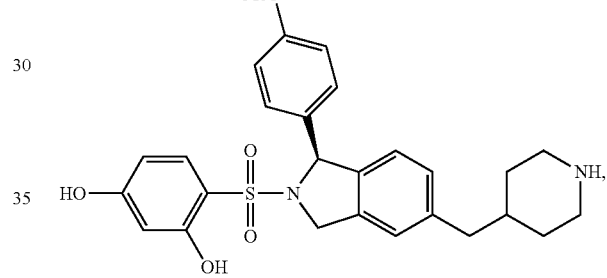
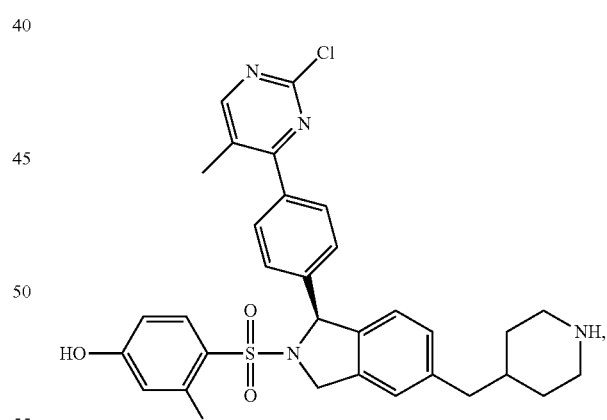
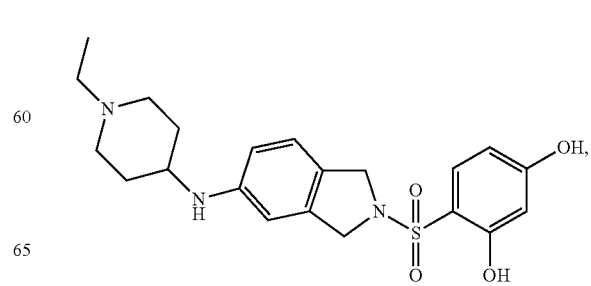

-continued

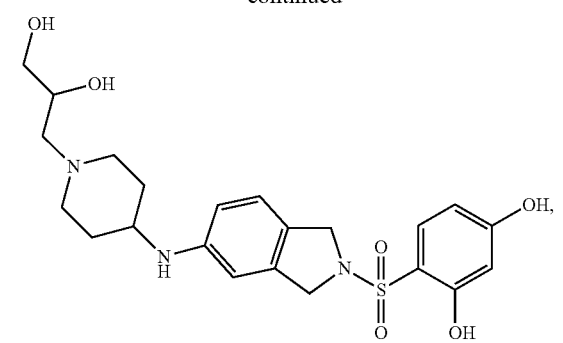

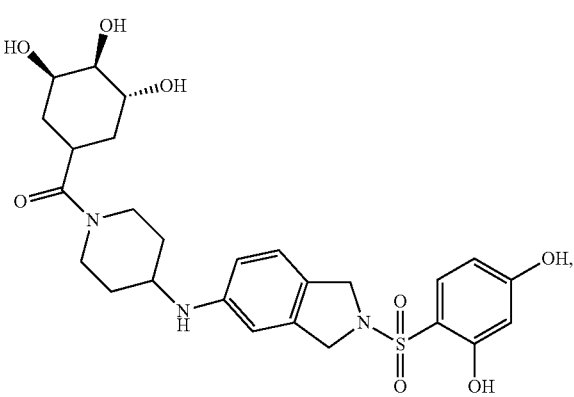

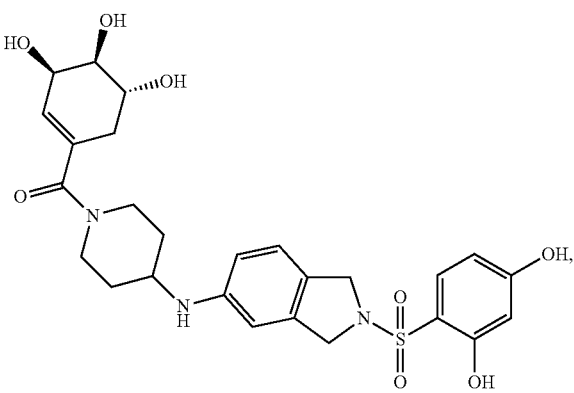

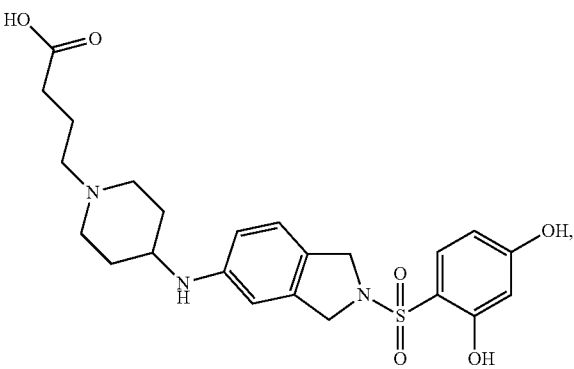

-continued

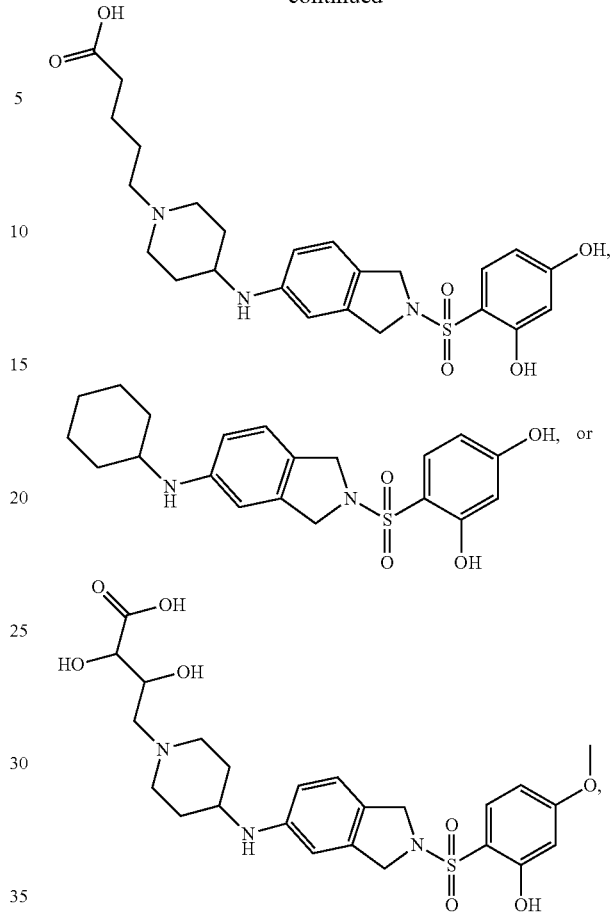

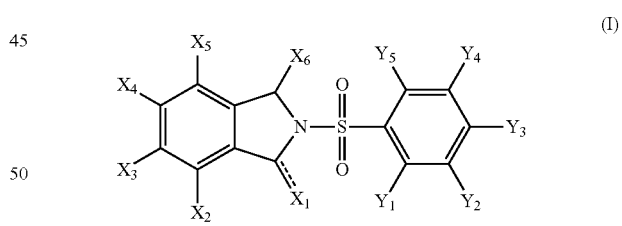

or a pharmaceutically acceptable salt, thereof.

An additional embodiment includes a method for treating heart disease in a subject comprising administering to the subject a therapeutically effective amount of a compound of the formula:

$$\text{(I)}$$

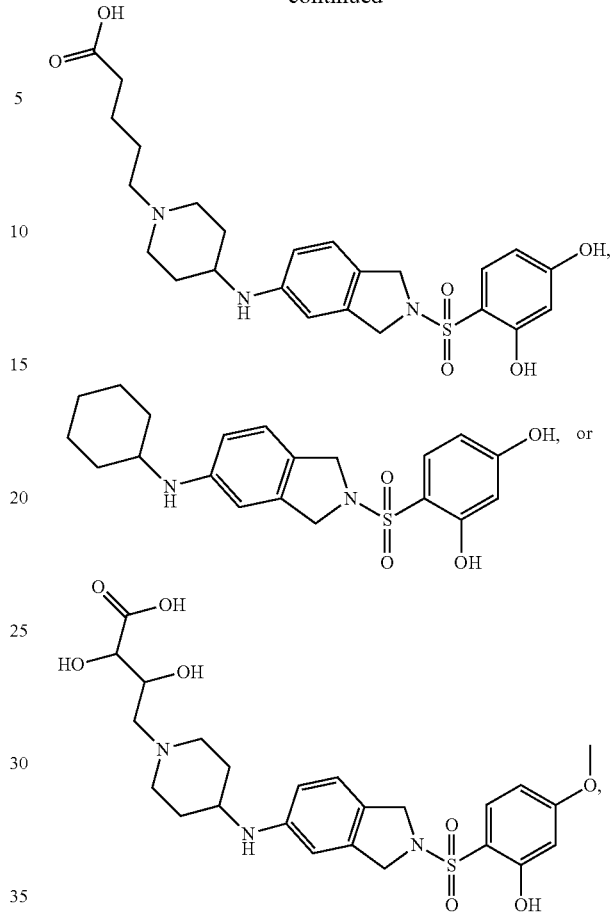

wherein:
$X_1$ is hydrogen, halogen, hydroxy, amino, cyano, nitro, or oxo, or
alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, —C(O)-alkoxy$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, amido$_{(C\leq12)}$, -arenediyl$_{(C\leq6)}$-heteroaryl$_{(C\leq12)}$, or a substituted version of any of these groups, or is taken together with $X_6$ as defined below;

$X_2$, $X_3$, $X_4$, $X_5$ are each independently hydrogen, halogen, hydroxy, nitro, cyano, or amino, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylthio$_{(C\leq12)}$, alkenylthio$_{(C\leq12)}$, alkynylthio$_{(C\leq12)}$, arylthio$_{(C\leq18)}$, aralkylthio$_{(C\leq18)}$, heterocycloalkylthio$_{(C\leq12)}$, heteroarylthio$_{(C\leq12)}$, acylthio$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, amido$_{(C\leq12)}$, -alkanediyl$_{(C\leq6)}$-heterocycloalkyl$_{(C\leq12)}$, or a substituted version of any of these groups; or

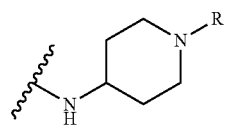

wherein: R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups;

$X_6$ is hydrogen, halogen, hydroxy, amino, nitro, or cyano, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, or amido$_{(C\leq12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, or a substituted version of any of these groups;

$X_1$ and $X_6$ when taken together have the formula:

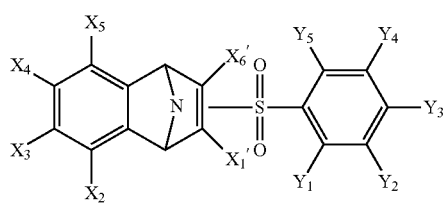

wherein:

$X_1'$ and $X_6'$ are each independently hydrogen, hydroxy, halo, or amino;

alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, acyl$_{(C\leq12)}$, or a substituted version of any of these groups;

or a pharmaceutically acceptable salt thereof.

The method may include a compound further defined by the formula:

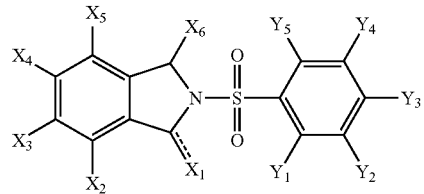

wherein:

$X_1$ is hydrogen, hydroxy, amino, or oxo, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, —C(O)-alkoxy$_{(C\leq12)}$, alkoxy$_{(C\leq12)}$, alkylamine$_{(C\leq12)}$, dialkylamine$_{(C\leq12)}$, -arenediyl$_{(C\leq6)}$-heteroaryl$_{(C\leq12)}$, or a substituted version of any of these groups, or is taken together with $X_6$ as defined below;

$X_2$, $X_3$, $X_4$, $X_5$ are each independently hydrogen, hydroxy, or amino, or alkyl$_{(C\leq12)}$, alkoxy$_{(C\leq12)}$, heterocycloalkoxy$_{(C\leq12)}$, alkylthio$_{(C\leq12)}$, heterocycloalkylthio$_{(C\leq12)}$, alkylamine$_{(C\leq12)}$, dialkylamine$_{(C\leq12)}$, heterocycloalkylamine$_{(C\leq12)}$, -alkanediyl$_{(C\leq6)}$-heterocycloalkyl$_{(C\leq12)}$, or a substituted version of any of these groups; or

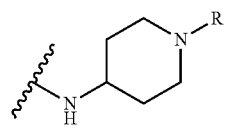

wherein: R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups;

$X_6$ is hydrogen, hydroxy, amino, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, or amido$_{(C\leq12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$; heterocycloalkyl$_{(C\leq12)}$, acyl$_{(C\leq12)}$, or a substituted version of any of these groups;

$X_1$ and $X_6$ when taken together have the formula:

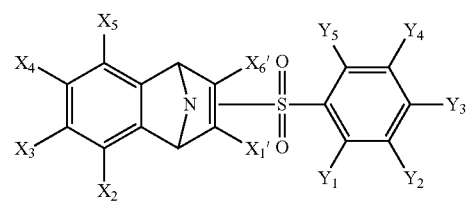

wherein:

$X_1'$ and $X_6'$ are each independently hydrogen, hydroxy, halo, or amino;

alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, acyl$_{(C\leq12)}$, or a substituted version of any of these groups;

or a pharmaceutically acceptable salt thereof.

$X_1$ may be hydrogen. Alternatively, $X_1$ may be oxo. $X_2$ and $X_5$ may each independently be hydrogen. $X_2$ and $X_5$ nat each independently be hydroxy or alkoxy$_{(C\leq12)}$. $X_2$ and $X_5$ may each independently be methoxy. $X_3$ and $X_4$ may each independently be hydrogen. $X_3$ and $X_4$ may each independently be hydroxy or alkoxy$_{(C\leq12)}$. $X_3$ and $X_4$ may each independently be methoxy. $X_3$ and $X_4$ may each independently be amino, alkylamino$_{(C\leq12)}$, heterocycloalkylamino$_{(C\leq12)}$, substituted alkylamino$_{(C\leq12)}$, or substituted heterocycloalkylamino$_{(C\leq12)}$. $X_3$ and $X_4$ may each independently be amino, cyclohexylamine, or

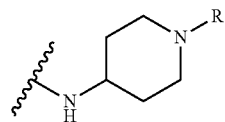

wherein: R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups.

$X_6$ may be hydrogen. Alternatively, $X_6$ may be alkyl$_{(C\leq12)}$, alkenyl$_{(C\leq12)}$, aryl$_{(C\leq12)}$, or a substituted version of any of these groups.

$Y_1$, $Y_2$, $Y_3$, $Y_4$, and $Y_5$ may each independently be hydrogen. $Y_1$, $Y_2$, $Y_3$, $Y_4$, and $Y_5$ may each independently be halo, hydroxy, or alkoxy$_{(C\leq12)}$ $Y_1$, $Y_2$, $Y_3$, $Y_4$, and $Y_5$ may each independently be hydroxy. $Y_1$, $Y_2$, $Y_3$, $Y_4$, and $Y_5$ may each independently be methoxy. $Y_1$ and $Y_3$ may both be hydroxy or methoxy.

The method may include a compound further defined as:

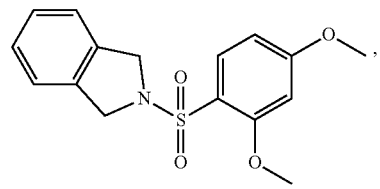

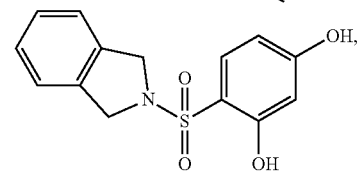

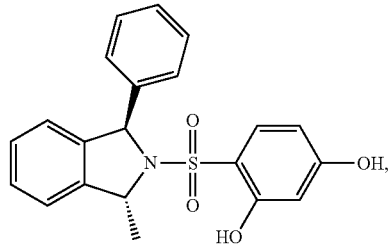

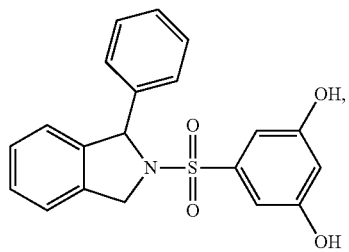

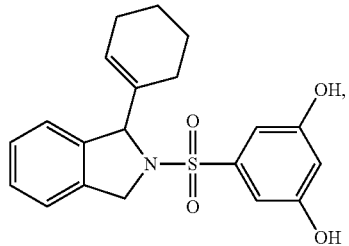

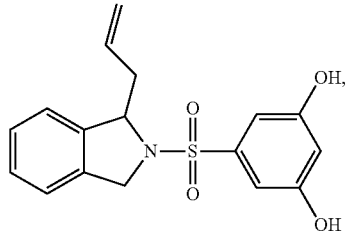

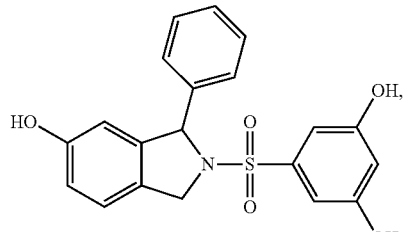

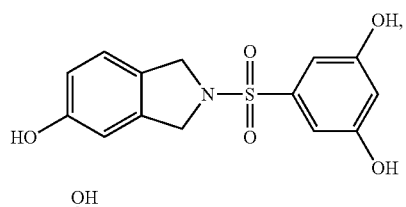

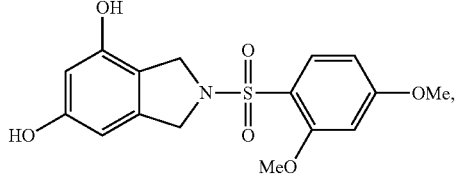

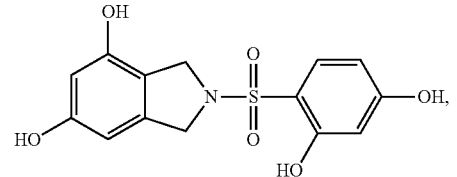

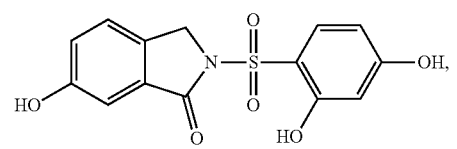

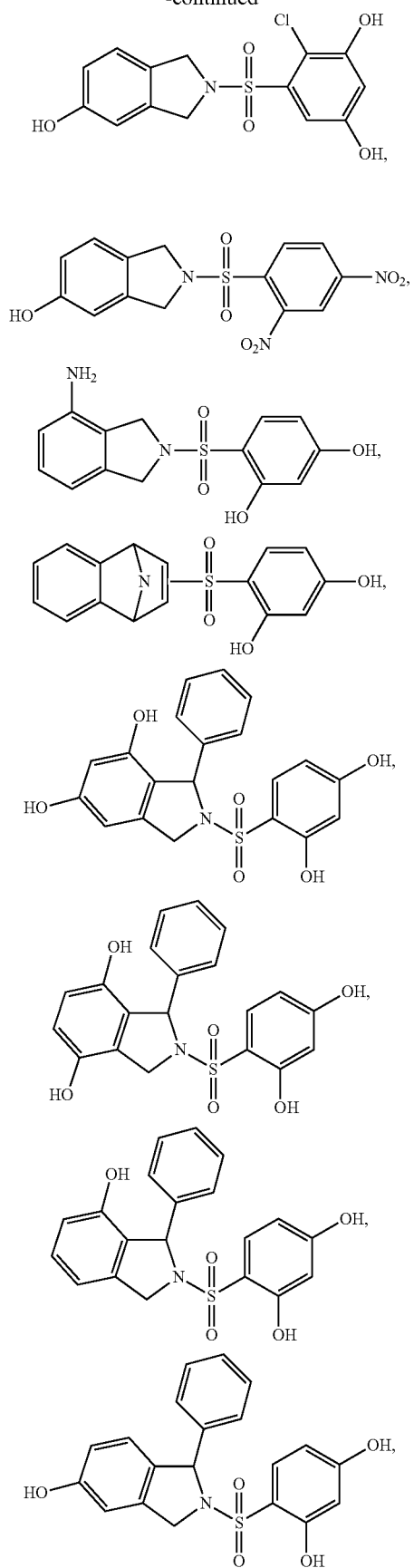
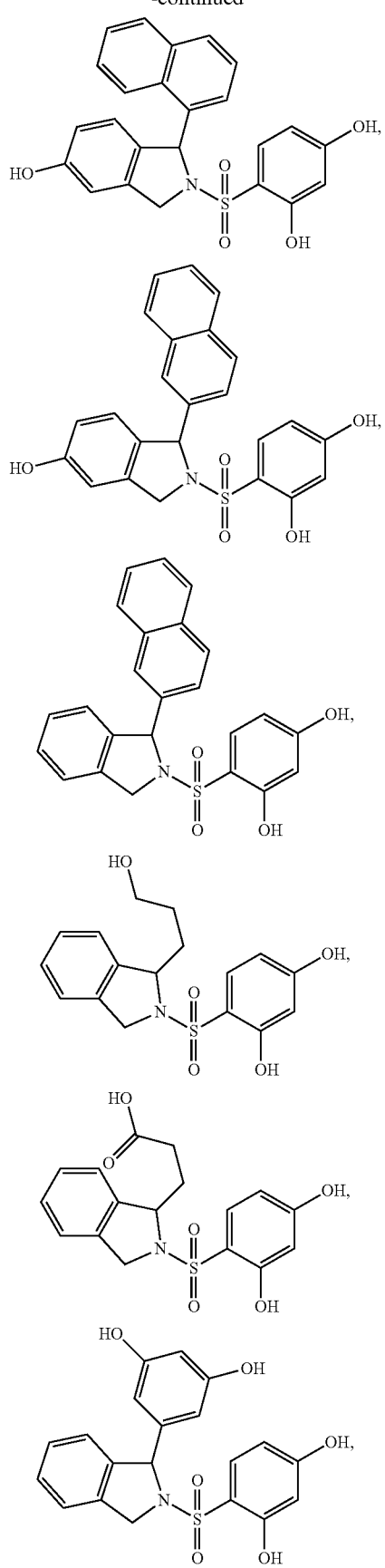

-continued
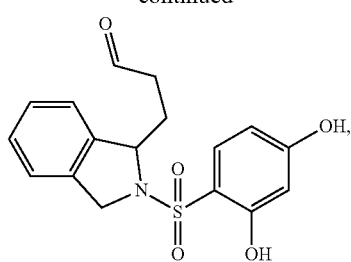
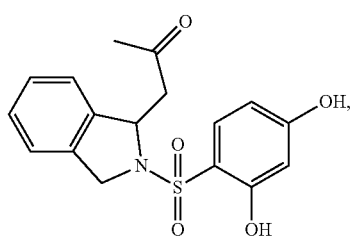
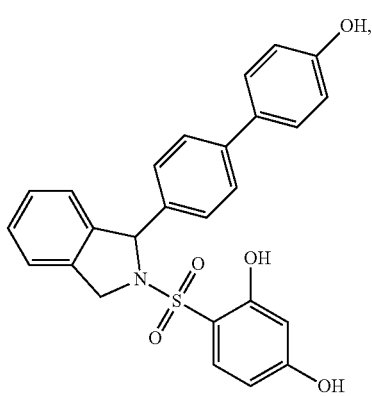
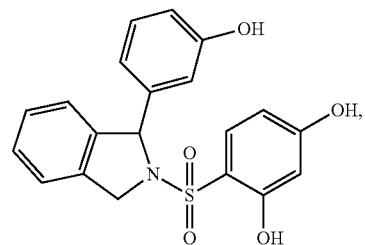
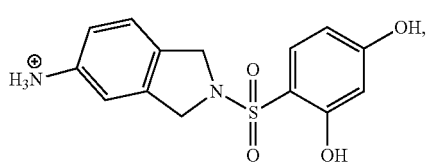
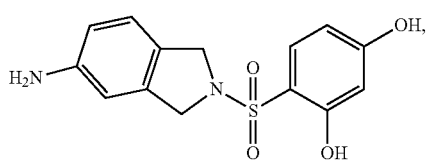
-continued
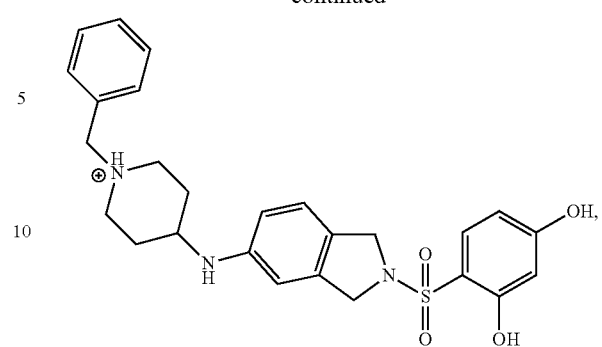
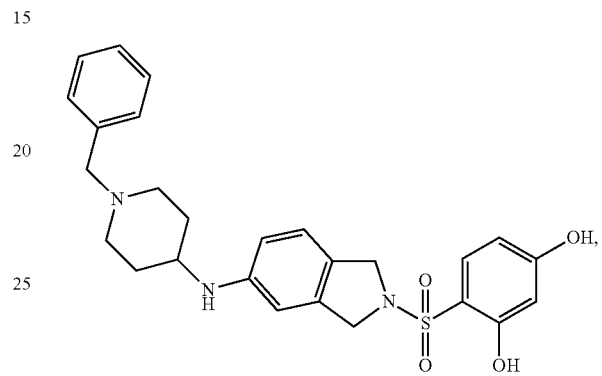
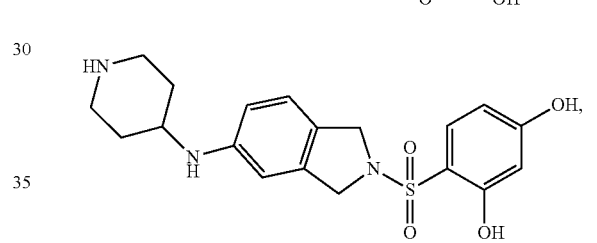
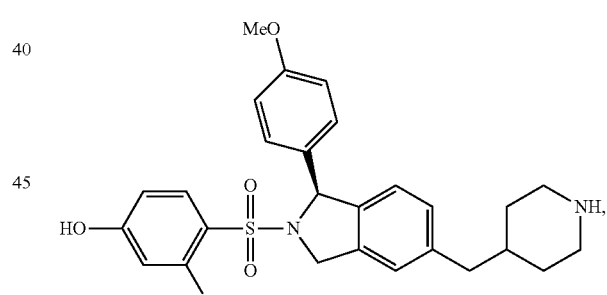
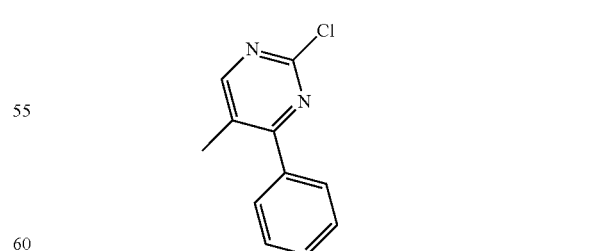
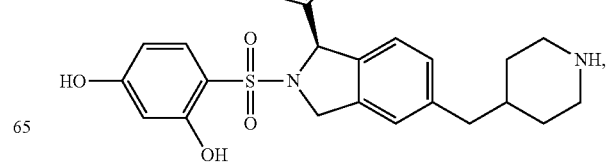

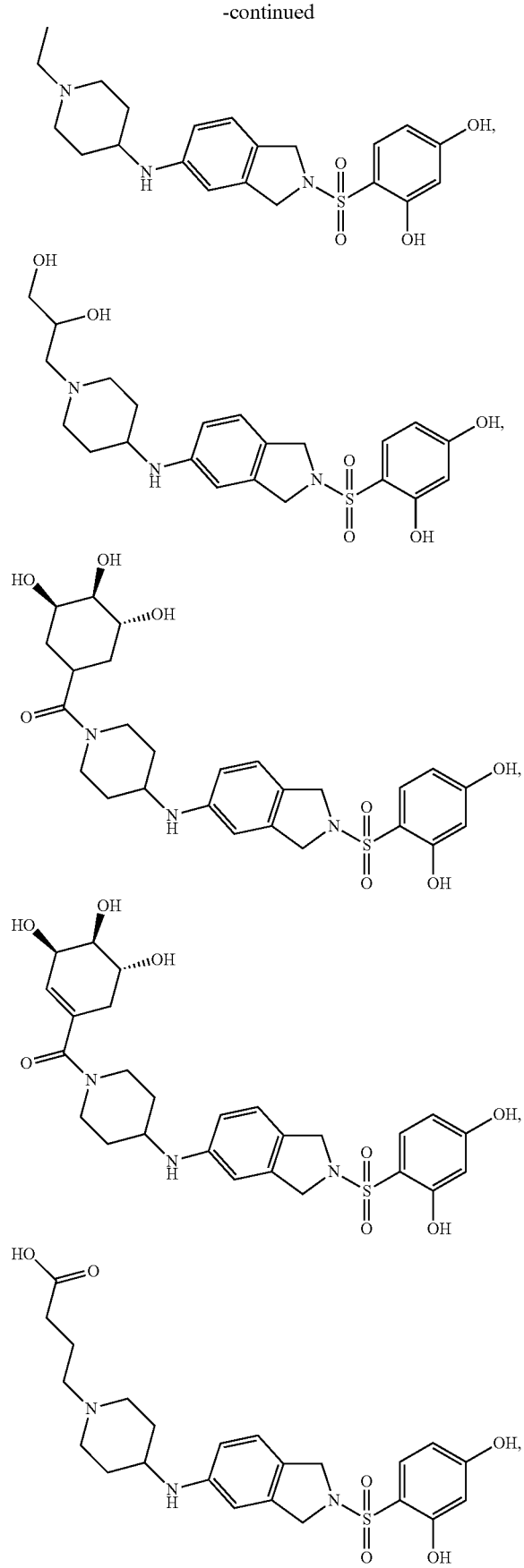
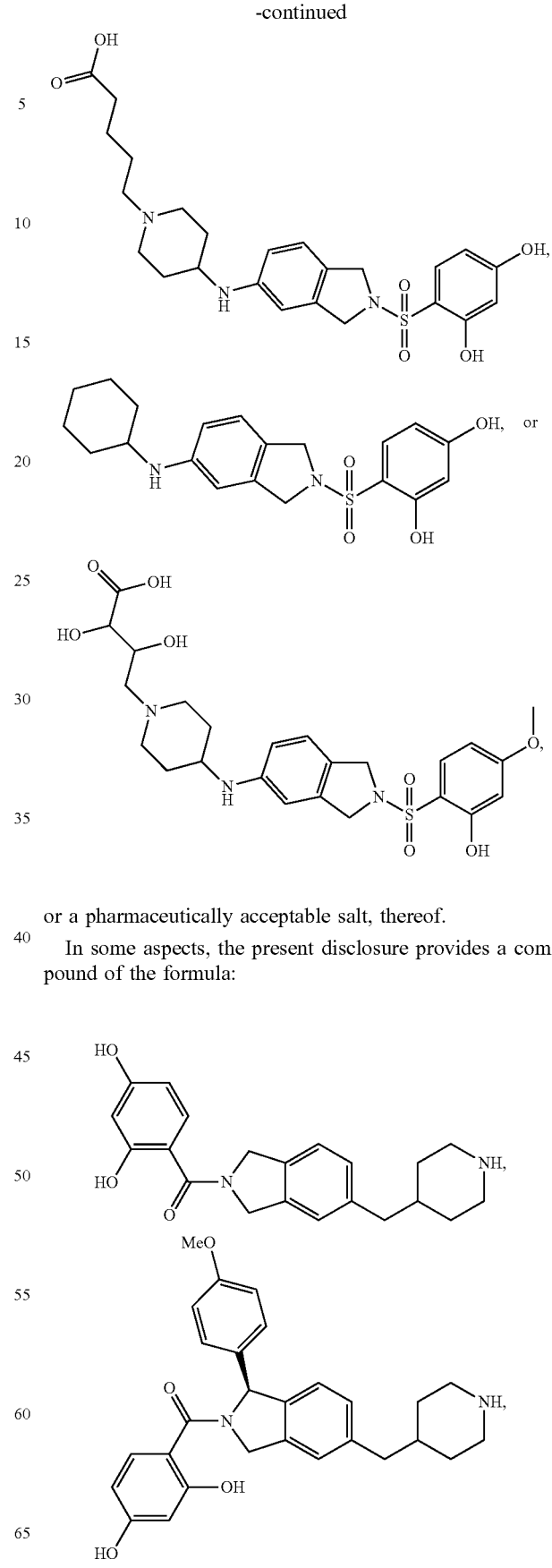
or a pharmaceutically acceptable salt, thereof.
In some aspects, the present disclosure provides a compound of the formula:

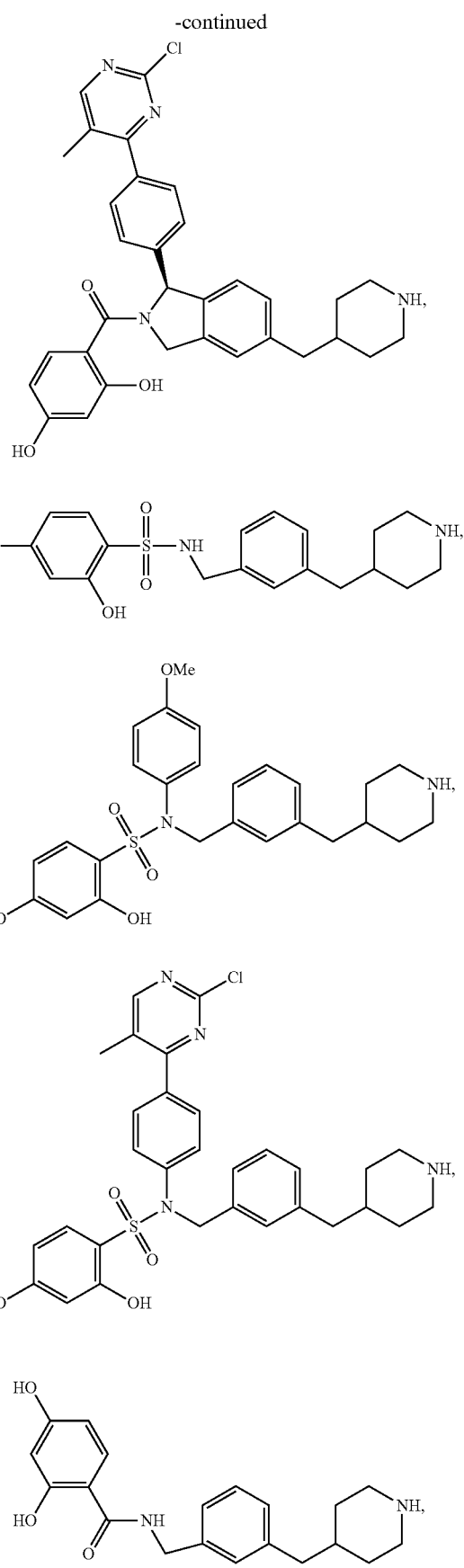
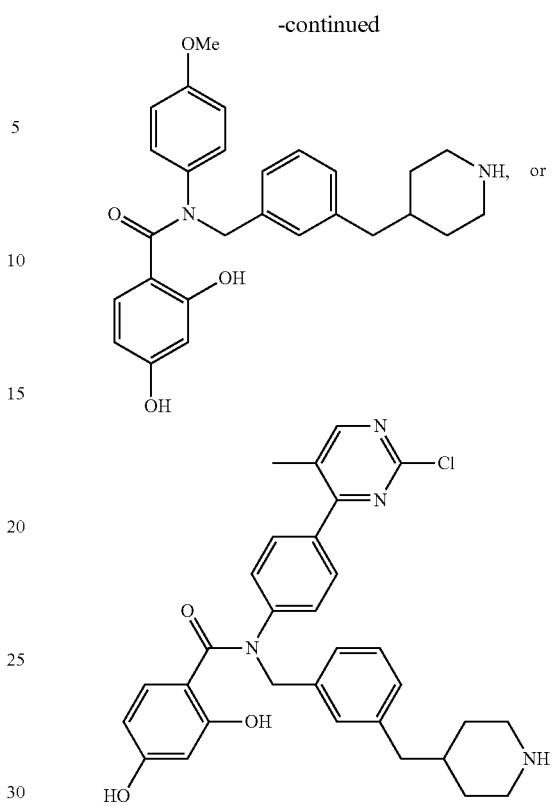

or a pharmaceutically acceptable salt thereof. In yet another aspect, any of these compounds are also useful in any of the above methods.

In any of the preceding embodiments, the cell is located in an animal subject.

In any of the preceding embodiments, the cell is contacted ex vivo.

The terms "contacted" and "exposed," when applied to a cell, are used herein to describe the process by which a compound of the invention is delivered to a target cell or is placed in direct juxtaposition with the target cell.

The term "effective," as that term is used in the specification and/or claims (e.g., "an effective amount," means adequate to accomplish a desired, expected, or intended result.

"Treatment" and "treating" as used herein refer to administration or application of a therapeutic agent to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following figures form part of the present specification and are included to further demonstrate certain aspects of the present invention. The invention may be better understood by reference to one or more of these drawings in combination with the detailed description of specific embodiments presented herein.

(FIG. 1A) The PDK dimer showing AZD7545, and dichloroacetate-binding sites in N-terminal domain (pink); and radicicol bound to the ATP-binding pocket in the C-terminal domain (green). (FIG. 1B) Chemical structures of known PDK inhibitors: DCA, AZD7545, compound 3, radicicol, and M77976; and novel PDK inhibitors: DC23, PA1, PA7, PS2, PS8, and PS10. The resorcinol ring is indicated in red and isoindoline moiety in blue.

FIGS. 2A-I. Crystal structures of inhibitor-binding pockets in PDK2 and Hsp90. (FIG. 2A) Superimposition of the C-terminal domain of PDK2 (green) harboring PA7 (pink) with the N-terminal domain of Hsp90 (orange) with bound PA7 (cyan). (FIG. 2B) PA7 in Hsp90 (FIG. 2C) PA7 in PDK2, (FIG. 2D) superimposition of Hsp90-bound (cyan) and PDK2-bound PA7 (pink) (left), and the structure of PDK2-bound PS2 (right). (FIG. 2E) Hsp90-PA7 structure (PDB code 3K99) (33). (FIG. 2F) PDK-PA7 structure with Fo-Fc density map (green mesh) contoured to 4σ. (FIG. 2G) PDK-PS2 structure with density map to 4σ. (FIG. 2H) PDK-PS8 structure with density map to 3σ. (FIG. 2I) PDK-PS10 structure with density map to 3σ.

(FIG. 3A) Thermograms of PS10 binding to PDK2 and Hsp90 obtained by ITC. (FIG. 3B) Thermodynamic signatures of inhibitor bindings to PDK2 (left panel) and Hsp90 (right panel), ΔG, Gibbs binding energy; ΔH, binding enthalpy; ΔS, binding entropy; T, absolute temperature.

(FIG. 5A) Short-term response. C57BL/6J male mice were fed high-fat diet for 3 weeks and treated with vehicle (V, n=4) or PS10 at 70 mg/kg (T, n=4) by a single IP injection while they had free access to food. Animals were sacrificed at 10 AM, i.e., 10 h after the injection. Tissues were harvested and analyzed for PDC activity and phosphorylation levels of E1α subunit. Upper panel, PDC activity in heart, liver, kidney and muscle. Lower panel, amounts of the phosphorylated (p-E1) and total (E1) E1α subunit in different tissues determined by Western blotting analysis. (FIG. 5B) Long-term response. C57BL/6J male mice were fed high-fat diet for 10 weeks and then treated with vehicle (n=3) or PS10 at 70 mg/kg/day (n=3) for 3 days. The remaining procedures and result presentation are as in FIG. 5A. **, P<0.01; *, P<0.05.

(FIG. 6A) Glucose tolerance test. C57BL/6J male mice were fed a high-fat diet for 10 weeks and treated with vehicle (n=4) or PS10 at 70 mg/kg/day (n=6) for 4 weeks and were fasted for 6 h followed by injection of 1.5 g glucose/kg by IP injection. Blood glucose levels were monitored at 0-2 h after the glucose injection. (FIG. 6B) Food intake of DIO mice fed the high-fat diet for 10 weeks followed by treatments with vehicle (n=5) or PS10 at 70 mg/kg/day (n=5) for one week. (FIG. 6C) Body weight change in DIO mice from FIG. 6A after 6 week of treatments with vehicle or PS10. (FIG. 6D) Plasma lactate concentrations in DIO mice from FIG. 6B. Plasma lactate concentrations were determined as described in the Methods. (FIG. 6E) Plasma cholesterol concentration in DIO mice from FIG. 6C. (FIG. 6F) Plasma triglycerides concentrations in DIO mice also from FIG. 6C. (FIG. 6G) Change in the fat mass. DIO mice were treated as in FIG. 6B. Fat mass was determined as described in Methods. (FIG. 6H) Oil Red O stains of liver slices from vehicle- and PS10-treated DIO mice as in FIG. 6B. *, P<0.001; , P<0.01; *, P<0.05; ns, not significant statistically.

(FIG. 8A) Hsp90-PA7 structure (1). (FIG. 8B) PDK2-PA1 structure with Fo-Fc density map (green mesh) contoured to 4σ. (FIG. 8C) PDK2-PA7 structure with map contoured to 4σ. (FIG. 8D) PDK2-PS2 structure to 4σ. (FIG. 8E) PDK2-PS8 structure with map contoured to 3σ. (FIG. 8F) PDK2-PS10 structure with map contoured to 3σ. W, ordered water molecule.

FIGS. 9A-H. Comparison of PS10 and DCA in Glucose- and lipid-controlling properties. (FIG. 9A) Glucose tolerance test. C57BL/6J male mice were fed a high-fat diet for 4 weeks and treated for 6 days with vehicle (n=4), PS10 at 70 mg/kg/day (n=4) or DCA at 250 mg/kg/day (n=4) and were fasted for 6 h followed by injection of 1.5 g glucose/kg by IP injection. Blood glucose levels were monitored at 0-2 h after the glucose injection. (FIG. 9B) Food intake of DIO mice from FIG. 9A after the treatments of vehicle and PS10 for one week. (FIG. 9C) Body weight change in DIO mice from FIG. 9A after 1 week of treatments with vehicle, PS10 and DCA. (FIG. 9D) Plasma lactate concentrations in DIO mice from FIG. 9C. (FIG. 9E) Plasma cholesterol concentration in DIO mice from FIG. 9C. (FIG. 9F) Plasma triglycerides concentrations in DIO mice also from FIG. 9C. (FIG. 9G) Plasma insulin concentration in DIO mice from FIG. 9C. (FIG. 9H) Oil Red O stains of liver slices from vehicle- and PS10-treated DIO mice as in FIG. 9B. *, P<0.001; , P<0.01; *, P<0.05, as compared with vehicle-treated group.

(FIG. 10A) A $^{13}$C spectrum following injection of HP [1-$^{13}$C]pyruvate into a perfused mouse heart. (FIG. 10B) Integrated intensities for [$^{13}$C]bicarbonate representing PDC flux. DIO mice were treated with a single dose DCA (250 mg/kg 1-h) or PS10 (70 mg/kg, 8-hr) by IP injection.

(FIG. 12A) Regulation of hepatic lipogenesis by ChREBP and SREBP-1c. (FIG. 12B) Increased hepatic glucose oxidation in PS10 treated-DIO mice restores systemic insulin sensitivity.

(FIG. 13A) Derivatives to be synthesized from the PS-Br precursor. (FIG. 13B) PDK2 structure with the bound PS35 and tartrate.

(FIG. 14A) Structure of PS42 in ATP-pocket of PDK2. (FIG. 14B) Close-up of the interaction between PDK2 and the extended moiety of PS42. Red dash lines represent hydrogen bonds. (FIG. 14C) Interaction between tartrate and PDK2.

FIGS. 15A-B. Inhibitor designs extending into the phosphate region. (FIG. 15A) Superimposition of bound PS10 and ATP in the ATP-binding pocket. Dashed circle: resorcinol ring. (FIG. 15B) Synthesis of PS-series compounds with R1 modifications.

FIG. 16. List of compounds to be synthesized to test the extension into the phosphate region of the ATP-binding pocket of PDK.

DESCRIPTION OF ILLUSTRATIVE EMBODIMENTS

Figure 1A:
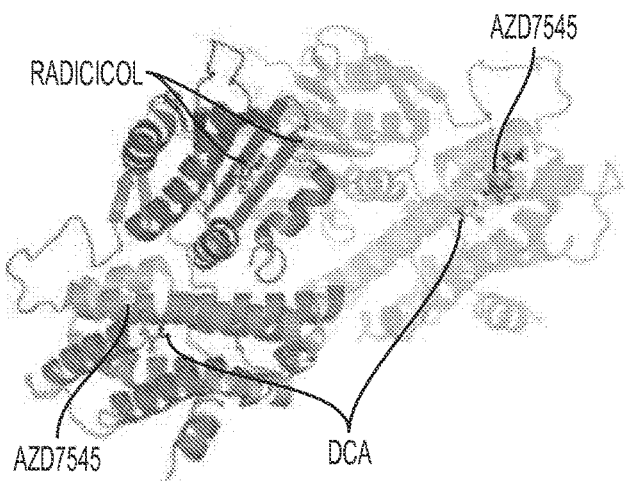
FIGS. 1A-B. Structure of PDK2 and known and novel inhibitors.

Here, the inventors sought to develop robust PDK inhibitors that can be used to improve glucose metabolism and correct metabolic dysfunction in vivo. Based on the unique structural features present in the ATP-binding pocket of PDK2, a single functional-group change was made in a known Hsp90 inhibitor that binds to the corresponding pocket of the latter protein (30,31) from the GHKL family. This approach efficiently converted the Hsp90 inhibitor to a highly specific inhibitor for all PDK isoforms. These final PDK inhibitors of this series robustly augments PDC activity with reduced phosphorylation in tissues, which leads to improved glucose tolerance and reduced hepatic steatosis in diet-induced obese (DIO) mice. These findings demonstrate the utility of structure-based inhibitor design and support the pharmacological approach of targeting PDK to control glucose and fat levels in obesity and type 2 diabetes, and point toward other applications including the treatment of heart disease and cancer.

These and other aspects of the disclosure are set out in detail below.

I. PYRUVATE DEHYDROGENASE KINASE

Pyruvate dehydrogenase kinase (also pyruvate dehydrogenase complex kinase, PDC kinase, or PDK) is a kinase enzyme which acts to inactivate the enzyme pyruvate dehydrogenase by phosphorylating it using ATP. PDK thus participates in the regulation of the pyruvate dehydrogenase complex of which pyruvate dehydrogenase is the first component. Both PDK and the pyruvate dehydrogenase complex are located in the mitochondrial matrix of eukaryotes. The complex acts to convert pyruvate (a product of glycolysis in the cytosol) to acetyl-CoA, which is then oxidized in the mitochondria to produce energy, in the citric acid cycle. By downregulating the activity of this complex, PDK will decrease the oxidation of pyruvate in mitochondria and increase the conversion of pyruvate to lactate in the cytosol.

The opposite action of PDK, namely the dephosphorylation and activation of pyruvate dehydrogenase, is catalyzed by a phosphoprotein phosphatase called pyruvate dehydrogenase phosphatase. Pyruvate dehydrogenase kinase should not be confused with Phosphoinositide-dependent kinase-1, which is also sometimes known as "PDK1".

PDK can phosphorylate a serine residue on pyruvate dehydrogenase at three possible sites. Some evidence has shown that phosphorylation at site 1 will nearly completely deactivate the enzyme while phosphorylation at sites 2 and 3 had only a small contribution to complex inactivation. Therefore, it is phosphorylation at site 1 that is responsible for pyruvate dehydrogenase deactivation.

There are four known isozymes of PDK in humans: PDK1, PDK2, PDK3 and PDK4. The primary sequencing between the four isozymes are conserved with 70% identity. The greatest differences occur near the N-terminus PDK1 is the largest of the four with 436 residues while PDK2, PDK3 and PDK4 have 407, 406, and 411 residues respectively. The isozymes have different activity and phosphorylation rates at each site. At site 1 in order from fastest to slowest, PDK2>PDK4≈PDK1>PDK3. For site 2, PDK3>PDK4>PDK2>PDK1. Only PDK1 can phosphorylate site 3. However, it has been shown that these activities are sensitive to slight changes in pH so the microenvironment of the PDK isozymes may change the reaction rates.

Isozyme abundance has also been shown to be tissue specific. PDK1 is ample in heart cells. PDK3 is most abundant in testis. PDK2 is present in most tissues but low in spleen and lung cells. PDK4 is predominantly found in skeletal muscle and heart tissues.

Pyruvate dehydrogenase is deactivated when phosphorylated by PDK. Normally, the active site of pyruvate dehydrogenase is in a stabilized and ordered conformation supported by a network of hydrogen bonds. However, phosphorylation by PDK at site 1 causes steric clashes with another nearby serine residue due to both the increased size and negative charges associated with the phosphorylated residue. This disrupts the hydrogen bond network and disorders the conformation of two phosphorylation loops. These loops prevent the reductive acetylation step, thus halting overall activity of the enzyme. The conformational changes and mechanism of deactivation for phosphorylation at sites 2 and 3 are not known at this time.

Pyruvate dehydrogenase kinase is stimulated by ATP, NADH and acetyl-CoA. It is inhibited by ADP, NAD+, CoA-SH and pyruvate. Each isozyme responds slightly differently to each of these factors. NADH stimulates PDK1 activity by 20% and PDK2 activity by 30%. NADH with acetyl-CoA increases activity in these enzymes by 200% and 300% respectively. In similar conditions, PDK3 is unresponsive to NADH and inhibited by NADH with acetyl-CoA. PDK4 has a 200% activity increase with NADH, but adding acetyl-CoA does not increase activity further.

Some studies have shown that cells that lack insulin (or are insensitive to insulin) overexpress PDK4. As a result, the pyruvate formed from glycolysis cannot be oxidized which leads to hyperglycaemia due to the fact that glucose in the blood cannot be used efficiently. Therefore several drugs target PDK4 hoping to treat type II diabetes.

PDK1 has shown to have increased activity in hypoxic cancer cells due to the presence of HIF-1. PDK1 shunts pyruvate away from the citric acid cycle and keeps the hypoxic cell alive. Therefore, PDK1 inhibition has been suggested as an antitumor therapy since PDK1 prevents apoptosis in these cancerous cells. Similarly, PDK3 has been shown to be overexpressed in colon cancer cell lines. Three proposed inhibitors are AZD7545 and Dichloroacetate which both bind to PDK1, and Radicicol which binds to PDK3.

II. COMPOUNDS OF THE PRESENT DISCLOSURE

Compounds of the present disclosure are provided as inhibitors of PDK1-4. In some aspects of the present invention, the present invention provides inhibitors of PDK1-4, which are compounds of the formula:

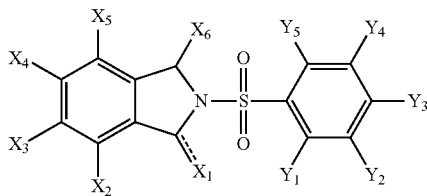
(I)

wherein: $X_1$ is hydrogen, halogen, hydroxy, amino, cyano, nitro, or oxo, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, —C(O)-alkoxy$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, amido$_{(C\leq12)}$, -arenediyl$_{(C\leq6)}$-heteroaryl$_{(C\leq12)}$, or a substituted version of any of these groups, or when is taken together with $X_6$, $X_1$ is as defined below; $X_2$, $X_3$, $X_4$, $X_5$ are each independently hydrogen, halogen, hydroxy, nitro, cyano, or amino, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylthio$_{(C\leq12)}$, alkenylthio$_{(C\leq12)}$, alkynylthio$_{(C\leq12)}$, arylthio$_{(C\leq18)}$, aralkylthio$_{(C\leq18)}$, heterocycloalkylthio$_{(C\leq12)}$, heteroarylthio$_{(C\leq12)}$, acylthio$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, amido$_{(C\leq12)}$, -alkanediyl$_{(C\leq6)}$-heterocycloalkyl$_{(C\leq12)}$, or a substituted version of any of these groups; or

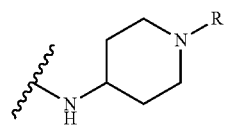

wherein: R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups; $X_6$ is hydrogen, halogen, hydroxy, amino, nitro, or cyano, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamine$_{(C\leq12)}$, dialkylamine$_{(C\leq12)}$, alkenylamine$_{(C\leq12)}$, alkynylamine$_{(C\leq12)}$, arylamine$_{(C\leq18)}$, aralkylamine$_{(C\leq18)}$, heterocycloalkylamine$_{(C\leq12)}$, heteroarylamine$_{(C\leq12)}$, or amido$_{(C\leq12)}$, or a substituted version of any of these groups, or when is taken together with $X_1$, $X_6$ is as defined below; $Y_1$, $Y_2$, $Y_3$, $Y_4$, and $Y_5$ are each independently hydrogen, amino, cyano, halo, hydroxy, or nitro, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, or a substituted version of any of these groups; $X_1$ and $X_6$ when taken together have the formula:

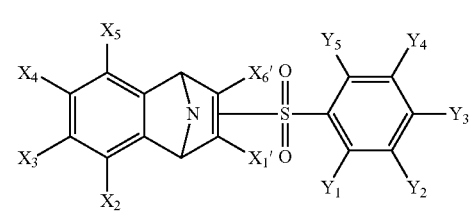
(II)

wherein: $X_1'$ and $X_6'$ are each independently hydrogen, hydroxy, halo, or amino; alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, acyl$_{(C\leq12)}$, or a substituted version of any of these groups; or a pharmaceutically acceptable salt thereof.

In some embodiments of the present invention, compounds of the present invention, compounds were at least one of $Y_1$, $Y_2$, $Y_3$, $Y_4$, or $Y_5$ are hydroxy or alkoxy$_{(C\leq12)}$ and $X_2$, $X_3$, $X_4$, and $X_5$ are not all hydrogen, or were $X_1$ is oxo and $X_6$ is not aryl$_{(C\leq8)}$ are specifically excluded. In other embodiments, compounds were $X_3$ and $X_4$ are methoxy and $Y_3$ is methyl or were $Y_1$ and $Y_3$ are hydroxy or methoxy and $X_1$, $X_2$, $X_3$, $X_4$, $X_5$, and $X_6$ are all hydrogen are specifically excluded. In some embodiments, the compound is further defined by the formula:

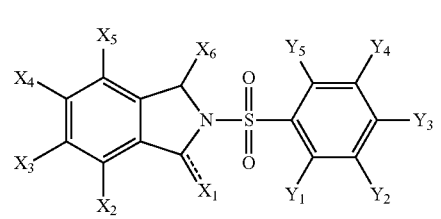
(I)

wherein: $X_1$ is hydrogen, hydroxy, amino, or oxo, or alkyl$_{(C\le 12)}$, alkenyl$_{(C\le 12)}$, alkynyl$_{(C\le 12)}$, aryl$_{(C\le 18)}$, aralkyl$_{(C\le 18)}$, heterocycloalkyl$_{(C\le 12)}$, heteroaryl$_{(C\le 12)}$, acyl$_{(C\le 12)}$, —C(O)-alkoxy$_{(C\le 12)}$, alkoxy$_{(C\le 12)}$, heterocycloalkoxy$_{(C\le 12)}$, alkylthio$_{(C\le 12)}$, heterocycloalkylthio$_{(C\le 12)}$, alkylamine$_{(C\le 12)}$, dialkylamine$_{(C\le 12)}$, heterocycloalkylamine$_{(C\le 12)}$, -alkanediyl$_{(C\le 6)}$-heterocycloalkyl$_{(C\le 12)}$, or a substituted version of any of these groups, or when is taken together with $X_6$, $X_1$ is as defined below; $X_2$, $X_3$, $X_4$, $X_5$ are each independently hydrogen, hydroxy, or amino, or alkyl$_{(C\le 12)}$, alkoxy$_{(C\le 12)}$, alkylamine$_{(C\le 12)}$, dialkylamine$_{(C\le 12)}$, heterocycloalkylamine$_{(C\le 12)}$, or a substituted version of any of these groups; or

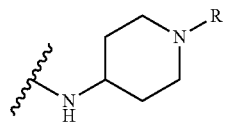

wherein: R is hydrogen; or alkyl$_{(C\le 12)}$, alkenyl$_{(C\le 12)}$, acyl$_{(C\le 12)}$, aryl$_{(C\le 12)}$, aralkyl$_{(C\le 12)}$, or a substituted version of any of these groups; $X_6$ is hydrogen, hydroxy, amino, or alkyl$_{(C\le 12)}$, alkenyl$_{(C\le 12)}$, alkynyl$_{(C\le 12)}$, aryl$_{(C\le 18)}$, aralkyl$_{(C\le 18)}$, heterocycloalkyl$_{(C\le 12)}$, heteroaryl$_{(C\le 12)}$, acyl$_{(C\le 12)}$, alkoxy$_{(C\le 12)}$, alkenyloxy$_{(C\le 12)}$, alkynyloxy$_{(C\le 12)}$, aryloxy$_{(C\le 18)}$, aralkyloxy$_{(C\le 18)}$, heterocycloalkyloxy$_{(C\le 12)}$, heteroaryloxy$_{(C\le 12)}$, acyloxy$_{(C\le 12)}$, alkylamine$_{(C\le 12)}$, dialkylamine$_{(C\le 12)}$, alkenylamine$_{(C\le 12)}$, alkynylamine$_{(C\le 12)}$, arylamine$_{(C\le 18)}$, aralkylamine$_{(C\le 18)}$, heterocycloalkylamine$_{(C\le 12)}$, heteroarylamine$_{(C\le 12)}$, or amido$_{(C\le 12)}$, or a substituted version of any of these groups, or when is taken together with $X_1$, $X_6$ is as defined below; $Y_1$, $Y_2$, $Y_3$, $Y_4$, and $Y_5$ are each independently hydrogen, amino, cyano, halo, hydroxy, or nitro, or alkyl$_{(C\le 12)}$, alkenyl$_{(C\le 12)}$, alkynyl$_{(C\le 12)}$, aryl$_{(C\le 12)}$, aralkyl$_{(C\le 12)}$, heteroaryl$_{(C\le 12)}$, heterocycloalkyl$_{(C\le 12)}$, acyl$_{(C\le 12)}$, or a substituted version of any of these groups; $X_1$ and $X_6$ when taken together have the formula:

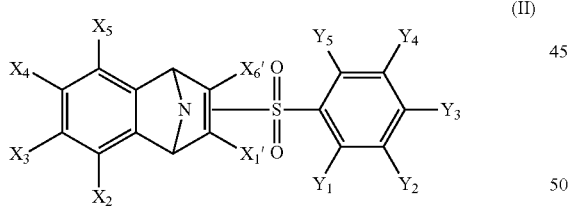

(II)

wherein: $X_1'$ and $X_6'$ are each independently hydrogen, hydroxy, halo, or amino; alkyl$_{(C\le 12)}$, alkenyl$_{(C\le 12)}$, alkynyl$_{(C\le 12)}$, aryl$_{(C\le 12)}$, aralkyl$_{(C\le 12)}$, heteroaryl$_{(C\le 12)}$, acyl$_{(C\le 12)}$, or a substituted version of any of these groups; or a pharmaceutically acceptable salt thereof.

In some embodiments, $X_1$ is hydrogen. In other embodiments, $X_1$ is oxo. In some embodiments, $X_2$ and $X_5$ are each independently hydrogen. In other embodiments, $X_2$ and $X_5$ are each independently hydroxy or alkoxy$_{(C\le 12)}$. In some embodiments, $X_2$ and $X_5$ are each independently methoxy. In some embodiments, $X_3$ and $X_4$ are each independently hydrogen. In other embodiments, $X_3$ and $X_4$ are each independently hydroxy or alkoxy$_{(C\le 12)}$. In some embodiments, $X_3$ and $X_4$ are each independently methoxy. In other embodiments, $X_3$ and $X_4$ are each independently amino, alkylamino$_{(C\le 12)}$, heterocycloalkylamino$_{(C\le 12)}$, substituted alkylamino$_{(C\le 12)}$, or substituted heterocycloalkylamino$_{(C\le 12)}$. In some embodiments, $X_3$ and $X_4$ are each independently amino,

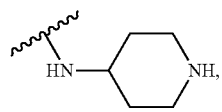

cyclohexylamine,

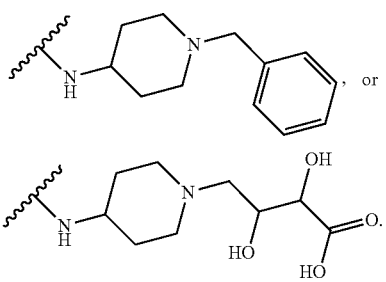

, or

In some embodiments, $X_6$ is hydrogen. In other embodiments, $X_6$ is alkyl$_{(C\le 12)}$, alkenyl$_{(C\le 12)}$, aryl$_{(C\le 12)}$, or a substituted version of any of these groups. In some embodiments, $Y_1$, $Y_2$, $Y_3$, $Y_4$, and $Y_5$ are each independently hydrogen. In other embodiments, $Y_1$, $Y_2$, $Y_3$, $Y_4$, and $Y_5$ are each independently halo, hydroxy, or alkoxy$_{(C\le 12)}$. In some embodiments, $Y_1$, $Y_2$, $Y_3$, $Y_4$, and $Y_5$ are each independently hydroxy. In some embodiments, $Y_1$, $Y_2$, $Y_3$, $Y_4$, and $Y_5$ are each independently methoxy. In some embodiments, $Y_1$ and $Y_3$ are both hydroxy or methoxy. In some aspects, the present invention provides the following compounds:

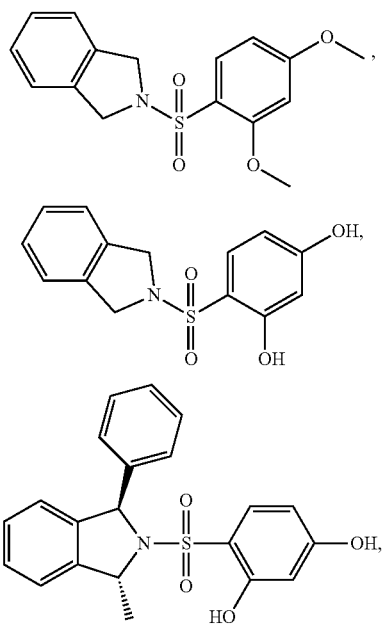

65
-continued
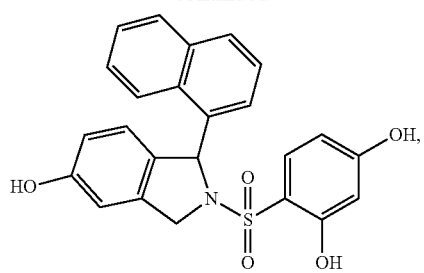
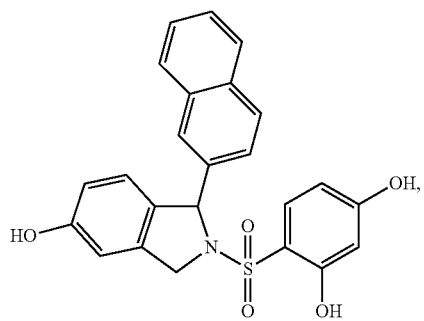
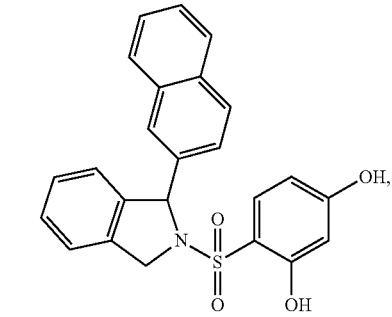
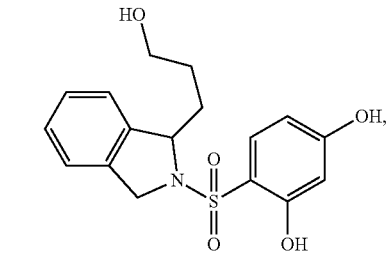
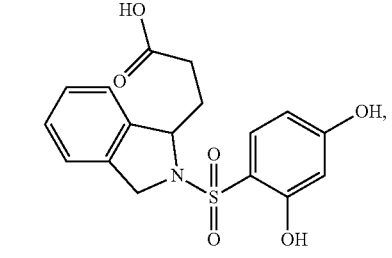
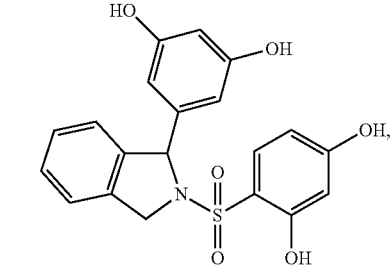
66
-continued
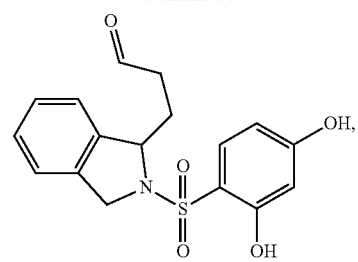
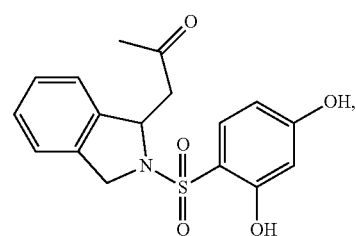
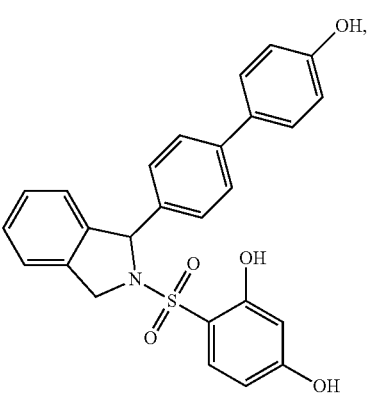
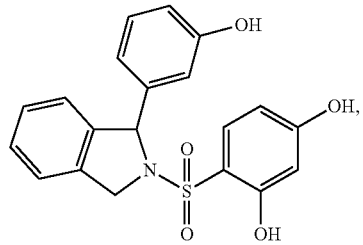
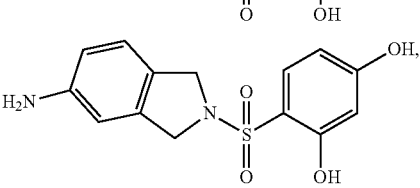

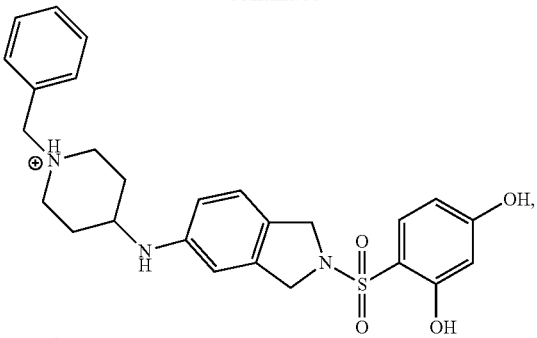

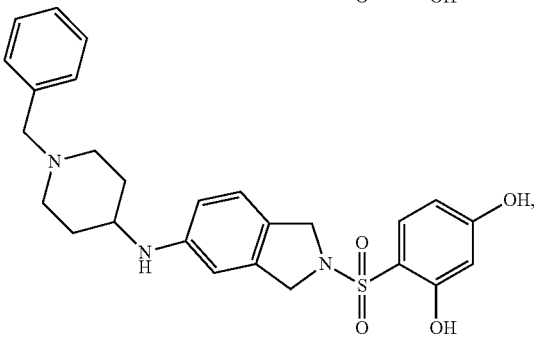

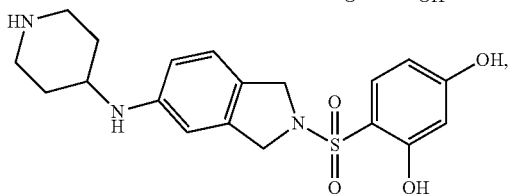

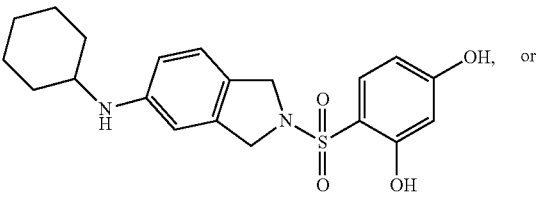

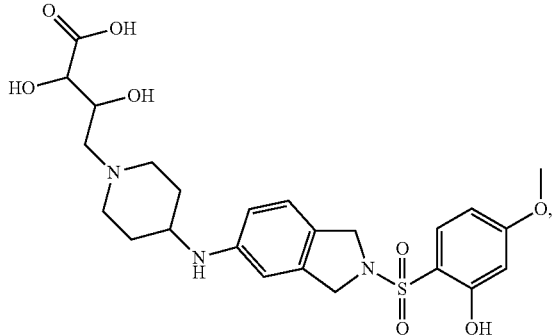 [SMILES: COc1ccc(S(=O)(=O)N2Cc3ccc(NC4CCN(CC(O)C(O)C(=O)O)CC4)cc3C2)c(O)c1]

or a pharmaceutically acceptable salt, thereof.

A. Chemical Definitions

When used in the context of a chemical group: "hydrogen" means H; "hydroxy" means OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the formula

includes

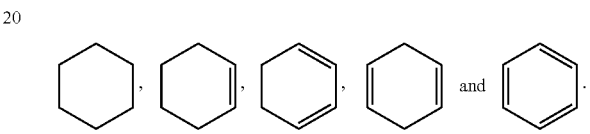

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol "〰", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◤" means a single bond where the group attached to the thick end of the wedge is "out of the page." The symbol "⫼" means a single bond where the group attached to the thick end of the wedge is "into the page". The symbol "〰" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper. Any undefined valency on an atom of a structure shown in this application implicitly represents a hydrogen atom bonded to the atom.

When a group "R" is depicted as a "floating group" on a ring system, for example, in the formula:

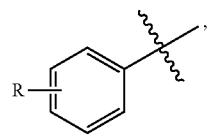

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

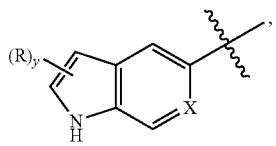

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$ (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)H, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to a monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHC$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

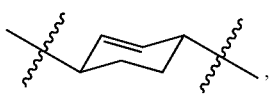

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)H, —C(O) CH$_3$, —N(CH$_3$)$_2$, —C(O)NH$_2$, —OC(O)CH$_3$, or S(O)$_2$ NH$_2$. The groups, —CH=CHF, —CH=CHCl and CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. The term "alkynediyl" when used without the "substituted" modifier refers to a divalent unsaturated aliphatic group, with two carbon atoms as points of attachment, a linear or branched, cyclo, cyclic or acyclic structure, at least one carbon-carbon triple bond, and no atoms other than carbon and hydrogen. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)H, —C(O)CH$_3$, —N(CH$_3$)$_2$, —C(O)NH$_2$, —OC(O)CH$_3$, or S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

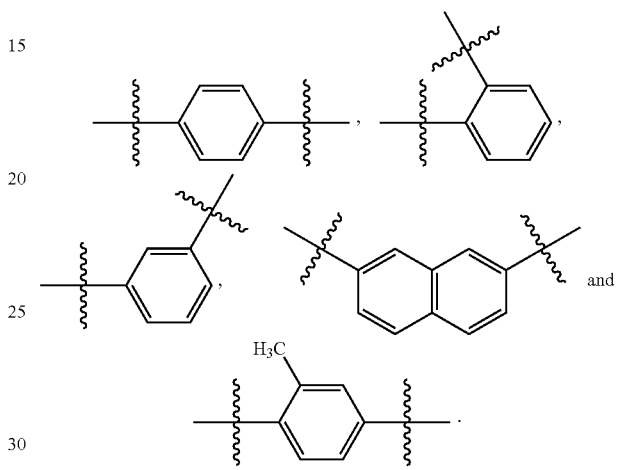

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) H, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group alkanediylaryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) H, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

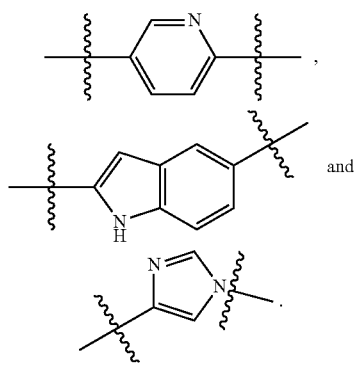

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) H, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl, heteroaryl, or heterocycloalkyl as those terms are defined above. The groups, —CHO, —C(O)CH$_3$ (acetyl, —Ac), —C(O)CH$_2$CH$_3$, —C(O)CH$_2$CH$_2$CH$_3$, —C(O)CH(CH$_3$)$_2$, —C(O)CH (CH$_2$)$_2$, —C(O)C$_6$H$_9$N, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)H, —C(O)CH$_3$, —N(CH$_3$)$_2$, —C(O)NH$_2$, —OC(O) CH$_3$, or S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and CON(CH$_3$)$_2$, are non-limiting examples of substituted acyl groups.

The term "alkoxy" when used without the "substituted" modifier refers to the group OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as OR, in which R is alkenyl, alkynyl, aryl, aralkyl, heteroaryl, and acyl, respectively. Similarly, the term "alkylthio" when used without the "substituted" modifier refers to the group SR, in which R is an alkyl, as that term is defined above. Analogously, the terms "alkenylthio", "alkynylthio", "arylthio", "aralkthio", "heteroarylthio", and "acylthio", when used without the "substituted" modifier, refers to groups, defined as SR, in which R is alkenyl, alkynyl, aryl, aralkyl, heteroaryl, and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)H, —C(O) CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) H, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O) NHCH$_3$ are non-limiting examples of substituted amido groups.

As used herein, a "chiral auxiliary" refers to a removable chiral group that is capable of influencing the stereoselectivity of a reaction. Persons of skill in the art are familiar with such compounds, and many are commercially available.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. "Isoxazole derivatives," therefore, refers to a chemically modified compound that still retains the desired effects of the parent isoxazole prior to its chemical modification. Such effects may be enhanced (e.g., slightly more effective, twice as effective, etc.) or diminished (e.g., slightly less effective, 2-fold less effective, etc.) relative to the parent isoxazole, but may still be considered an isoxazole derivative. Such derivatives may have the addition, removal, or substitution of one or more chemical moieties on the parent molecule. Non-limiting examples of the types modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Prodrugs and solvates of the compounds of the present invention are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present invention are preferably hydrates.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (2002), which is incorporated herein by reference.

As used herein, the term "cyclic group" refers to a carbocycle group (e.g., cyclopropyl, cyclohexyl), a heterocycle group (e.g., pyrrolidinyl), an aryl group, or any combination thereof (e.g., fused bicyclic group).

As used herein, "protecting group" refers to a moiety attached to a functional group to prevent an otherwise unwanted reaction of that functional group. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts (1999). Compounds of the present invention are specifically contemplated wherein one or more functional groups are protected by a protecting group.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers.

Solvent choices for the synthetic preparation of compounds of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention. One of ordinary skill in the art will understand that compounds of the present invention can generally be purified at any step, including the purification of intermediates as well as purification of the final products. In particular embodiments, purification is performed via silica gel column chromatography or HPLC.

In view of the above definitions, other chemical terms used throughout this application can be easily understood by those of skill in the art. Terms may be used alone or in any combination thereof. The preferred and more preferred chain lengths of the radicals apply to all such combination.

B. Generic Structures and Specific Compounds

In some aspects of the present invention, the invention provides a compound of the formula:

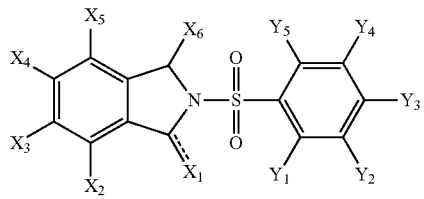
(I)

wherein: $X_1$ is hydrogen, halogen, hydroxy, amino, cyano, nitro, or oxo, or $alkyl_{(C \leq 12)}$, $alkenyl_{(C \leq 12)}$, $alkynyl_{(C \leq 12)}$, $aryl_{(C \leq 18)}$, $aralkyl_{(C \leq 18)}$, $heterocycloalkyl_{(C \leq 12)}$, $heteroaryl_{(C \leq 12)}$, $acyl_{(C \leq 12)}$, $alkoxy_{(C \leq 12)}$, $alkenyloxy_{(C \leq 12)}$, $alkynyloxy_{(C \leq 12)}$, $aryloxy_{(C \leq 18)}$, $aralkyloxy_{(C \leq 18)}$, $heterocycloalkyloxy_{(C \leq 12)}$, $heteroaryloxy_{(C \leq 12)}$, $acyloxy_{(C \leq 12)}$, —C(O)-$alkoxy_{(C \leq 12)}$, $alkylamine_{(C \leq 12)}$, $dialkylamine_{(C \leq 12)}$, $alkenylamine_{(C \leq 12)}$, $alkynylamine_{(C \leq 12)}$, $arylamine_{(C \leq 18)}$, $aralkylamine_{(C \leq 18)}$, $heterocycloalkylamine_{(C \leq 12)}$, $heteroarylamine_{(C \leq 12)}$, $amido_{(C \leq 12)}$, $arenediyl_{(C \leq 6)}$-$heteroaryl_{(C \leq 12)}$, or a substituted version of any of these groups, or is taken together with $X_6$ as defined below; $X_2$, $X_3$, $X_4$, $X_5$ are each independently hydrogen, halogen, hydroxy, nitro, cyano, or amino, or $alkyl_{(C \leq 12)}$, $alkenyl_{(C \leq 12)}$, $alkynyl_{(C \leq 12)}$, $aryl_{(C \leq 18)}$, $aralkyl_{(C \leq 18)}$, $heterocycloalkyl_{(C \leq 12)}$, $heteroaryl_{(C \leq 12)}$, $acyl_{(C \leq 12)}$, $alkoxy_{(C \leq 12)}$, $alkenyloxy_{(C \leq 12)}$, $alkynyloxy_{(C \leq 12)}$, $aryloxy_{(C \leq 18)}$, $aralkyloxy_{(C \leq 18)}$, $heterocycloalkyloxy_{(C \leq 12)}$, $heteroaryloxy_{(C \leq 12)}$, $acyloxy_{(C \leq 12)}$, $alkylthio_{(C \leq 12)}$, $alkenylthio_{(C \leq 12)}$, $alkynylthio_{(C \leq 12)}$, $arylthio_{(C \leq 18)}$, $aralkylthio_{(C \leq 18)}$, $heterocycloalkylthio_{(C \leq 12)}$, $heteroarylthio_{(C \leq 12)}$, $acylthio_{(C \leq 12)}$, $alkylamine_{(C \leq 12)}$, $dialkylamine_{(C \leq 12)}$, $alkenylamine_{(C \leq 12)}$, $alkynylamine_{(C \leq 12)}$, $arylamine_{(C \leq 18)}$, $aralkylamine_{(C \leq 18)}$, $heterocycloalkylamine_{(C \leq 12)}$, $heteroarylamine_{(C \leq 12)}$, $amido_{(C \leq 12)}$, -alkanediyl$_{(C \leq 6)}$-$heterocycloalkyl_{(C \leq 12)}$, or a substituted version of any of these groups; or

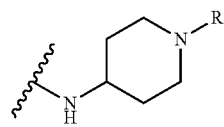

wherein: R is hydrogen; or $alkyl_{(C \leq 12)}$, $alkenyl_{(C \leq 12)}$, $acyl_{(C \leq 12)}$, $aryl_{(C \leq 12)}$, $aralkyl_{(C \leq 12)}$, or a substituted version of any of these groups; $X_6$ is hydrogen, halogen, hydroxy, amino, nitro, or cyano, or $alkyl_{(C \leq 12)}$, $alkenyl_{(C \leq 12)}$, $alkynyl_{(C \leq 12)}$, $aryl_{(C \leq 18)}$, $aralkyl_{(C \leq 18)}$, $heterocycloalkyl_{(C \leq 12)}$, $heteroaryl_{(C \leq 12)}$, $acyl_{(C \leq 12)}$, $alkoxy_{(C \leq 12)}$, $alkenyloxy_{(C \leq 12)}$, $alkynyloxy_{(C \leq 12)}$, $aryloxy_{(C \leq 18)}$, $aralkyloxy_{(C \leq 18)}$, $heterocycloalkyloxy_{(C \leq 12)}$, $heteroaryloxy_{(C \leq 12)}$, $acyloxy_{(C \leq 12)}$, $alkylamine_{(C \leq 12)}$, $dialkylamine_{(C \leq 12)}$, $alkenylamine_{(C \leq 12)}$, $alkynylamine_{(C \leq 12)}$, $arylamine_{(C \leq 18)}$, $aralkylamine_{(C \leq 18)}$, $heterocycloalkylamine_{(C \leq 12)}$, $heteroarylamine_{(C \leq 12)}$, or $amido_{(C \leq 12)}$, or a substituted version of any of these groups, or is taken together with $X_1$ as defined below; $Y_1$, $Y_2$, $Y_3$, $Y_4$, and $Y_5$ are each independently hydrogen, amino, cyano, halo, hydroxy, or nitro, or $alkyl_{(C \leq 12)}$, $alkenyl_{(C \leq 12)}$, $alkynyl_{(C \leq 12)}$, $aryl_{(C \leq 12)}$, $aralkyl_{(C \leq 12)}$, $heteroaryl_{(C \leq 12)}$, $heterocycloalkyl_{(C \leq 12)}$, $acyl_{(C \leq 12)}$, or a substituted version of any of these groups; $X_1$ and $X_6$ when taken together have the formula:

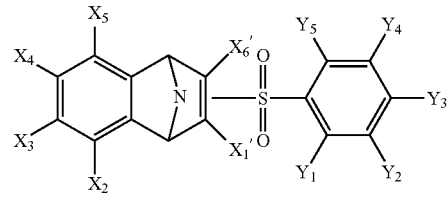
(II)

wherein: $X_1'$ and $X_6'$ are each independently hydrogen, hydroxy, halo, or amino; $alkyl_{(C \leq 12)}$, $alkenyl_{(C \leq 12)}$, $alkynyl_{(C \leq 12)}$, $aryl_{(C \leq 12)}$, $aralkyl_{(C \leq 12)}$, $heteroaryl_{(C \leq 12)}$, $acyl_{(C \leq 12)}$, or a substituted version of any of these groups; provided that at least one of $Y_1$, $Y_2$, $Y_3$, $Y_4$, or $Y_5$ are hydroxy or $alkoxy_{(C \leq 12)}$ and that $X_2$, $X_3$, $X_4$, and $X_5$ are not all hydrogen, or that when $X_1$ is oxo then $X_6$ is not $aryl_{(C \leq 8)}$; or a pharmaceutically acceptable salt thereof. In some embodiments, the compound is further defined by the formula:

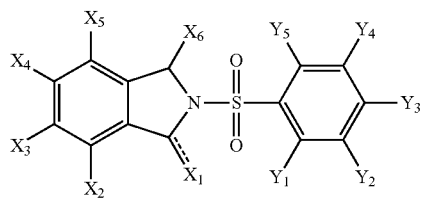
(I)

wherein: $X_1$ is hydrogen, hydroxy, amino, or oxo, or $alkyl_{(C \leq 12)}$, $alkenyl_{(C \leq 12)}$, $alkynyl_{(C \leq 12)}$, $aryl_{(C \leq 18)}$, $aralkyl_{(C \leq 18)}$, $heterocycloalkyl_{(C \leq 12)}$, $heteroaryl_{(C \leq 12)}$, $acyl_{(C \leq 12)}$, $alkoxy_{(C \leq 12)}$, —C(O)-$alkoxy_{(C \leq 12)}$, $alkylamine_{(C \leq 12)}$, $dialkylamine_{(C \leq 12)}$, -$arenediyl_{(C \leq 6)}$-$heteroaryl_{(C \leq 12)}$, or a substituted version of any of these groups, or is taken together with $X_6$ as defined below; $X_2$, $X_3$, $X_4$, $X_5$ are each independently hydrogen, hydroxy, or amino, or alkyl$_{(C≤12)}$, alkoxy$_{(C≤12)}$, heterocycloalkoxy$_{(C≤12)}$, alkylthio$_{(C≤12)}$, heterocycloalkylthio$_{(C≤12)}$, alkylamine$_{(C≤12)}$, dialkylamine$_{(C≤12)}$, heterocycloalkylamine$_{(C≤12)}$, -alkanediyl$_{(C≤6)}$-heterocycloalkyl$_{(C≤12)}$, or a substituted version of any of these groups; or

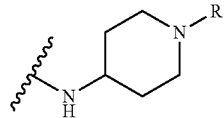

wherein: R is hydrogen; or alkyl$_{(C≤12)}$, alkenyl$_{(C≤12)}$, acyl$_{(C≤12)}$, aryl$_{(C≤12)}$, aralkyl$_{(C≤12)}$, or a substituted version of any of these groups; $X_6$ is hydrogen, hydroxy, amino, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylamine$_{(C≤12)}$, dialkylamine$_{(C≤12)}$, alkenylamine$_{(C≤12)}$, alkynylamine$_{(C≤12)}$, arylamine$_{(C≤18)}$, aralkylamine$_{(C≤18)}$, heterocycloalkylamine$_{(C≤12)}$, heteroarylamine$_{(C≤12)}$, or amido$_{(C≤12)}$, or a substituted version of any of these groups, or is taken together with $X_1$ as defined below; $Y_1$, $Y_2$, $Y_3$, $Y_4$, and $Y_5$ are each independently hydrogen, amino, cyano, halo, hydroxy, or nitro, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, or a substituted version of any of these groups; $X_1$ and $X_6$ when taken together have the formula:

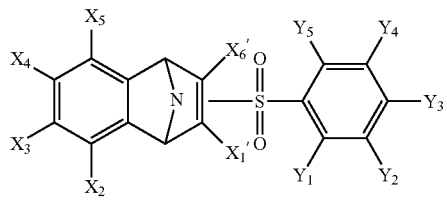

(II)

wherein: $X_1'$ and $X_6'$ are each independently hydrogen, hydroxy, halo, or amino; alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, acyl$_{(C≤12)}$, or a substituted version of any of these groups; provided that at least one of $Y_1$, $Y_2$, $Y_3$, $Y_4$, or $Y_5$ are hydroxy or alkoxy$_{(C≤12)}$ and that $X_2$, $X_3$, $X_4$, and $X_5$ are not all hydrogen, or that when $X_1$ is oxo then $X_6$ is not aryl$_{(C≤8)}$; or a pharmaceutically acceptable salt thereof. In some embodiments, $X_1$ is hydrogen. In other embodiments, $X_1$ is oxo. In some embodiments, $X_2$ and $X_5$ are each independently hydrogen. In other embodiments, $X_2$ and $X_5$ are each independently hydroxy or alkoxy$_{(C≤12)}$. In other embodiments, $X_2$ and $X_5$ are each independently methoxy. In some embodiments, $X_3$ and $X_4$ are each independently hydrogen. In other embodiments, $X_3$ and $X_4$ are each independently hydroxy or alkoxy$_{(C≤12)}$. In other embodiments, $X_3$ and $X_4$ are each independently methoxy. In other embodiments, $X_3$ and $X_4$ are each independently amino, alkylamino$_{(C≤12)}$, heterocycloalkylamino$_{(C≤12)}$, substituted alkylamino$_{(C≤12)}$, or substituted heterocycloalkylamino$_{(C≤12)}$. In other embodiments, $X_3$ and $X_4$ are each independently amino, cyclohexylamine,

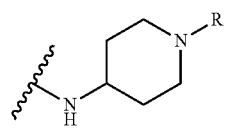

wherein: R is hydrogen; or alkyl$_{(C≤12)}$, alkenyl$_{(C≤12)}$, acyl$_{(C≤12)}$, aryl$_{(C≤12)}$, aralkyl$_{(C≤12)}$, or a substituted version of any of these groups. In some embodiments, $X_6$ is hydrogen. In other embodiments, $X_6$ is alkyl$_{(C≤12)}$, alkenyl$_{(C≤12)}$, aryl$_{(C≤12)}$, or a substituted version of any of these groups. In some embodiments, $Y_1$, $Y_2$, $Y_3$, $Y_4$, and $Y_5$ are each independently hydrogen. In other embodiments, $Y_1$, $Y_2$, $Y_3$, $Y_4$, and $Y_5$ are each independently halo, hydroxy, or alkoxy$_{(C≤12)}$. In some embodiments, $Y_1$, $Y_2$, $Y_3$, $Y_4$, and $Y_5$ are each independently hydroxy. In other embodiments, $Y_1$, $Y_2$, $Y_3$, $Y_4$, and $Y_5$ are each independently methoxy. In other embodiments, $Y_1$ and $Y_3$ are both hydroxy or methoxy.

In some aspects, the present invention relates to the compounds defined as:

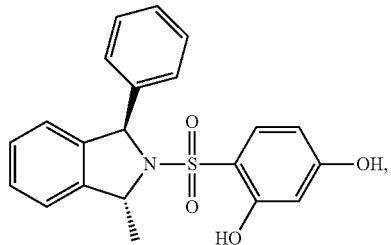

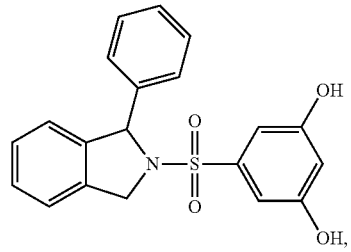

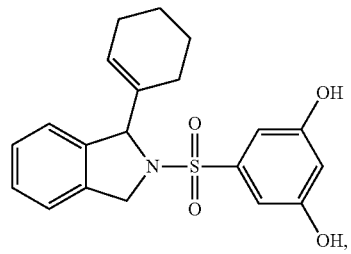

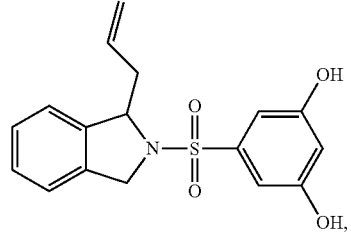

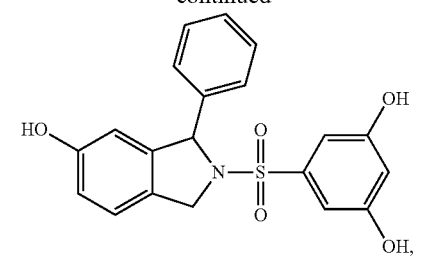
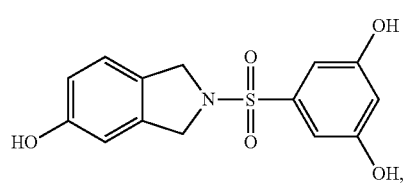
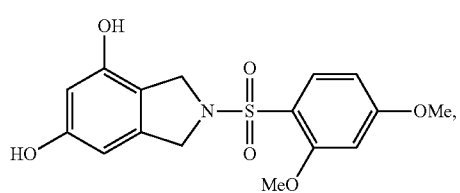
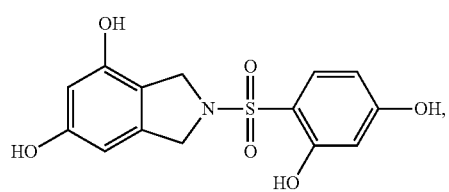
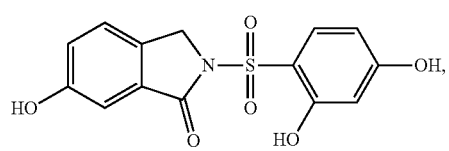
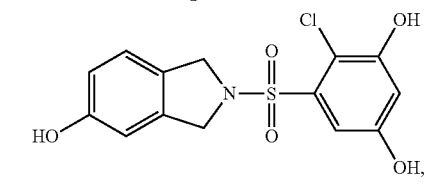
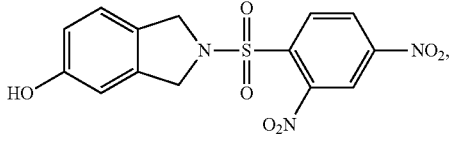
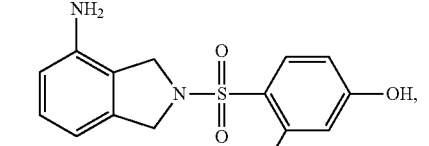
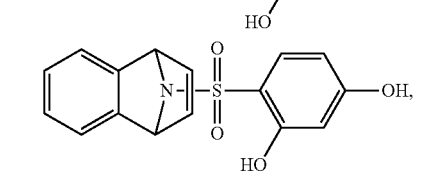
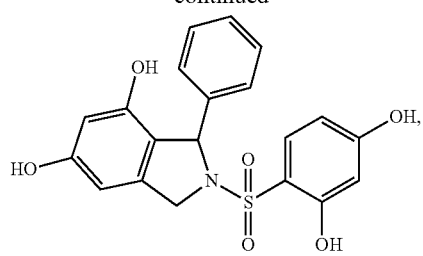
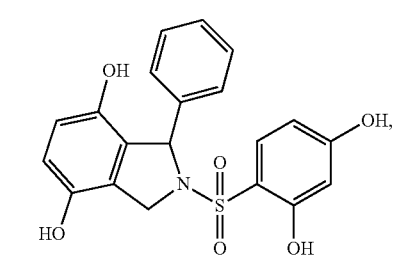
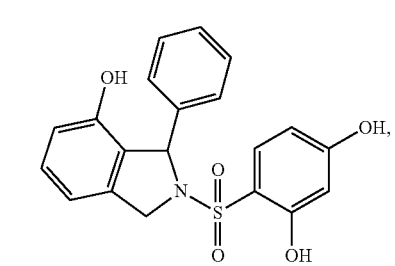
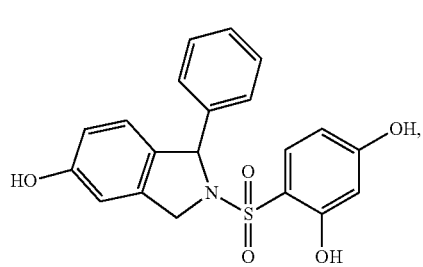
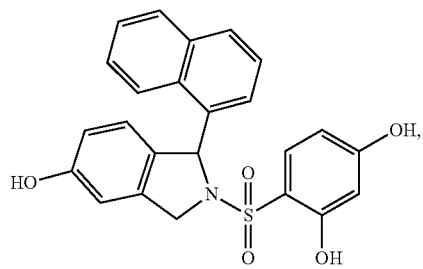
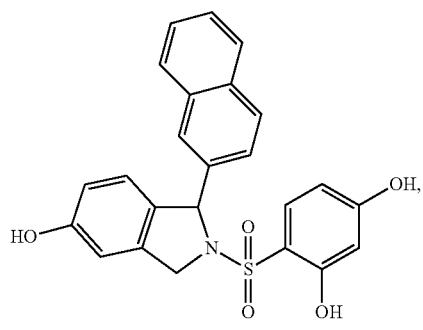

83
-continued
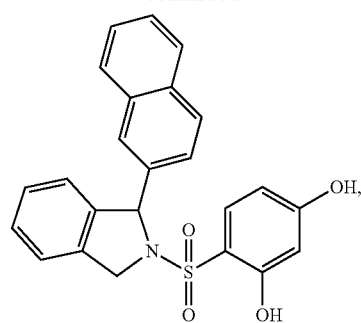
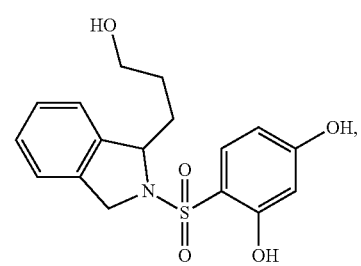
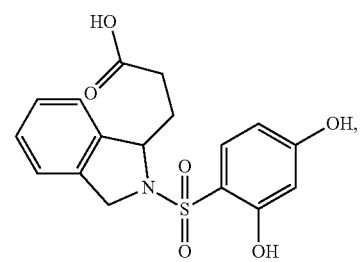
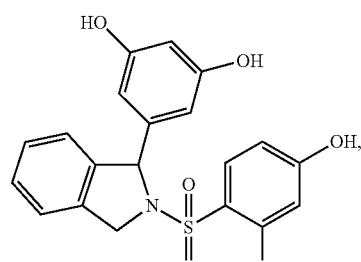
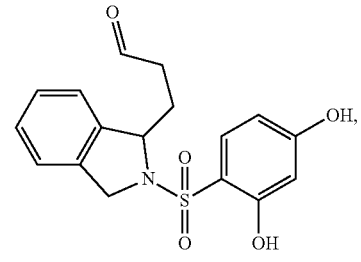
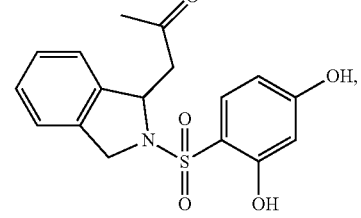
84
-continued
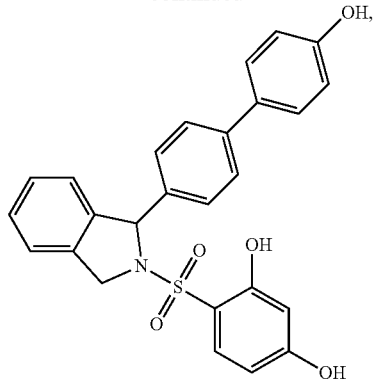
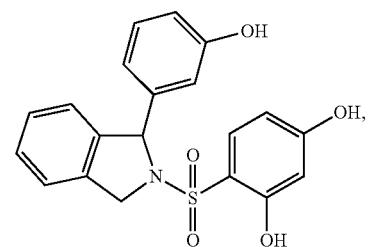
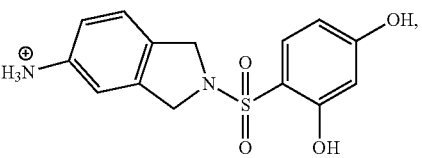
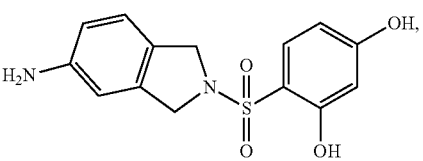
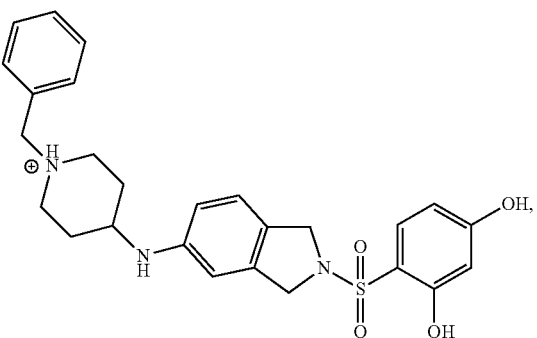
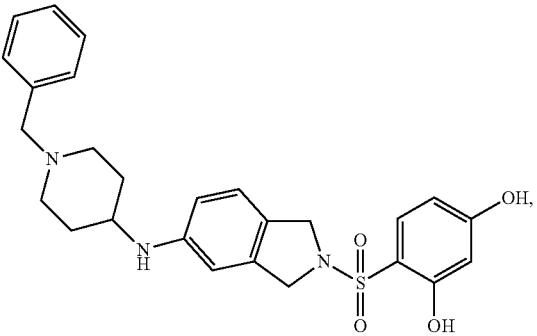

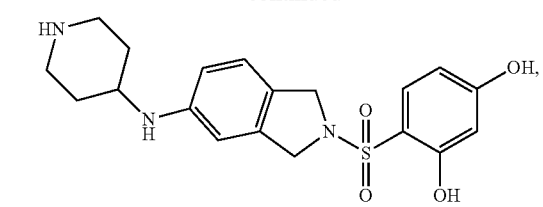
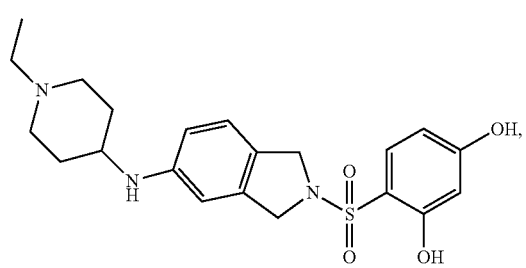
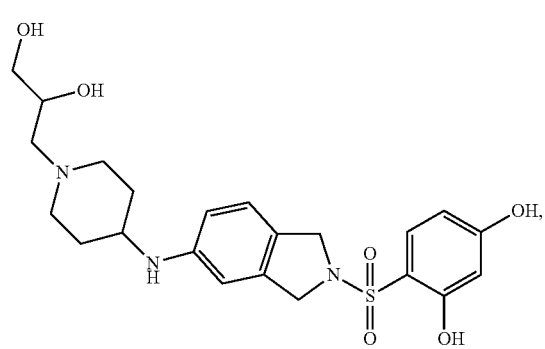
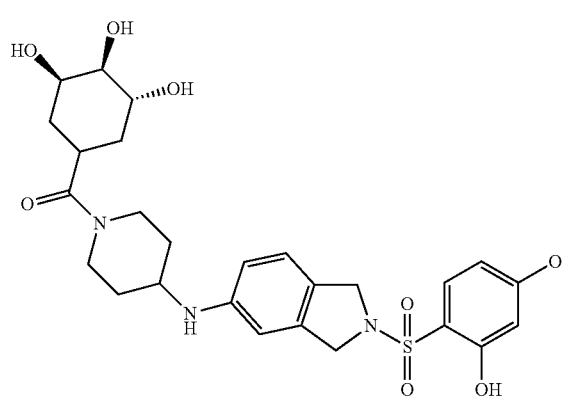
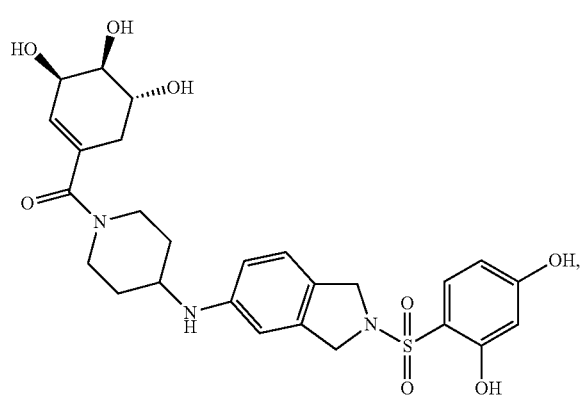
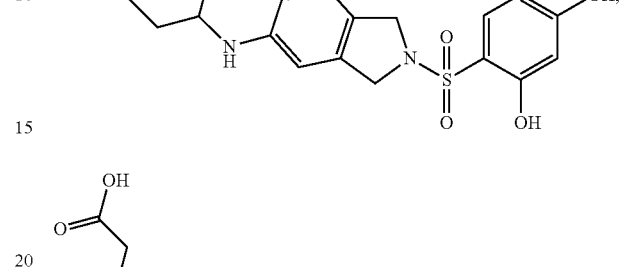
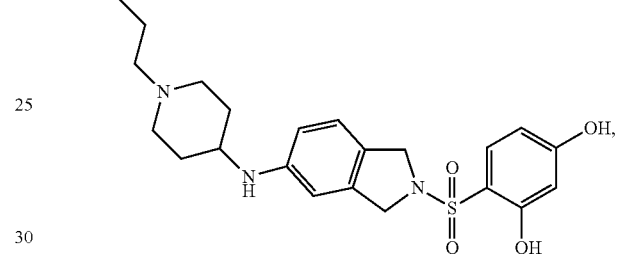
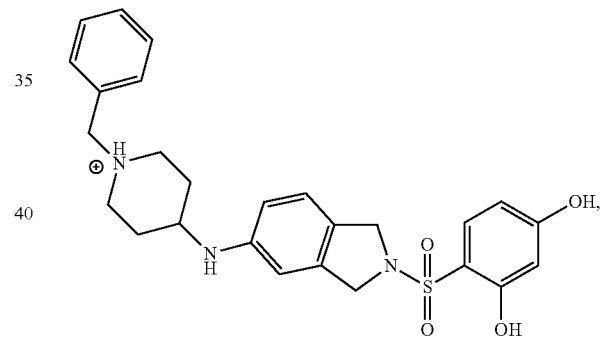
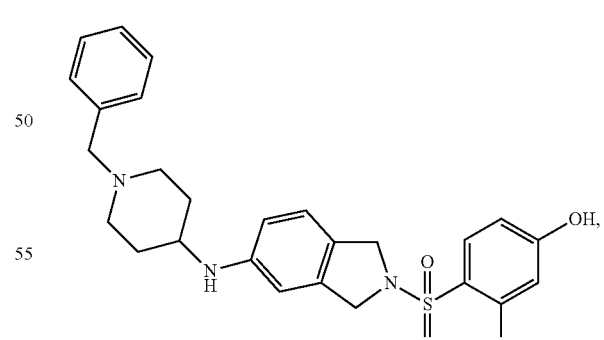
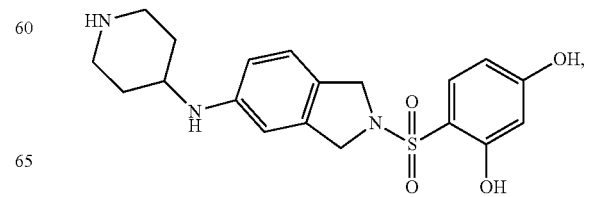

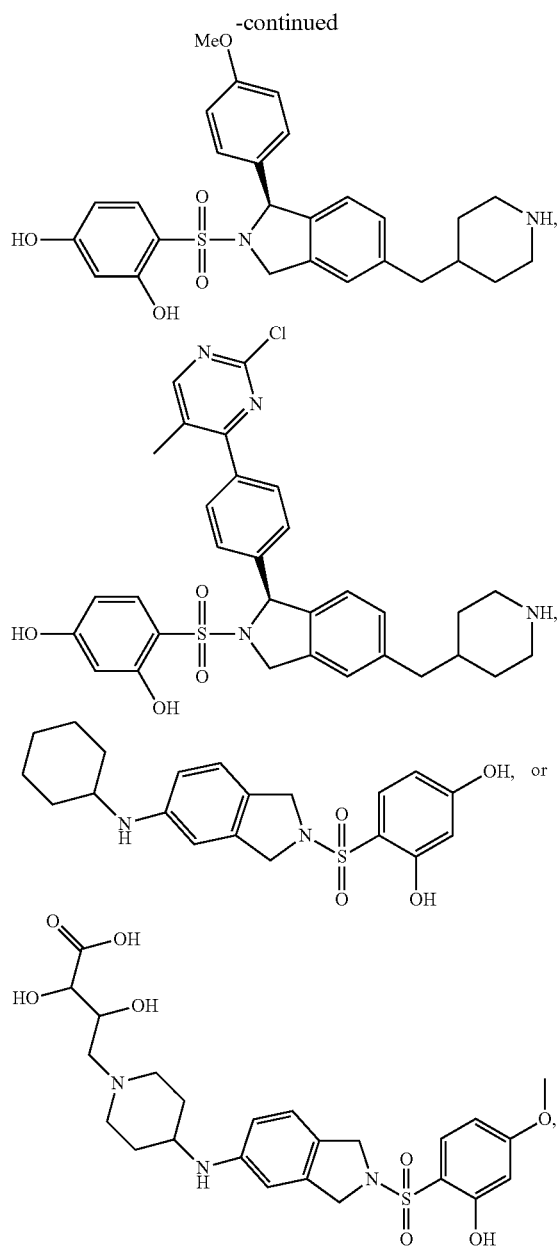

or a pharmaceutically acceptable salt, thereof.

III. DISEASE STATES

A. Diabetes

Diabetes mellitus, often simply referred to as diabetes, is a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger).

There are three main types of diabetes:

Type 1 diabetes: results from the body's failure to produce insulin, and presently requires the person to inject insulin. (Also referred to as insulin-dependent diabetes mellitus, IDDM for short, and juvenile diabetes.)

Type 2 diabetes: results from insulin resistance, a condition in which cells fail to use insulin properly, and eventually combines with an absolute insulin deficiency. (Formerly referred to as non-insulin-dependent diabetes mellitus, NIDDM for short, and adult-onset diabetes.)

Gestational diabetes: is when pregnant women, who have never had diabetes before, have a high blood glucose level during pregnancy. It may precede development of type 2 diabetes mellitus.

Other forms of diabetes mellitus include congenital diabetes, which is due to genetic defects of insulin secretion, cystic fibrosis-related diabetes, steroid diabetes induced by high doses of glucocorticoids, and several forms of monogenic diabetes.

All forms of diabetes have been treatable since insulin became available in 1921, and type 2 diabetes may be controlled with medications. Both type 1 and 2 are chronic conditions that usually cannot be cured. Pancreas transplants have been tried with limited success in type 1 diabetes; gastric bypass surgery has been successful in many with morbid obesity and type 2 diabetes. Gestational diabetes usually resolves after delivery. Diabetes without proper treatments can cause many complications. Acute complications include hypoglycemia, diabetic ketoacidosis, or non-ketotic hyperosmolar coma. Serious long-term complications include cardiovascular disease, chronic renal failure, retinal damage. Adequate treatment of diabetes is thus important, as well as blood pressure control and lifestyle factors such as smoking cessation and maintaining a healthy body weight.

Diabetes is a huge health burden, costing an estimated $174 billion in 2007. In the United States alone more than 23 million people, ~8% of the population are diabetic; an additional 32% of adults are at risk with pre-diabetes, either impaired oral glucose tolerance or abnormally high fasting glucose (NIDDK, ADA statistics). This adds up to a staggeringly large proportion of the U.S. adult population with abnormal glucose metabolism. Worldwide, 230 million are affected by diabetes and the number is expected to double over the next 20 years. Currently, type 1 diabetes accounts for only 5% of the total. As obesity has become epidemic, type 2 diabetes has increased at an alarming rate. In spite of these daunting numbers, statistics also reveal that interventions that improve glycemic control reduce negative health consequences.

Most cases of diabetes mellitus fall into three broad categories: type 1, type 2, and gestational diabetes. A few other types are described. The term diabetes, without qualification, usually refers to diabetes mellitus. The rare disease diabetes insipidus has similar symptoms as diabetes mellitus, but without disturbances in the sugar metabolism.

The term "type 1 diabetes" has replaced several former terms, including childhood-onset diabetes, juvenile diabetes, and insulin-dependent diabetes mellitus (IDDM). Likewise, the term "type 2 diabetes" has replaced several former terms, including adult-onset diabetes, obesity-related diabetes, and non-insulin-dependent diabetes mellitus (NIDDM). Beyond these two types, there is no agreed-upon standard nomenclature. Various sources have defined "type 3 diabetes" as: gestational diabetes, insulin-resistant type 1 diabetes (or "double diabetes"), type 2 diabetes which has progressed to require injected insulin, and latent autoimmune diabetes of adults (or LADA or "type 1.5" diabetes).

Type 1 diabetes mellitus is characterized by loss of the insulin-producing beta cells of the islets of Langerhans in the pancreas leading to insulin deficiency. This type of diabetes can be further classified as immune-mediated or idiopathic. The majority of type 1 diabetes is of the immune-mediated nature, where β-cell loss is a T-cell mediated autoimmune attack. There is no known preventive measure against type 1 diabetes, which causes approximately 10% of diabetes mellitus cases in North America and Europe. Most affected people are otherwise healthy and of a healthy weight when onset occurs. Sensitivity and responsiveness to insulin are usually normal, especially in the early stages. Type 1 diabetes can affect children or adults but was traditionally termed "juvenile diabetes" because it represents a majority of the diabetes cases in children.

Type 2 diabetes mellitus is characterized by insulin resistance, which may be combined with relatively reduced insulin secretion. The defective responsiveness of body tissues to insulin has an array of possible causes with obesity as a major factor. Diabetes mellitus occurrences linked to single gene mutations are known as maturity onset diabetes of the young or MODY and are classified separately. Type 2 diabetes is the most common type.

In the early stage of type 2 diabetes, the predominant abnormality is reduced insulin sensitivity. At this stage hyperglycemia can be reversed by a variety of measures and medications that improve insulin sensitivity or reduce glucose production by the liver.

Gestational diabetes mellitus (GDM) resembles type 2 diabetes in several respects, involving a combination of relatively inadequate insulin secretion and responsiveness. It occurs in about 2%-5% of all pregnancies and may improve or disappear after delivery. Gestational diabetes is fully treatable but requires careful medical supervision throughout the pregnancy. About 20%-50% of affected women develop type 2 diabetes later in life.

Even though it may be transient, untreated gestational diabetes can damage the health of the fetus or mother. Risks to the baby include macrosomia (high birth weight), congenital cardiac and central nervous system anomalies, and skeletal muscle malformations. Increased fetal insulin may inhibit fetal surfactant production and cause respiratory distress syndrome. Hyperbilirubinemia may result from red blood cell destruction. In severe cases, perinatal death may occur, most commonly as a result of poor placental perfusion due to vascular impairment. Labor induction may be indicated with decreased placental function. A cesarean section may be performed if there is marked fetal distress or an increased risk of injury associated with macrosomia, such as shoulder dystocia.

Some cases of diabetes are caused by the body's tissue receptors not responding to insulin (even when insulin levels are normal, which is what separates it from type 2 diabetes); this form is very uncommon Genetic mutations (autosomal or mitochondrial) can lead to defects in beta cell function. Abnormal insulin action may also have been genetically determined in some cases. Any disease that causes extensive damage to the pancreas may lead to diabetes (for example, chronic pancreatitis and cystic fibrosis). Diseases associated with excessive secretion of insulin-antagonistic hormones can cause diabetes (which is typically resolved once the hormone excess is removed). Many drugs impair insulin secretion and some toxins damage pancreatic β-cells. The ICD-10 (1992) diagnostic entity, malnutrition-related diabetes mellitus (MRDM or MMDM, ICD-10 code E12), was deprecated by the World Health Organization when the current taxonomy was introduced in 1999.

B. Cancer

Cancer, known medically as a malignant neoplasm, is a broad group of diseases involving unregulated cell growth. In cancer, cells divide and grow uncontrollably, forming malignant tumors, and invading nearby parts of the body. The cancer may also spread to more distant parts of the body through the lymphatic system or bloodstream. Not all tumors are cancerous; benign tumors do not invade neighboring tissues and do not spread throughout the body. There are over 200 different known cancers that affect humans.

The causes of cancer are diverse, complex, and only partially understood. Many things are known to increase the risk of cancer, including tobacco use, dietary factors, certain infections, exposure to radiation, lack of physical activity, obesity, and environmental pollutants. These factors can directly damage genes or combine with existing genetic faults within cells to cause cancerous mutations. Approximately 5-10% of cancers can be traced directly to inherited genetic defects. Many cancers could be prevented by not smoking, eating more vegetables, fruits and whole grains, eating less meat and refined carbohydrates, maintaining a healthy weight, exercising, minimizing sunlight exposure, and being vaccinated against some infectious diseases.

Cancer can be detected in a number of ways, including the presence of certain signs and symptoms, screening tests, or medical imaging. Once a possible cancer is detected it is diagnosed by microscopic examination of a tissue sample. Cancer is usually treated with chemotherapy, radiation therapy and surgery. The chances of surviving the disease vary greatly by the type and location of the cancer and the extent of disease at the start of treatment. While cancer can affect people of all ages, and a few types of cancer are more common in children, the risk of developing cancer generally increases with age. In 2007, cancer caused about 13% of all human deaths worldwide (7.9 million). Rates are rising as more people live to an old age and as mass lifestyle changes occur in the developing world.

The present disclosure thus addresses, in another embodiment, the treatment of cancer. The types of cancer that may be treated are only limited by the involvement of impaired glucose oxidation, i.e., the Warburg effect in tumor cells. Thus, a wide variety of tumors are contemplated as being treatable including cancers of the brain, lung, liver, spleen, kidney, lymph node, pancreas, small intestine, blood cells, colon, stomach, breast, endometrium, prostate, testicle, cervix, uterus, rectum, eye, ovary, skin, head and neck, esophagus, bone marrow, blood or other tissue.

C. Heart Disease

Heart failure is one of the leading causes of morbidity and mortality in the world. In the U.S. alone, estimates indicate that 3 million people are currently living with cardiomyopathy and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals. Although there are other causes of DCM, familiar dilated cardiomyopathy has been indicated as representing approximately 20% of "idiopathic" DCM. Approximately half of the DCM cases are idiopathic, with the remainder being associated with known disease processes. For example, serious myocardial damage can result from certain drugs used in cancer chemotherapy (e.g., doxorubicin and daunoribucin). In addition, many DCM patients are chronic alcoholics. Fortunately, for these patients, the progression of myocardial dysfunction may be stopped or reversed if alcohol consumption is reduced or stopped early in the course of disease. Peripartum cardiomyopathy is another idiopathic form of DCM, as is disease associated with infectious sequelae. In sum, cardiomyopathies, including DCM, are significant public health problems.

As cardiomyopathy itself typically does not produce any symptoms until the cardiac damage is severe enough to produce heart failure, the symptoms of cardiomyopathy are those associated with heart failure. These symptoms include shortness of breath, fatigue with exertion, the inability to lie flat without becoming short of breath (orthopnea), paroxysmal nocturnal dyspnea, enlarged cardiac dimensions, and/or swelling in the lower legs. Patients also often present with increased blood pressure, extra heart sounds, cardiac murmurs, pulmonary and systemic emboli, chest pain, pulmonary congestion, and palpitations. In addition, DCM causes decreased ejection fractions (i.e., a measure of both intrinsic systolic function and remodeling). The disease is further characterized by ventricular dilation and grossly impaired systolic function due to diminished myocardial contractility, which results in dilated heart failure in many patients. Affected hearts also undergo cell/chamber remodeling as a result of the myocyte/myocardial dysfunction, which contributes to the "DCM phenotype." As the disease progresses, the symptoms progress as well. Patients with dilated cardiomyopathy also have a greatly increased incidence of life-threatening arrhythmias, including ventricular tachycardia and ventricular fibrillation. In these patients, an episode of syncope (dizziness) is regarded as a harbinger of sudden death.

Diagnosis of dilated cardiomyopathy typically depends upon the demonstration of enlarged heart chambers, particularly enlarged ventricles. Enlargement is commonly observable on chest X-rays, but is more accurately assessed using echocardiograms. DCM is often difficult to distinguish from acute myocarditis, valvular heart disease, coronary artery disease, and hypertensive heart disease. Once the diagnosis of dilated cardiomyopathy is made, every effort is made to identify and treat potentially reversible causes and prevent further heart damage. For example, coronary artery disease and valvular heart disease must be ruled out. Anemia, abnormal tachycardias, nutritional deficiencies, alcoholism, thyroid disease and/or other problems need to be addressed and controlled.

During attempts to identify and stabilize the underlying cause of the cardiomyopathy, treatment is generally instituted in order to minimize the symptoms and optimize the efficiency of the failing heart. Medication remains the mainstay of treatment, although there are no specific treatments for dilated cardiomyopathy other than those used in heart failure cases in general. Transplant surgery is one option. Indeed, dilated cardiomyopathy has been indicated as the most common cause for cardiac transplantation in the United States.

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

Treatment with pharmacological agents represents the primary mechanism for reducing or eliminating the manifestations of heart failure. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure.

If diuretics are ineffective, vasodilatory agents may be used; the angiotensin converting (ACE) inhibitors (e.g., enalopril and lisinopril) not only provide symptomatic relief, they also have been reported to decrease mortality. Again, however, the ACE inhibitors are associated with adverse effects that result in their being contraindicated in patients with certain disease states (e.g., renal artery stenosis).

Similarly, inotropic agent therapy (i.e., a drug that improves cardiac output by increasing the force of myocardial muscle contraction) may also be indicated if the diuretics do not result in adequate relief. The inotropic agent most commonly used by ambulatory patients is digitalis. However, it is associated with a panoply of adverse reactions, including gastrointestinal problems and central nervous system dysfunction.

Thus, the currently used pharmacological agents have shortcomings, and the availability of new, safe and effective agents would undoubtedly benefit patients who either cannot use the pharmacological modalities presently available, or who do not receive adequate relief from those modalities.

IV. PHARMACEUTICAL COMPOSITIONS AND METHODS OF TREATMENT

A. Compositions

It is envisioned that, for administration to a host, compounds and cells of the present invention will be suspended in a formulation suitable for administration to a host. Aqueous compositions of the present invention comprise an effective amount of a compound and/or cells dispersed in a pharmaceutically acceptable formulation and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutically active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

B. Administration

Compounds and/or cells for administration will generally be formulated for parenteral administration, e.g., formulated for injection via the intravenous, intramuscular, subcutaneous, intralesional, or even intraperitoneal routes. The preparation of an aqueous composition that contains cells as a viable component or ingredient will be known to those of skill in the art in light of the present disclosure. In all cases the form should be sterile and must be fluid to the extent that easy syringability exists and that viability of the cells is maintained. It is generally contemplated that the majority of culture media will be removed from cells prior to administration.

Islet transplantation is particularly contemplated as part of the present invention. Once transplanted, the islets begin to produce insulin, actively regulating the level of glucose in the blood. Islets are usually infused into the patient's liver. If the cells are not from a genetically identical donor, the patient's body will recognize them as foreign and the immune system will begin to attack them as with any transplant rejection. To prevent this, immunosupressant drugs are used. Recent studies have shown that islet transplantation has progressed to the point that 58% of the patients in one study were insulin independent one year after the operation.

The goal of islet transplantation is to infuse enough islets to control the blood glucose level removing the need for insulin injections. For an average-size person (70 kg), a typical transplant requires about one million islets, isolated from two donor pancreases. Because good control of blood glucose can slow or prevent the progression of complications associated with diabetes, such as nerve or eye damage, a successful transplant may reduce the risk of these complications. But a transplant recipient will need to take immunosuppressive drugs that stop the immune system from rejecting the transplanted islets.

Researchers use a mixture of highly purified enzymes called collagenases to isolate islets from the pancreas of a deceased donor. Collagenase solution is injected into the pancreatic duct, which runs through the head, body and tail of the pancreas. Delivered this way, the enzyme solution causes distension of the pancreas, which is subsequently cut into small chunks and transferred into so-called Ricordi's chamber, where digestion takes place until the islets are liberated and removed from the solution. Isolated islets are then separated from the exocrine tissue and debris in a process called purification.

During the transplant, a radiologist uses ultrasound and radiography to guide placement of a catheter through the upper abdomen and into the portal vein of the liver. The islets are then infused through the catheter into the liver. The patient will receive a local anesthetic. If a patient cannot tolerate local anesthesia, the surgeon may use general anesthesia and do the transplant through a small incision. Possible risks of the procedure include bleeding or blood clots.

It takes time for the islets to attach to new blood vessels and begin releasing insulin. The doctor will order many tests to check blood glucose levels after the transplant, and insulin may be needed until control is achieved.

In particular, the Edmonton Protocol or a variation thereof is contemplated. The Edmonton Protocol is a method of implantation of pancreatic islets for the treatment of type 1 diabetes mellitus. The protocol involves isolating islets from a cadaveric donor pancreas using a mixture of enzymes called Liberase® (Roche). Each recipient receives islets from one to as many as three donors. The islets are infused into the patient's portal vein, followed by use of two immunosuppressants, sirolimus and tacrolimus, as well as the monoclonal antibody daclizumab, to prevent attack by the recipient's immune system. Sirolimus and tacrolimus, the two main drugs that keep the immune system from destroying the transplanted islets, must be taken for life.

Two of the most important limitations are the currently inadequate means for preventing islet rejection, and the limited supply of islets for transplantation. Current immunosuppressive regimens are capable of preventing islet failure for months to years, but the agents used in these treatments are expensive and may increase the risk for specific malignancies and opportunistic infections. In addition, and somewhat ironically, the most commonly used agents (like calcineurin inhibitors and rapamycin) are also known to impair normal islet function and/or insulin action. Further, like all medications, the agents have other associated toxicities, with side effects such as oral ulcers, peripheral edema, anemia, weight loss, hypertension, hyperlipidemia, diarrhea and fatigue. Perhaps of greatest concern to the patient and physician is the harmful effect of certain widely employed immunosuppressive agents on renal function. For the patient with diabetes, renal function is a crucial factor in determining long-term outcome, and calcineurin inhibitors (tacrolimus and ciclosporin) are significantly nephrotoxic. Thus, while some patients with a pancreas transplant tolerate the immunosuppressive agents well, and for such patients diabetic nephropathy can gradually improve, in other patients the net effect (decreased risk due to the improved blood glucose control, increased risk from the immunosuppressive agents) may worsen kidney function. Indeed, Ojo et al. have published an analysis indicating that among patients receiving other-than-kidney allografts, 7%-21% end up with renal failure as a result of the transplant and/or subsequent immunosuppression.

Like all transplantation therapies, islet transplantation is also handicapped by the limited donor pool. The numbers are striking; at least 1 million Americans have type 1 diabetes mellitus, and only a few thousand donor pancreata are available each year. To circumvent this organ shortage problem, researchers continue to look for ways to "grow" islets—or at least cells capable of physiologically regulated insulin secretion—in vitro, but currently only islets from cadaveric donors can be used to restore euglycemia. Further exacerbating the problem (and unlike kidney, liver, and heart transplants, where only one donor is needed for each recipient) most islet transplant patients require islets from two or more donors to achieve euglycemia. Lastly, the current methods for islet isolation need improvement, since only about half of attempted isolations produce transplant-ready islets. The present invention therefore provides improved methods for treating and stimulating β-cells, including those that have reduced insulin product or have lost the ability entirely. The compositions of the present invention and increase/reactivate the insulin production in these cells, and may further induce β-cell proliferation. The treatments may occur ex vivo following retrieval from a cadaver or the patient being treated, or following transplant in vivo.

Generally, dispersions are prepared by incorporating the compounds or cells into a sterile vehicle which contains the basic dispersion medium and the required other ingredients for maintaining cell viability as well as potentially additional components to effect proliferation, differentiation or replacement/grafting in vivo. Upon formulation, solutions will be administered in a manner compatible with the dosage formulation or in such amount as is therapeutically effective. Some variation in dosage will necessarily occur depending on the condition of the subject being treated. The person responsible for administration will, in any event, determine the appropriate dose for the individual subject.

C. Adjunct Therapies and Procedures

1. Diabetes

In accordance with the present invention, it may prove advantageous to combine the methods disclosed herein with adjunct therapies or procedures to enhance the overall anti-diabetic effect. Such therapies and procedures are set forth in general, below. A skilled physician will be apprised of the most appropriate fashion in which these therapies and procedures may be employed.

The present invention, though designed to eliminate the need for other therapies, is contemplated to provide advantageous use with traditional insulin supplementation, but at lower levels, such as below 90%, below 80%, below 70%, below 60%, below 50%, below 40%, below 30%, below 20%, below 15%, 10-15%, below 10%, 5-10%, below 5%, 4%, 3%, 2% or 1% of the normal daily dosage of insulin. Normal daily dosage for TD1 is 30-60 units per day. Such therapies should be tailored specifically for the individual patient given their current clinical situation, and it is contemplated that a subject could be "weaned" down or off insulin therapy after commencing isoxazole provision. The following are general guidelines for typical a "monotherapy" using insulin supplementation by injection, and can be applied here, albeit in the context of the aforementioned reductions in total daily dosage.

Insulin can be injected in the thighs, abdomen, upper arms or gluteal region. In children, the thighs or the abdomen are preferred. These offer a large area for frequent site rotation and are easily accessible for self-injection. Insulin injected in the abdomen is absorbed rapidly while from the thigh it is absorbed more slowly. Hence, patients should not switch from one area to the other at random. The abdomen should be used for the time of the day when a short interval between injection and meal is desired (usually pre-breakfast when the child may be in a hurry to go to school) and the thigh when the patient can wait 30 minutes after injection for his meal (usually pre-dinner). Within the selected area systematic site rotation must be practiced so that not more than one or two injections a month are given at any single spot. If site rotation is not practiced, fatty lumps known as lipohypertrophy may develop at frequently injected sites. These lumps are cosmetically unacceptable and, what is more important, insulin absorption from these regions is highly erratic.

Before injecting insulin, the selected site should be cleaned with alcohol. Injecting before the spirit evaporates can prove to be quite painful. The syringe is held like a pen in one hand, pinching up the skin between the thumb and index finger of the other hand, and inserting the needle through the skin at an angle of 45-90° to the surface. The piston is pushed down to inject insulin into the subcutaneous space (the space between the skin and muscle), then one waits for a few seconds after which release the pinched up skin before withdrawing the needle. The injection site should not be massaged.

For day-to-day management of diabetes, a combination of short acting and intermediate acting insulin is used. Some children in the first year after onset of diabetes may remain well controlled on a single injection of insulin each day. However, most diabetic children will require 2, 3 or even 4 shots of insulin a day for good control. A doctor should decide which regimen is best suited.

One Injection Regimen:

A single injection comprising a mix of short acting and intermediate acting insulin (mixed in the same syringe) in 1:3 or 1:4 proportion is taken 20 to 30 minutes before breakfast. The usual total starting dose is 0.5 to 1.0 units/kg body weight per day. This regimen has three disadvantages: (1) all meals must be consumed at fixed times; (2) since the entire quantity of insulin is given at one time, a single large peak of insulin action is seen during the late and early evening hours making one prone to hypoglycemia at this time; (3) as the action of intermediate acting insulin rarely lasts beyond 16-18 hours, the patient's body remains under-insulinized during the early morning hours, the period during which insulin requirement in the body is actually the highest.

Two-Injection Regimen:

This regimen is fairly popular. Two shots of insulin are taken—one before breakfast (⅔ of the total dose) and the other before dinner (⅓ of the total dose). Each is a combination of short acting and intermediate acting insulin in the ratio of 1:2 or 1:3 for the morning dose, and 1:2 or 1:1 for the evening dose. With this regimen the disadvantages of the single injection regimen are partly rectified. Some flexibility is possible for the evening meal. Further, as the total days' insulin is split, single large peaks of insulin action do not occur hence risk of hypoglycemia is reduced and one remains more or less evenly insulinized throughout the day. On this regimen, if the pre-breakfast blood glucose is high, while the 3 a.m. level is low, then the evening dose may need to be split so as to provide short acting insulin before dinner and intermediate acting insulin at bedtime.

Multi-Dose Insulin Regimens:

The body normally produces insulin in a basal-bolus manner, i.e., there is a constant basal secretion unrelated to meal intake and superimposed on this there is bolus insulin release in response to each meal. Multi-dose insulin regimens were devised to mimic this physiological pattern of insulin production. Short acting insulin is taken before each major meal (breakfast, lunch and dinner) to provide "bolus insulin" and intermediate acting insulin is administered once or twice a day for "basal insulin." Usually bolus insulin comprises 60% of the total dose and basal insulin makes up the remaining 40%. With this regimen you have a lot of flexibility. Both the timing as well as the quantity of each meal can be altered as desired by making appropriate alterations in the bolus insulin doses. To take maximum advantage of this regimen, one should learn "carbohydrate counting" and work out carbohydrate:insulin ratio—the number of grams of carbohydrate for which the body needs 1 unit of insulin.

Any person suffering from diabetes will be very familiar with the need to regularly measure blood glucose levels. Blood glucose level is the amount of glucose, or sugar, in the blood. It is also is referred to as "serum glucose level." Normally, blood glucose levels stay within fairly narrow limits throughout the day (4 to 8 mmol/l), but are often higher after meals and usually lowest in the morning. Unfortunately, when a person has diabetes, their blood glucose level sometimes moves outside these limits. Thus, much of a diabetic's challenge is to When one suffers from diabetes, it is important that glucose level be as near normal as possible. Stable blood glucose significantly reduces the risk of developing late-stage diabetic complications, which start to appear 10 to 15 years after diagnosis with type 1 diabetes, and often less than 10 years after diagnosis with type 2 diabetes.

Blood glucose levels can be measured very simply and quickly with a home blood glucose level testing kit, consisting of a measuring device itself and a test strip. To check blood glucose level, a small amount of blood is placed on the test strip, which is then placed into the device. After about 30 seconds, the device displays the blood glucose level. The best way to take a blood sample is by pricking the finger with a lancet. Ideal values are (a) 4 to 7 mmol/l before meals, (b) less than 10 mmol/l one-and-a-half hours after meals; and (c) around 8 mmol/l at bedtime.

People who have type 1 diabetes should measure their blood glucose level once a day, either in the morning before breakfast or at bedtime. In addition, a 24-hour profile should be performed a couple of times a week (measuring blood glucose levels before each meal and before bed). People who have type 2 diabetes and are being treated with insulin should also follow the schedule above. People who have type 2 diabetes and who are being treated with tablets or a special diet should measure their blood glucose levels once or twice a week, either before meals or one-and-a-half hours after a meal. They should also perform a 24-hour profile once or twice a month.

The main advantage for measuring blood glucose levels of insulin-treated diabetics in the morning is that adjusted amounts of insulin can be taken if the blood glucose level is high or low, thereby reducing the risk of developing late-stage diabetic complications. Similarly, the blood glucose level at bedtime should be between 7 and 10 mmol/l. If blood glucose is very low or very high at bedtime, there may be a need to adjust food intake or insulin dose. Blood glucose should also be measured any time the patient does not feel well, or think blood glucose is either too high or too low. People who have type 1 diabetes with a high level of glucose in their blood (more than 20 mmol/l), in addition to sugar traces in the urine, should check for ketone bodies in their urine, using a urine strip. If ketone bodies are present, it is a warning signal that they either have, or may develop, diabetic acidosis.

2. Cancer

It is very common in the field of cancer therapy to combine therapeutic modalities. The following is a general discussion of therapies that may be used in conjunction with the therapies of the present disclosure.

i. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein transferase inhibitors, transplatinum, 5-fluorouracil, vincristin, vinblastin and methotrexate and pharmaceutically acceptable salts, acids or derivatives of any of the above.

ii. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets, which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

iii. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance antitumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

iv. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used with the present invention. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

3. Heart Disease

Non-limiting examples of a pharmacological therapeutic agents that may be used in combination with the agents of the present disclosure include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof. The following provides a more specific listing of certain types of agents.

i. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol) or simvastatin (zocor).

d. Nicotinic Acid Derivatives

Non-limiting examples of nicotinic acid derivatives include nicotinate, acepimox, niceritrol, nicoclonate, nicomol and oxiniacic acid.

e. Thyroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, b-benzalbutyramide, camitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, g-oryzanol, pantethine, pentaerythritol tetraacetate, a-phenylbutyramide, pirozadil, probucol (lorelco), b-sitosterol, sultosilic acid-piperazine salt, tiadenol, triparanol and xenbucin.

ii. Antiarteriosclerotics

Non-limiting examples of an antiarteriosclerotic include pyridinol carbamate.

iii. Antithrombotic/Fibrinolytic Agents

In certain embodiments, administration of an agent that aids in the removal or prevention of blood clots may be combined with administration of a modulator, particularly in treatment of atherscelosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and warfarin (coumadin), are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantin), heparin, sulfinpyranone (anturane) and ticlopidine (ticlid).

c. Thrombolytic Agents

Non-limiting examples of thrombolytic agents include tissue plasminogen activator (activase), plasmin, pro-urokinase, urokinase (abbokinase) streptokinase (streptase), anistreplase/APSAC (eminase).

iv. Blood Coagulants

In certain embodiments wherein a patient is suffering from a hemorrhage or an increased likelihood of hemorrhaging, an agent that may enhance blood coagulation may be used. Non-limiting examples of a blood coagulation promoting agent include thrombolytic agent antagonists and anticoagulant antagonists.

a. Anticoagulant Antagonists

Non-limiting examples of anticoagulant antagonists include protamine and vitamine K1.

b. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

v. Antiarrhythmic Agents

Non-limiting examples of antiarrhythmic agents include Class I antiarrhythmic agents (sodium channel blockers), Class II antiarrhythmic agents (beta-adrenergic blockers), Class II antiarrhythmic agents (repolarization prolonging drugs), Class IV antiarrhythmic agents (calcium channel blockers) and miscellaneous antiarrhythmic agents.

a. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocainide (tonocard) and mexiletine (mexitil). Non-limiting examples of Class IC antiarrhythmic agents include encainide (enkaid) and flecainide (tambocor).

b. Beta Blockers

Non-limiting examples of a beta blocker, otherwise known as a b-adrenergic blocker, a b-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

c. Repolarization Prolonging Agents

Non-limiting examples of an agent that prolong repolarization, also known as a Class III antiarrhythmic agent, include amiodarone (cordarone) and sotalol (betapace).

d. Calcium Channel Blockers/Antagonist

Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexiline. In certain embodiments a calcium channel blocker comprises a long-acting dihydropyridine (amlodipine) calcium antagonist.

e. Miscellaneous Antiarrhythmic Agents

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

vi. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an a-adrenergic blocker or an a-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a .beta.-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a beta-adrenergic blocker include acenitolol (sectral), atenolol (tenormin), betaxolol (kerlone), carteolol (cartrol), labetalol (nornodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

e. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, dropreniIamine, efloxate, erythrityl tetranitrane, etafenone, fendiline, floredil, ganglefene, herestrol bis(b-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimethylline, trapidil, tricromyl, trimetazidine, troInitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, g aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quantemary ammonium compound, a reserpine derivative or a suflonamide derivative.

Arylethanolamine Derivatives. Non-limiting examples of arylethanolamine derivatives include amosulalol, bufuralol, dilevalol, labetalol, pronethalol, sotalol and sulfinalol.

Benzothiadiazine Derivatives. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothiazide, hydroflumethiazide, methyclothiazide, meticrane, metolazone, paraflutizide, polythizide, tetrachlormethiazide and trichlormethiazide.

N-carboxyalkyl(peptide/lactam) Derivatives. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives. Non-limiting examples of dihydropyridine derivatives include amlodipine, felodipine, isradipine, nicardipine, nifedipine, nilvadipine, nisoldipine and nitrendipine.

Guanidine Derivatives. Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines. Non-limiting examples of hydrazines/phthalazines include budralazine, cadralazine, dihydralazine, endralazine, hydracarbazine, hydralazine, pheniprazine, pildralazine and todralazine.

Imidazole Derivatives. Non-limiting examples of imidazole derivatives include clonidine, lofexidine, phentolamine, tiamenidine and tolonidine.

Quanternary Ammonium Compounds. Non-limiting examples of quantemary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives. Non-limiting examples of reserpine derivatives include bietaserpine, deserpidine, rescinnamine, reserpine and syrosingopine.

Suflonamide Derivatives. Non-limiting examples of sulfonamide derivatives include ambuside, clopamide, furosemide, indapamide, quinethazone, tripamide and xipamide.

vii. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

viii. Treatment Agents for Congestive Heart Failure

Non-limiting examples of agents for the treatment of congestive heart failure include anti-angiotension II agents, afterload-preload reduction treatment, diuretics and inotropic agents.

a. Afterload-Preload Reduction

In certain embodiments, an animal patient that cannot tolerate an angiotension antagonist may be treated with a combination therapy. Such therapy may combine administration of hydralazine (apresoline) and isosorbide dinitrate (isordil, sorbitrate).

b. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticrnafen and urea.

c. Inotropic Agents

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a .beta.-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include anrinone (inocor).

d. Antianginal Agents

Antianginal agents may comprise organonitrates, calcium channel blockers, beta-blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

viii. Surgical Therapies and Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

V. EXAMPLES

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Chemicals.

All reagents and chemicals were obtained from Sigma-Aldrich unless otherwise indicated.

Synthesis of PDK Inhibitors.

All reactions were carried out under an atmosphere of argon in flame-dried glassware with magnetic stirring unless otherwise indicated. Commercially obtained reagents were used as received. Solvents were dried by passage through an activated alumina column under argon. Liquids and solutions were transferred via syringe. All reactions were monitored by thin-layer chromatography with E. Merck silica gel 60 F254 pre-coated plates (0.25 mm). Silica gel particle size 0.032-0.063 mm) purchased from SiliCycle was used for flash chromatography. $^1$H and $^{13}$C NMR spectra were recorded on Varian Inova-400 or 500 spectrometers. Data for $^1$H NMR spectra are reported relative to CDCl$_3$ (7.26 ppm), CD$_3$OD (3.31 ppm), or DMSO-d6 (2.50 ppm) as an internal standard and are reported as follows: chemical shift ($\delta$ ppm), multiplicity, coupling constant (Hz), and integration. Data for $^{13}$C NMR spectra are reported relative to CDCl$_3$ (77.23 ppm), CD$_3$OD (49.00 ppm) or DMSO-d6 (39.52 ppm) as an internal standard and are reported in terms of chemical shift ($\delta$ ppm). LRMS data were obtained on an Agilent 1200 Series LCMS System.

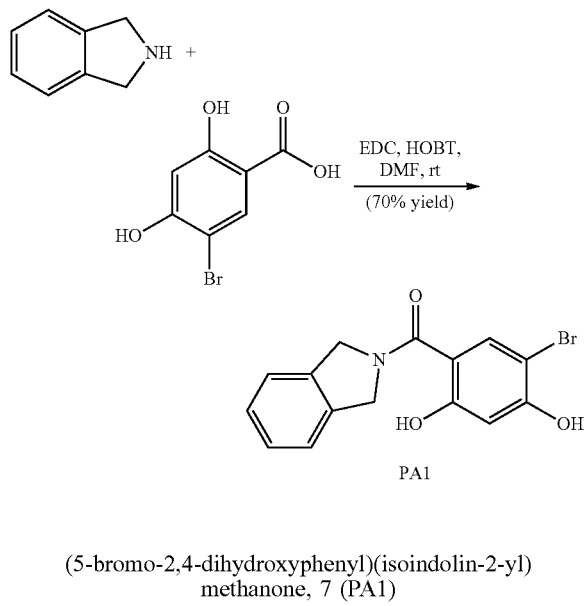

(5-bromo-2,4-dihydroxyphenyl)(isoindolin-2-yl)
methanone, 7 (PA1)

In a 50 mL, three-necked, round-bottomed flask, 5-bromo-2,4-dihydroxybenzoic acid (1.42 g, 5.65 mmol, 1.13 equivalent), 1-ethyl-3-(3-dimethylaminopropyl)carbodiimide (EDC, 1.02 g, 5.25 mmol, 1.05 equivalent) and 1-Hydroxybenzotriazole (HOBT, 776 mg, 5.75 mmol, 1.15 equivalent) were dissolved in dimethylformamide (10 mL) at room temperature. The mixture was stirred at the same temperature for 30 min before isoindoline (596 mg, 5 mmol, 1 equivalent) was added. After 18 h, the reaction mixture was diluted with ethyl acetate (50 mL) and washed sequentially with 1N HCl aqueous solution, saturated aqueous NaHCO$_3$, and brine. The organic layer was dried over sodium sulfate and concentrated under reduced pressure. The residue was purified by flash chromatography (silica gel; ethyl acetate: hexanes 1:20 to 1:1) to yield PA1 (1.17 g, 70% yield). $^1$H NMR (500 MHz, DMSO-d6) δ 10.50 (s, 1H), 10.34 (s, 1H), 7.38-7.36 (m, 2H), 7.34 (s, 1H), 7.29-7.27 (m, 2H), 6.59 (s, 1H), 4.77 (s, 2H), 4.70 (s, 2H); $^{13}$C NMR (125 MHz, DMSO-d6) δ 166.6, 155.8, 154.7, 136.9, 131.7, 127.4, 122.9, 117.2, 103.7, 98.6, 52.7 (Rotamers were observed). LRMS (ESI) calculated for [M+H]$^+$ 334.0. found 333.9.

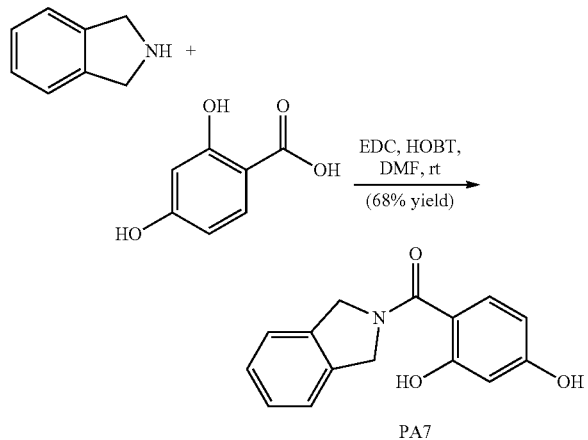

(2,4-dihydroxyphenyl)(isoindolin-2-yl)methanone, 8
(PA7)

Following the general procedure for the synthesis PA1, 2,4-dihydroxybenzoic acid (386.5 mg, 2.3 mmol, 1.13 equivalent) and isoindoline (238.3 mg, 2 mmol, 1 equivalent) were converted to PA7 (350 mg, 68% yield). $^1$H NMR (500 MHz, DMSO-d6) δ 10.49 (s, 1H), 9.74 (s, 1H), 7.38-7.28 (m, 4H), 7.22 (d, J=8.4 Hz, 1H), 6.36 (d, J=2.3 Hz, 1H), 6.31 (dd, J=8.4, 2.3 Hz, 1H), 4.80-4.79 (m, 4H); $^{13}$C NMR (125 MHz, DMSO-d6) δ 169.0, 160.4, 157.3, 129.9, 127.8, 123.3, 114.4, 107.1, 103.1, 53.6. LRMS (ESI) calculated for [M+H]$^+$ 256.3. found 256.0.

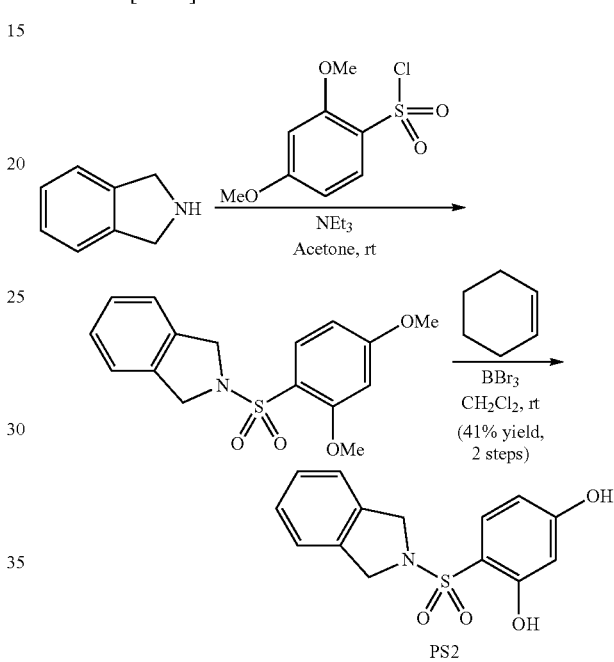

4-(isoindolin-2-ylsulfonyl)benzene-1,3-diol, 9 (PS2)

In a 10 mL, three-necked, round-bottomed flask, 2,4-dimethoxybenzene-1-sulfonyl chloride (237 mg, 1 mmol, 1 equivalent) was dissolved in acetonitrile (3 mL) at room temperature. Triethylamine (0.3 mL) was added before isoindoline (238 mg, 2 mmol, 2 equivalent) was added. The mixture was stirred at the same temperature for 18 h and then diluted with ethyl acetate (50 mL). The mixture was washed sequentially with 1N HCl aqueous solution, saturated aqueous NaHCO$_3$, and brine. The organic layer was dried over sodium sulfate and concentrated under reduced pressure to yield a solid, which was confirmed by NMR. $^1$H NMR (500 MHz, CDCl$_3$) δ 7.95 (d, J=8.2 Hz, 2H), 7.29-7.25 (m, 2H), 7.22-7.20 (m, 2H), 6.55 (dd, J=8.2, 2.3 Hz, 1H), 6.44 (d, J=2.3 Hz, 1H), 4.76 (s, 4H), 3.86 (s, 3H), 3.76 (s, 3H); $^{13}$C NMR (125 MHz, CDCl$_3$) δ 164.9, 158.4, 136.9, 134.0, 127.6, 122.7, 118.8, 104.3, 99.5, 56.1, 55.9, 53.9. LRMS (ESI) calculated for [M+H]$^+$ 320.1. found 320.0.

The crude product was dissolved in methylene chloride (10 mL) and cyclohexene (1 mL) and cooled to 0° C. BBr$_3$ (10 equivalent) was added at the same temperature. The mixture was stirred at 0° C. for 2 h before warming to room temperature. After 2 h, the reaction mixture was quenched very carefully by the dropwise addition of methanol (~3 mL) at 0° C. The reaction solution was concentrated under reduced pressure, dissolved in ethyl acetate, and washed with saturated aqueous NaHCO₃ and brine. The organic layer was dried over sodium sulfate and concentrated under reduced pressure. The residue obtained was purified by flash chromatography (silica gel; ethyl acetate:hexanes 1:20 to 1:1) to yield PS2 (120 mg, 41% yield over two steps). $^1$H NMR (500 MHz, CD₃OD) δ 7.61 (d, J=8.8 Hz, 1H), 7.24-7.20 (m, 4H), 6.40 (dd, J=8.8, 2.3 Hz, 1H), 6.32 (d, J=2.3 Hz, 1H), 4.67 (s, 4H); $^{13}$C NMR (125 MHz, CD₃OD) δ 167.4, 161.4, 140.3, 136.2, 131.2, 126.1, 117.2, 110.9, 106.8, 57.2. LRMS (ESI) calculated for [M+H]⁺ 292.1. found 291.9.

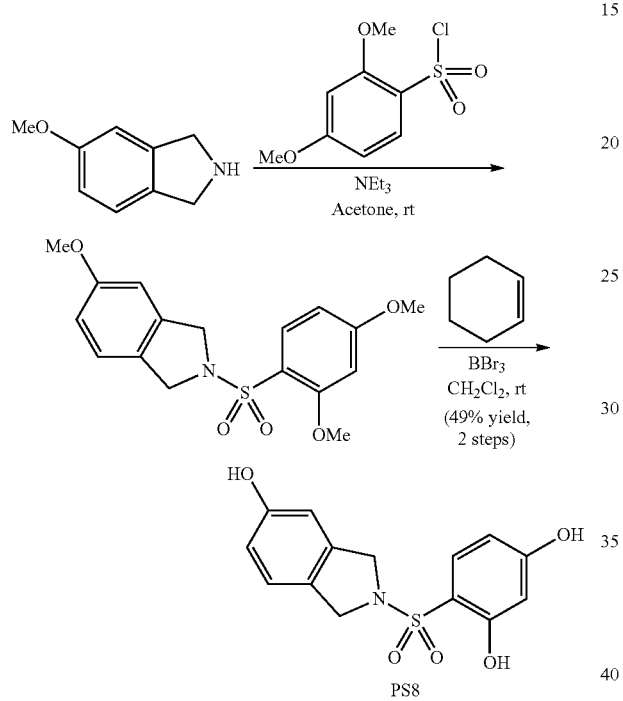

4-((5-hydroxyisoindolin-2-yl)sulfonyl)benzene-1,3-diol, 10 (PS8)

Following the general procedure for the synthesis PS2, 5-methoxyisoindoline was converted to PS8 (49% yield over two steps). $^1$H NMR (500 MHz, CD₃OD) δ 7.59 (d, J=8.8 Hz, 1H), 7.01 (d, J=8.3 Hz, 1H), 6.66 (dd, J=8.3, 2.4 Hz, 1H), 6.62 (d, J=2.4 Hz, 1H), 6.38 (dd, J=8.8, 2.4 Hz, 1H), 6.33 (d, J=2.4 Hz, 1H), 4.60 (s, 2H), 4.53 (s, 2H); $^{13}$C NMR (125 MHz, CD₃OD) δ 163.4, 157.4, 157.0, 137.7, 132.1, 126.8, 122.9, 114.6, 113.2, 108.6, 106.9, 102.9, 53.4, 52.7. LRMS (ESI) calculated for [M+H]⁺ 308.0. found 307.9.

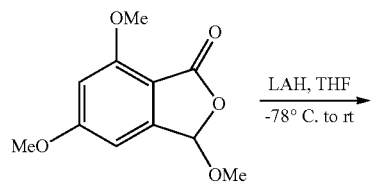

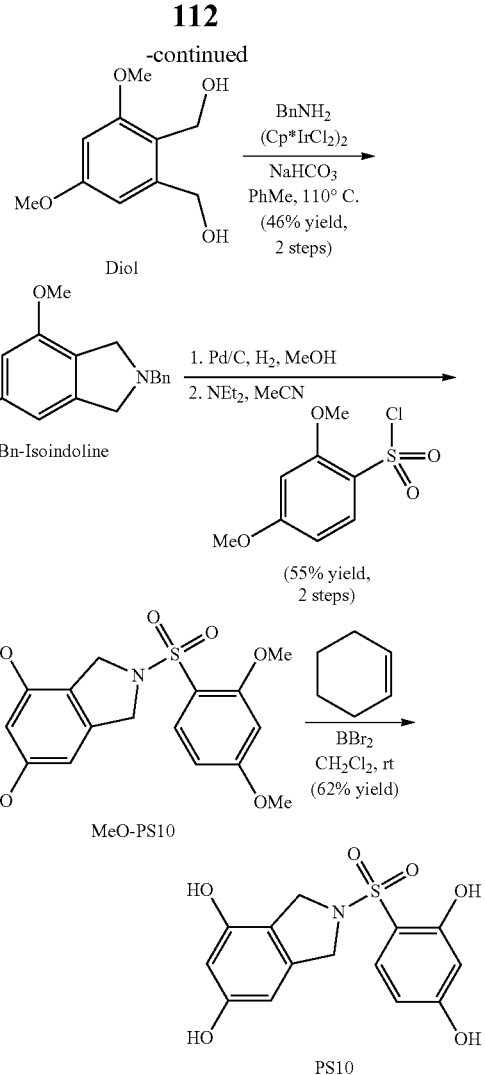

Diol:

In a 250 mL, three-necked, round-bottomed flask, 3,5,7-trimethoxyisobenzofuran-1(3H)-one (4.6 g, 20 mmol, 1 equivalent) was dissolved in tetrahydrofuran (100 mL) at room temperature. The reaction flask was cooled to 78° C. before the lithium aluminum hydride solution (1.0 M in THF, 40 mL, 2 equivalent) was added very slowly. After the addition was complete, the mixture was stirred at the same temperature for 1 h before it was warmed to room temperature slowly (~2 h). After the starting material was consumed by TLC, the reaction mixture was quenched slowly by the addition of solid NaSO₄-10.H₂O until no bubbles were generated. The mixture was then filtered through a short celite plug, and washed with ethyl acetate (50 mL). The filtrate was concentrated under reduced pressure to yield the Diol as a solid (4.2 g), which was confirmed by NMR. $^1$H NMR (500 MHz, CDCl₃) δ 6.52 (d, J=2.0 Hz, 1H), 6.44 (d, J=2.0, Hz 1H), 4.75 (s, 2H), 4.67 (s, 2H), 3.82 (s, 3H), 3.81 (s, 3H); $^{13}$C NMR (125 MHz, CDCl₃) δ 160.6, 159.2, 142.4, 120.2, 105.9, 98.4, 64.7, 64.5, 56.1. LRMS (ESI) calculated for [M+Na]⁺221.0. found 221.0.

Bn-isoindoline:

A sealed tube was charged with the crude Diol (1 mmol, 1 equivalent), pentamethylcyclopentadienyl iridium catalyst [Cp*IrCl₂]₂ (0.01 mmol, 1 mol %), NaHCO₃ (0.01 mmol, 1 mol %), benzylamine (2 mmol, 2 equivalent), and toluene (0.5 mL). The reaction flask was sealed and the mixture was stirred at 110° C. for 30 h. After the solvent was removed under reduced pressure, the residue was purified by flash chromatography (silica gel; ethyl acetate:hexanes 1:20 to 1:1) to yield Bn-isoindoline (2.75 g, 46% yield over two steps). $^1$H NMR (500 MHz, CDCl$_3$) δ 7.45 (d, J=7.2 Hz, 2H), 7.38 (t, J=7.2 Hz, 2H), 7.30 (t, J=7.2 Hz, 1H), 6.39 (s, 1H), 6.34 (s, 1H), 3.95 (s, 2H), 3.93 (s, 2H), 3.91 (s, 2H), 3.80 (s, 3H), 3.79 (s, 3H).

MeO-PS10:

In a 250 mL, round-bottomed flask, the Bn-isoindoline (2.75 g, 10 mmol) was dissolved in methanol (100 mL), and the resulting solution was sparged with argon for 5 min before Pd/C (300 mg, 10% dry powder) was added carefully. After the addition of the catalyst, the flask was sparged with a balloon of H$_2$ gas (1 atm) for 10 min and then stirred under an atmosphere of H$_2$ (1 atm) for 40 h. After the starting material was consumed by TLC, the reaction mixture was filtered through a plug of celite and concentrated under reduced pressure.

The crude mixture was dissolved in acetonitrile (50 mL) at room temperature. Triethylamine (5 mL) and 2,4-dimethoxybenzene-1-sulfonyl chloride (2.24 g, 9.5 mmol, 1 equivalent) were sequentially added. The mixture was stirred at the same temperature for 18 h and diluted with ethyl acetate (100 mL). The mixture was washed sequentially with 1N HCl aqueous solution, saturated aqueous NaHCO$_3$, and brine. The organic layer was dried over sodium sulfate, concentrated under reduced pressure, and purified by flash chromatography (silica gel; ethyl acetate: hexanes 1:20 to 1:1) to yield MeO-PS10 as a white solid (2.09 g, 55% yield over two steps). $^1$H NMR (500 MHz, CDCl$_3$) δ 7.90 (d, J=8.8 Hz, 1H), 6.51 (dd, J=8.8, 2.3 Hz, 1H), 6.41 (d, J=2.3 Hz, 1H), 6.30-6.29 (m, 2H), 4.71 (s, 2H), 4.56 (s, 2H), 3.83 (s, 3H), 3.77 (s, 3H), 3.76 (s, 3H), 3.75 (s, 3H); $^{13}$C NMR (125 MHz, CDCl$_3$) δ 164.8, 161.5, 158.4, 155.5, 139.0, 134.0, 119.0, 117.4, 104.2, 99.6, 98.3, 97.5, 56.1, 55.9, 55.8, 55.5, 54.6, 51.6. LRMS (ESI) calculated for [M+H]$^+$ 380.1. found 379.9.

2-((2,4-dihydroxyphenyl)sulfonyl)isoindoline-4,6-diol, 11 (PS10)

A solution of MeO-PS10 in methylene chloride (100 mL) and cyclohexene (20 mL) was cooled to 0° C. BBr$_3$ (15 equivalents) was added at the same temperature. The mixture was stirred at 0° C. for 2 h and warmed to room temperature. After 2 h, the reaction mixture was quenched very carefully by the dropwise addition of methanol (~10 mL) at 0° C. The reaction solution was concentrated under reduced pressure, dissolved in ethyl acetate, and washed with saturated aqueous NaHCO$_3$ and brine. The organic layer was dried over sodium sulfate and concentrated under reduced pressure. The residue obtained was purified by flash chromatography (silica gel; ethyl acetate:hexanes 1:20 to 1:1) to yield PS10 as a white solid (1.1 g, 62% yield). $^1$H NMR (500 MHz, CD$_3$OD) δ 7.56 (d, J=8.8 Hz, 1H), 6.35 (dd, J=8.8, 2.3 Hz, 1H), 6.32 (d, J=2.3 Hz, 1H), 6.11 (brs, 2H), 4.52 (s, 2H), 4.44 (s, 2H); $^{13}$C NMR (125 MHz, CD$_3$OD) δ 164.7, 159.8, 158.8, 154.1, 140.0, 133.4, 115.0, 114.5, 108.4, 104.3, 102.3, 101.4, 55.1, 52.22. LRMS (ESI) calculated for [M+H]$^+$ 324.0. found 323.9.

Proteins.

Recombinant human PDK2 was expressed and purified as a N terminal His6-tagged SUMO fusion protein with a tobacco-etch-virus protease (TEV) cleavage site in front of the N-terminal PDK2 sequence (26), and was used directly for the activity assay and binding affinity analyses. For crystallization, the protein was subjected to a TEV-protease digestion, and the untagged PDK2 protein was purified on a Superdex 200 column in 20 mM Tris-HCl (pH 8.0), 150 mM NaCl and 5 mM DTT. The purified protein was concentrated to 35-40 mg/ml and stored at −80° C. in small aliquots. Recombinant human PDK1, PDK3 and PDK4 were expressed and purified as described previously (26).

To express the N-terminal domain (residue 1-236) of human Hsp90, the first strand cDNA was synthesized with the human total RNA as template using the Omniscript Reverse Transcriptase from Qiagen (Gaithersburg, Md.). The sequence encoding the N-terminal domain was amplified and cloned into the pSUMO expression vector (Lifesensors, Malvern, Pa.). The fusion protein of His6-tagged SUMO-Hsp90 N-terminal domain was expressed in *E. coli* BL21 cells and purified with Ni-NTA resin (Qiagen) and on Superdex-200 column in 20 mM Tris.HCl, pH 7.5 and 500 mM NaCl.

Assay for Inhibition of PDK Activity.

To determine the IC$_{50}$ for PDK inhibitors, a mixture containing 0.05-0.2 μM PDK, 6 μM E1, with or without 0.5 μM of the PDC core E2/E3BP, and various amounts of inhibitor was incubated at 25° C. for 10 min in a buffer of 20 mM Tris-Cl (pH 7.5), 10 mM KCl, 5 mM MgCl$_2$, 2 mM DTT, 0.02% (v/v) Tween-20, and 0.1 mg/ml bovine serum albumin before the addition of 50 μM ATP to initiate the reaction. All inhibition titrations were performed at 10 dose-points ranging from 31.6 nM to 1 mM in a 3.162-fold dilution series, with each inhibitor concentration tested in duplicate. The remaining steps were described previously (26). IC$_{50}$ values were obtained by the curve fitting of inhibition isotherms using Prism 6 (GraphPad software, Inc.).

The kinase-profiling of PS8 on 21 human protein kinases were performed at Reaction Biology Corp. (Malvern, Pa.). IC$_{50}$ values were determined by 10-dose titration of PS8 from 15 nM to 300 μM in presence of 10 μM ATP. Each protein kinase was also tested against its known inhibitor as a positive control.

Isothermal Titration Calorimetry (ITC).

The PDK2 or Hsp90 N-terminal domain protein was dialyzed against one liter of the dialysis buffer containing 50 mM Tris-Cl, pH 7.5, 50 mM KCl, 1 mM MgCl$_2$, and 0.5 mM β-mercaptoethanol. Known or novel PDK inhibitor solutions (150-1500 μM) were placed in the titration syringe and injected in 8-μl increments into the reaction cell containing 1.4 ml of 18-70 μM PDK2 or Hsp90 N-terminal domain at 15° C. in a VP-ITC microcalorimeter (GE Healthcare, Piscataway, N.J.). All of the ITC data were initially analyzed by the NITPIC program (32) to construct the baseline, followed by curve-fitting in Origin 7 to obtain binding parameters. The concentrations of PDK2 and Hsp90 N-terminal domain proteins were determined by measuring A280 and using calculated molar extinction coefficients (M−1·cm−1) of 49,530 and 18,910, respectively.

Crystallization of PDK2 and PDK2-Inhibitor Complexes.

Crystals of human PDK2 were obtained by the hanging-drop vapor-diffusion method. Two μl of protein solution was mixed with 2 μl of the well solution (0.9 M ammonium tartrate, 0.1M sodium acetate pH 4.6) and kept in a 20° C. incubator. Crystals were developed in one week and reached the size of 500 μm in two weeks. Mature crystals were transferred to a fresh soaking solution (0.75 M ammonium tartrate, 0.1M sodium acetate pH 4.6 and 5% glycerol with various indicated inhibitors). After overnight incubation, crystals were serially transferred to a cryo-solution containing 20% glycerol and snap frozen in liquid nitrogen.

Structure Determination and Refinements.

All X-ray diffraction data for PDK2 and PDK2-inhibitor complexes were collected at beamline 19-ID at the Advanced Photon Source, Argonne National Laboratories. Diffraction data for each PDK2-inhibitor complex were collected from a single crystal. All crystals share the same space group of I4122, and the highest resolution of diffraction ranged from 1.70 Å to 1.95 Å. The molecular replacement, structure modeling and refinement were performed as described previously (33). The crystal structure of inhibitor-free human PDK (PDB code 2BTZ) was used as the search model.

Pharmacokinetic Studies.

Twenty-one male C57BL/6J mice were dosed IP with 70 mg/kg PS-10, 0.2 ml/mouse formulated as 10% DMSO/20% water/70% of 25% (2-hydroxypropyl)-β-cyclodextrin for determination of PS-10 PK. Twenty-one female CD-1 mice were dosed IP with 20 mg/kg PS-8, 0.2 ml/mouse formulated as 5% ethanol and 95% of 0.1 M sodium bicarbonate pH 9.0 for determination of PS-8 PK. Animal (n=3) were sacrificed and whole blood was harvested for each time point. Plasma was processed from whole blood by centrifugation of the ACD treated blood for 10' at 10,000 rpm in a standard centrifuge. The analytical processing of blood samples and pharmacokinetics studies using LC/MS/MS were as described previously with LC/MS/MS methods optimized for detection of PS-10 and PS-8 (33).

Treatments of Mice with PDK Inhibitors.

Six- to eight-week old C57BL/6J male mice were obtained from the local campus breeding colony at UT Southwestern Medical Center (Dallas, Tex.) and randomized into two groups: vehicle- and PS10-treated. Prior to the treatment, mice were fed with a 60% high-fat diet, which contained 32% saturated and 68% unsaturated fat (catalog number: D12492, Research Diet Inc. New Brunswick, N.J.), for eight to ten weeks to produce DIO animals. PS-10 was dissolved in 100% DMSO and then diluted to make a 10% DMSO aqueous solution containing 17.5% (w/v) (2-hydroxypropyl)-β-cyclodextrin for delivery. Animals were dosed at mid-day by intraperitoneal (IP) injections at 70 mg/kg using 1-ml syringe and 30-gauge needle. The length of the treatment is indicted in each experiment. At 10 h after the last injection, animals were euthanized using carbon dioxide asphyxiation followed by cervical dislocation and dissection. Blood was harvested by cardiac puncture and stored on ice. Acidified citrate dextrose (ACD) was used as an anticoagulant. Immediately after blood collection, heart, liver, kidneys and both hind-leg quadriceps muscles were removed and snap frozen in liquid nitrogen. Average ischemia time before organ harvest was about 2 to 3 min. Blood was centrifuged in an Eppendorf 5415R refrigerated microcentrifuge at 9,300×g for 5 min to isolate plasma, which was subsequently stored at −80° C.

Assay for PDC Activity in Mouse Tissues.

Liquid nitrogen-stored tissue samples were removed and thawed on ice. Individual kidneys (200-250 mg), hearts (200-300 mg), muscle (200-300 mg) and liver (250-400 mg) tissues samples were manually homogenized in an ice-chilled glass homogenizer containing 1 ml of the homogenization buffer. The homogenization buffer contained 30 mM KPi, pH 7.5, 3 mM EDTA, 5 mM DTT, 1 mM benzamidine, 3% fetal bovine serum, 5% Triton X-100 and 1 mM leupeptin. Samples were transferred to ice-cold 10 ml polycarbonate tubes and spun in an ultracentrifuge at 25,000×g for 10 min to pellet cell and tissue debris. Supernatants were removed and stored on ice until diluted (1:3 for muscle, 1:5 for liver and 1:20 for kidneys and heart tissues) with a dilution buffer containing 50 mM HEPES, pH 7.5, 1.0 mM DTT, 0.1% Triton X-100, 5 mM DCA, 50 mM NaF, 3% fetal bovine serum and 1 mM leupeptin. The diluted samples (50 µl) were placed in each well of a 24-well plate containing 310 µl of the reaction mixture. A micro-bridge (Hampton Research) was pre-set into each well holding one piece of filter wick pre-soaked with 2 M NaOH. The reaction mixture contained 30 mM KPi, pH 7.5, 0.4 mM CoA, 3 mM NAD+, 5% fetal bovine serum, 2 mM thiamine diphosphate, 2 mM $MgCl_2$ and 65 µg of recombinant human E3. [1-$^{14}$C] pyruvate (PerkinElmer, Boston, Mass.) was added to each well to initiate the reaction, with the wells sealed with a clear mylar adhesive film. The assay plates were incubated at 37° C. for 10 min. Fifty µl of a 20% TCA solution was added to each well to stop the reaction. Assay plates were incubated further at 37° C. for 45 min. $^{14}CO_2$-trapped on 2 M NaOH soaked filter wicks were counted in a liquid scintillation counter. Total protein concentrations in the samples were determined by using BCA protein assay kit (Thermo fisher Scientific, Rockford, Ill.).

Western Blotting.

SDS-PAGE gels were run using 15-20 µg of protein lysate per lane. Western blots were transferred to PVDF membranes for 2 hrs at 200 mV. PVDF membranes were blocked with 5% non-fat dried milk and then probed using polyclonal antibodies to pyruvate dehydrogenase/decarboxylase E1-α and to phosphorylated E1α (pE1α). The E1α antibody was obtained from MitoSciences/Abcam (Cambridge, Mass.). Antibodies against the phosphorylated serine (pSer293) residue of the E1α subunit were purchased from EMD Millipore/Calbiochem Biochemical (Billerica, Mass.). One milliliter of Luminata Forte western HRP (Millipore Corporation, Billerica, Mass.) substrate reagent was pipetted across the membrane for signal detection in a FluorChem E system (Cell Biosciences, Santa Clara, Calif.).

Glucose Tolerance Test.

Mice were fasted for 6 hours after compound treatment. Ten hours after compound administration, 1.5 g/kg of glucose was delivered intraperitoneally to mice. Tail vein serum samples were collected immediately before and 15, 30, 60 and 120 minutes after the glucose challenge. The glucose levels in serum samples were determined by a glucose meter.

Blood Biochemistry.

Glucose levels were determined with Sigma Diagnostics Glucose (Sigma Aldrich, St. Louis, Mo.). The levels of lactate, cholesterol, and triglyceride were measured by Vitros 250 blood chemistry analyzer (Johnson & Johnson Inc.) in the Metabolic Phenotyping Core in UT Southwestern Medical Center.

Histochemistry of the Liver.

Histological examination of the liver was performed in the institutional Immunohistochemistry Laboratory. Liver tissue was dissected, grossly trim then fixed by immersion for 48 hrs in 4% Formalin/PBS (4% formic acid, 137 mM NaCl, 2.7 mM KCl and 10 mM phosphate buffer, pH 7.5) at 4° C. Liver samples were then transferred to 10% (w/v) sucrose in PBS and incubate at 4° C. for 24 hrs. Tissues were incubated in 18% sucrose in PBS at 4° C. for 24 hours. Finally, samples were transferred to a fresh 18% sucrose solution and embedded in OCT (Optimal cutting temperature compound), cryo-sectioned and stained with Oil Red O.

Statistical Analysis.

Data are shown as mean±standard deviation. Prism 6.0 (GraphPad Inc.) was used to perform the two-tailed Student t test for comparison between groups, and non-linear regression to fit inhibition curves. *p<0.05 is consider significant. p<0.01 and *p<0.001.

Example 2—Results

In Vitro Potencies of Known PDK Inhibitors.

As shown in FIG. 1A, PDK is a homodimer with each monomer consisting of an N-terminal regulatory domain (pink) and a C-terminal nucleotide-binding domain (green). The active-site cleft is formed between sidewalls of these two domains. Based on the PDK-inhibitor structures, the known PDK inhibitors DCA ($IC_{50}$=290 µM) (34) and AZD7545 ($IC_{50}$=87 nM-600 nM) bind to the pyruvate-binding site and the lipoyl-binding pocket, respectively, in the N-terminal domain of PDK (16). The SDZ048-619 derivative, (+)-1-N-[2,5-(S,R)-dimethyl-4-N-(4-cyanobenzoyl) piperazine]-(R)-3,3,3-trifluoro-2-hydroxy-2-methylpropan-amide (compound 3), with $IC_{50}$=16 nM is an analog of AZD7545, and likely also binds to the lipoyl-binding pocket (24). All the above compounds are allosteric PDK inhibitors, since their binding sites in the N-terminal domain are distant from the active-site cleft. In contrast, antibiotic radicicol (FIG. 1B) ($IC_{50}$=230-400 µM) (16) and M77976 ($IC_{50}$=648 µM) (Kukimoto-Niino et al., 2011) dock to the ATP-binding pocket in the C-terminal domains of PDK3 and PDK4, respectively; and are ATP-competitive inhibitors. Except for AZD7545 and compound 3, the above known PDK inhibitors show $IC_{50}$ in the sub-mM range. PDKs and Hsp90 of the GHKL family show conserved chain-folds in the ATP-binding pocket (Dutta and Inouye, 2000); however, radicicol shows a far better binding affinity for Hsp90 (Kd=46.3 nM) than PDK2 (Kd=18,600 nM). Similarly, M77976 also inhibits Hsp90 significantly better than PDK4, with $IC_{50}$ of 4.4 µM for Hsp90 (Dymock et al., 2005) compared with 648 µM for PDK4 (see above).

A Single Functional-Group Substitution Converts an Hsp90 Inhibitor to a PDK-Specific Inhibitor.

Figure 1B:
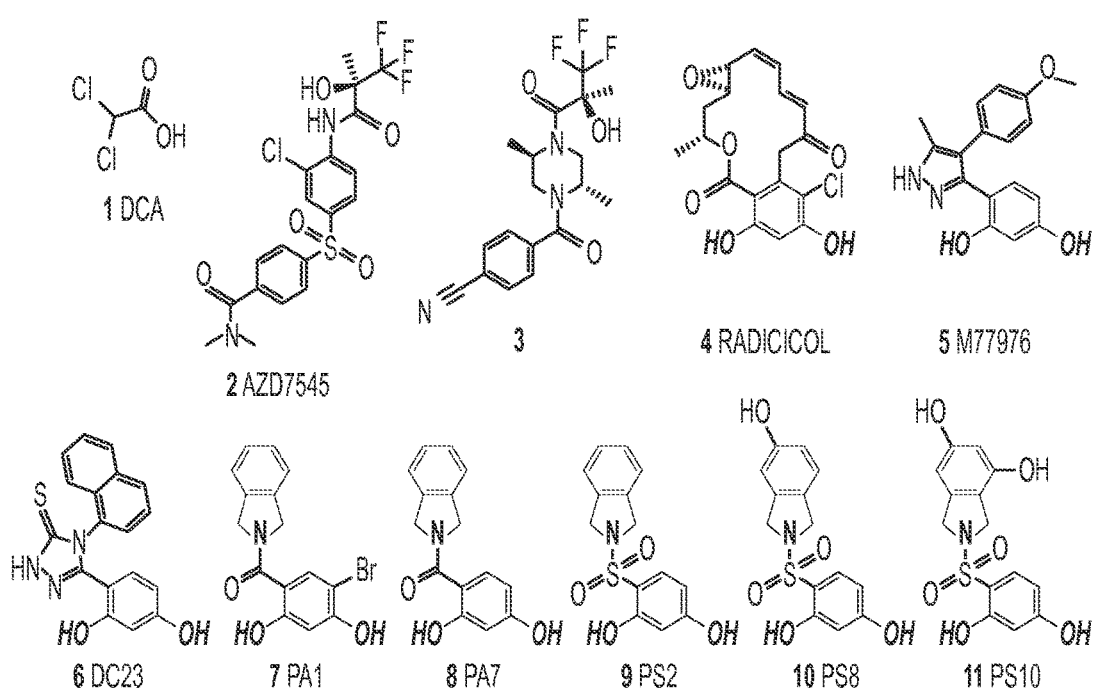

Compound DC23 identified by high-throughput screens performed in this laboratory shows a good potency for inhibition of both PDK4 ($IC_{50}$=0.8 µM) and PDK2 ($IC_{50}$=3.82 µM) (Table 1). However, similar to M77976, DC23 is also an inhibitor for Hsp90 with $IC_{50}$=0.3 µM (Feldman et al., 2009). DC23 shows a much higher binding affinity for Hsp90 than PDK2 with Kd values of 25 nM and 6,760 nM, respectively (Table 1). Radicicol, M77976, and DC23 share a common resorcinol moiety (highlighted in red) in their respective structures (FIG. 1B). In light of the significant conservation in the ATP-binding pocket between PDKs and Hsp90, compounds PA1 and PA7, which were reported as Hsp90 inhibitors (Kung et al., 2010 and Murray et al., 2010), were synthesized. PA1 inhibits both PDK2 ($IC_{50}$=6.78 µM) and PDK4 ($IC_{50}$=1.86 µM) (Table 1). Similarly, PA7 shows $IC_{50}$ values of 5.68 µM and 1.05 µM for PDK2 and PDK4, respectively. Both PA1 and PA7 contain a carbonyl group sandwiched between an isoindoline ring (highlighted in blue) and a resorcinol moiety (in red). As expected, PA1 preferentially binds to Hsp90 (Kd=9.0 nM) over PDK2 (Kd=3,570 nM). PA7, with the 5-bromo-group removed from the resorcinol ring, is also a far more potent ligand for Hsp90 (Kd=27.3 nM) than PDK2 (Kd=1,827 nM). Remarkably, a single substitution of the carbonyl group in PA7 with a sulfonyl group practically converts the potent Hsp90 inhibitor PA7 to a PDK-specific inhibitor in PS2. The $IC_{50}$ is 2.11 µM for PDK2; more significantly, the Kd values are 711 nM for PDK2 and 50,900 nM for Hsp90. Based on these new Kd values, the change from the carbonyl group in PA7 to the sulfonyl group as in PS2 represents 4,791-fold shift in binding affinities in favor of the PDK2. The addition of the 5-hydroxyl group to the isoindoline ring in PS8 results in improved IC50 values for both PDK2 (1.07 µM) and PDK4 (1.10 µM) (Table 1). The relative binding affinities for PDK2 (Kd=426 nM) and Hsp90 (Kd=60,100 nM) become further more favorable for PDK2. The introduction of a second hydroxyl group to the isoindoline ring generates PS10 with significantly better $IC_{50}$ and Kd values than those for PS8 for PDK2 and PDK4. The Kd value of 239 nM for PS10 binding to PDK2 is the lowest among the ATP-competitive PDK inhibitors.

Structures of PDK2-Inhibitor Complexes Reveal a Distinct Ligand-Binding Mode.

PDK2 crystals were soaked with 0.25-0.5 mM concentrations of various PDK inhibitors. Crystals of PDK2-inhibitor complexes diffracted to 1.70-1.95 Å resolutions. All residues were in the most favorable and allowed regions of the Ramachandran plot. The final models show excellent geometry and residual statistics (Table 2).

FIG. 2A shows a high degree of conservation in the nucleotide-binding domain between PDK2 and Hsp90, when the PDK2-PA7 structure (in green, this study) is superimposed with the published Hsp90-PA7 structure (in orange) (Kung et al., 2010). However, the size and contour of the ATP-binding pocket in Hsp90 significantly differ from those of the corresponding pocket in PDK2. In Hsp90, the ATP-binding pocket shows a narrow opening of 5.2 Å leading to a deep tunnel-like surface (FIG. 2B). By comparison, the ATP-binding pocket in PDK2 shows a wider opening of 7.5 Å with a shallow cavity (FIG. 2C). These differences form the basis for the structure-based design of PDK-specific inhibitors. PA7 binds to the ATP-binding pocket of Hsp90 with the isoindoline ring in a planar conformation (FIG. 2B). In contrast, the same ring in PDK2-bound PA7 is tilted toward the α10 helix (FIG. 2C). The different conformations in the isoindoline ring become apparent when the Hsp90-bound PA7 structure is superimposed with the PDK2-bound PA7 structure (FIG. 2D). The more relaxed planar orientation of the isoindoline ring in Hsp90 explains, in part, the drastically higher binding affinity of Hsp90 for PA7 than PDK2 (Table 1). In PDK2, PA7 interacts with conserved Leu252 in the N box, Asp290 and Gly294 in the G1 box, and Thr354 in the G3 box (FIG. 2F). Equivalent contacts are observed in the Hsp90-PA7 structure (FIG. 2E). Similar interactions are also present in the PDK2-PS2 structure (FIG. 2G). The substitution of a carbonyl group in PA7 with a sulfonyl group in PS2 retains the favorable position of the isoindoline ring in PDK2-bound PS2 (FIG. 2D). On the other hand, the tetrahedral bond angles of the sulfonyl group in PS2, when bound to Hsp90, can conceivably cause the isoindoline ring to clash with the α2 helix in Hsp90, resulting in the markedly reduced affinity of Hsp90 for PS2 compared to PA7 (Table 1). The incorporation of 5-OH group to the isoindoline ring in PS8 promotes interactions of the hydroxyl group with Glu262, which is unique for PDK isoforms, making PS8 a better PDK inhibitor than PS2 (Table 1). The presence of two OH groups in the isoindoline ring in PS10 permits the second OH group to contact, through a water molecule, Asn255 of the N box while maintaining the contact with Glu262 (FIG. 2I). The additional interactions with Asn255 through the second OH group likely foster the better $IC_{50}$ and Kd values of PS10 compared to PS8. Stereo views of the interaction between the inhibitors and PDK2 can be found in FIG. 8.

PS-Series Inhibitors Show Favorable Binding Enthalpies for PDK2.

Figure 3A:
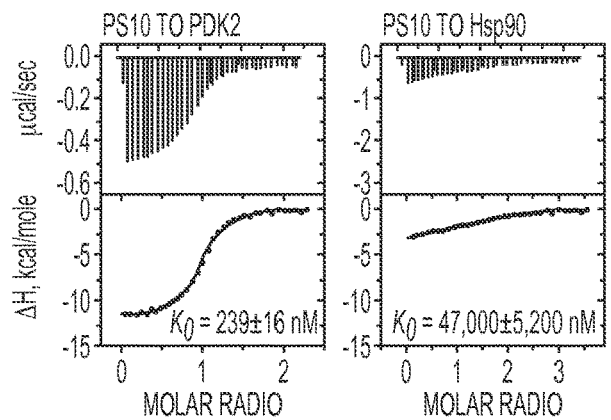
FIGS. 3A-B. Thermodynamics analysis of inhibitor binding to PDK2 and Hsp90.
Figure 3B:
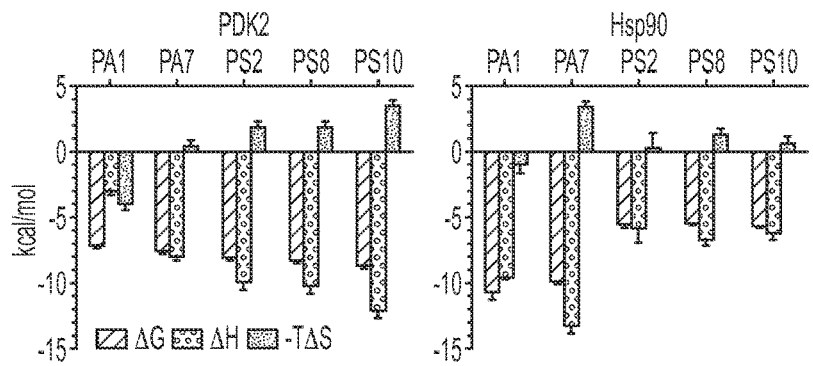

The binding of PDK inhibitors to PDK2 or Hsp90 was measured by isothermal titration calorimetry (ITC). The fitting of binding isotherms (FIG. 3A) showed a distinctly higher affinity of PS10 for PDK2 (Kd=239 nM) than for Hsp90 (Kd=47,000 nM). The binding enthalpy (ΔH in kcal/mol) of PS10 for Hsp90 is also shown much smaller than that for PDK2 (FIG. 3A). The development of compounds from PA1 toward PS10 on the same chemical scaffold was accompanied by the steadily more favorable (i.e., more negative) thermodynamic signatures in terms of binding enthalpies (ΔH) and Gibbs binding energies (ΔG), when titrated into PDK2, although the term of binding entropies (−TΔS) become less favorable (or more positive) (FIG. 3B, left panel). These gains in binding enthalpy indicate the progressively more favorable interactions between PDK2 and the inhibitors as PA1 is evolved into PS10, despite the accompanied relatively small entropic penalties (Freire et al., 2008). In contrast, the conversion from carbonyl group-containing compounds (PA1 and PA7) to the sulfonyl group-harboring counterparts (PS2, PS8, and PS10) results in significant losses of binding enthalpies for Hsp90 (FIG. 3B, right panel). The favorable binding enthalpies further support the vastly improved selectivity of PS8 and PS10 as PDK inhibitors over the parental compound PA1.

PS-Series Inhibitors Show High Selectivity for PDK Isoforms.

Figure 4:
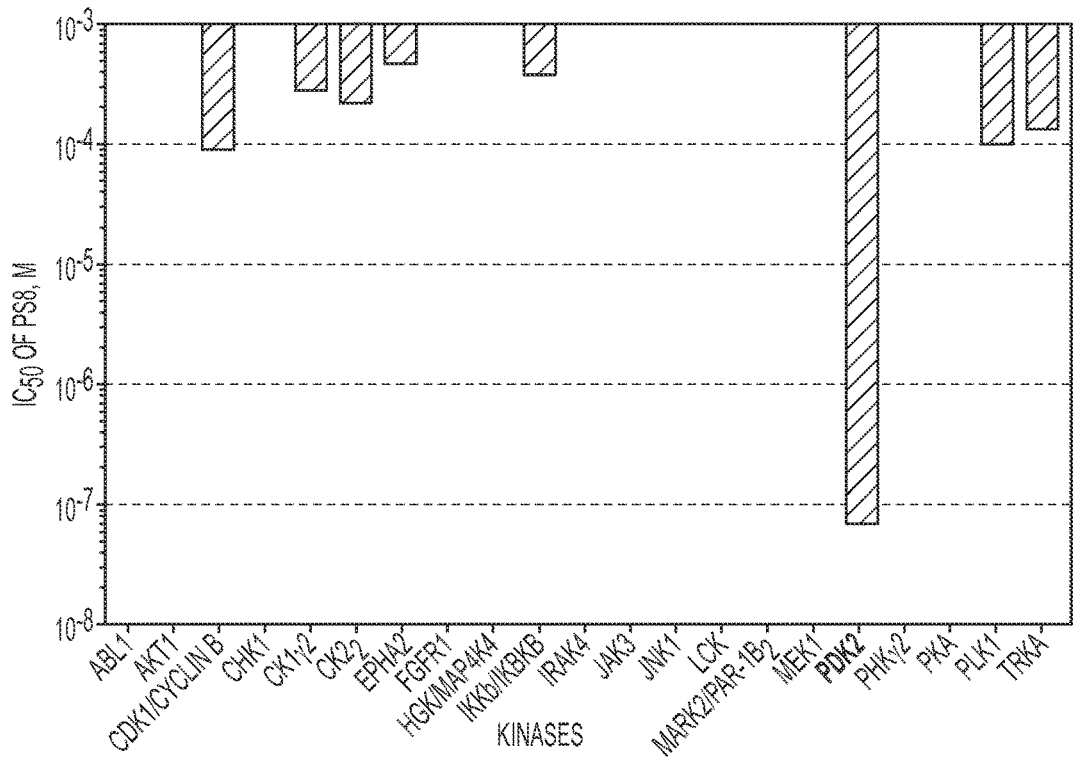
FIG. 4. Kinase profiling of compound PS8. Inhibition of the 21 representative kinases, including PDK2, in the Human Kinome by PS8 were measured in the concentration range of 15 nM to 300 μM. $IC_{50}$ values for each kinase were derived from individual inhibition curves. The $IC_{50}$ for PDK2 is at least 3 order magnitudes lower than next lowest value for CDK1/cyclin B.

The selectivity of PS8 was studied by determining $IC_{50}$ for the inhibition of a 21-kinase panel including PDK2. PS8 shows the lowest $IC_{50}$ of 70 nM for PDK2 under the assay conditions with myelin-binding protein as an artificial substrate (FIG. 4). All other kinases on the panel show at least 3 orders of magnitude higher $IC_{50}$ values for inhibition by PS8. The results established the specificity for PS8 as a PDK2 inhibitor. To dissect the specificity of PS-series inhibitors against the four PDK isoforms, in vitro kinase assays were performed with or without the E2/E3BP core of PDC. PS8 inhibits all four isoforms at sub-micromolar to low micromolar range (Table 3). Except PDK4, PDK isoforms anchor to the E2/E3BP of PDC for optimal kinase activity in vivo. In the presence of E2/E3BP, PS8 is a more effective inhibitor for all PDK isoforms than in the absence of E2/E3BP, particularly for PDK3. PS10 shows the similar $IC_{50}$ values for the inhibition of four PDK isoforms when assayed in absence of E2/E3BP (Table 3). The above results, taking together, indicate that both PS8 and PS10 are pan-PDK inhibitors.

To assess possible toxicity of PS-series compounds due to non-specific interactions, HeLa and HBEC30 cells were titrated with PS8. The $IC_{50}$ values for the growth inhibition of HeLa and HBEC30 cells by PS8 are 223 nM and 253 nM, respectively. The toxicity of PS8 is 100-fold less potent than cycloheximide in both cell lines. Similarly, PS10 shows an $IC_{50}$ of 284 μM for the growth inhibition of HeLa cells. These results suggest that the toxicity of PS8 and PS10 is minimal in vivo.

Pharmacokinetic Properties of PS8 and PS10.

PS8 and PS10 both show half-lives of greater than 240 min in vitro in hepatic S9 fractions (data not shown), which suggest that neither is extensively metabolized by phase I oxidative or reductive metabolism. In vivo, both compounds show a rapid distribution phase, followed by a slower terminal elimination phase after IP delivery. The pharmacokinetic parameters on Table 4 show that the distribution and elimination of PS8 was slightly more rapid than PS10, possibly due to its somewhat more hydrophobic nature. Both compounds show good plasma exposure (AUClast) as well as a volume of distribution, which is suggestive of modest tissue penetration (Table 4).

PS10 Stimulates PDC Activity in Tissues of DIO Mice.

Figure 5A:
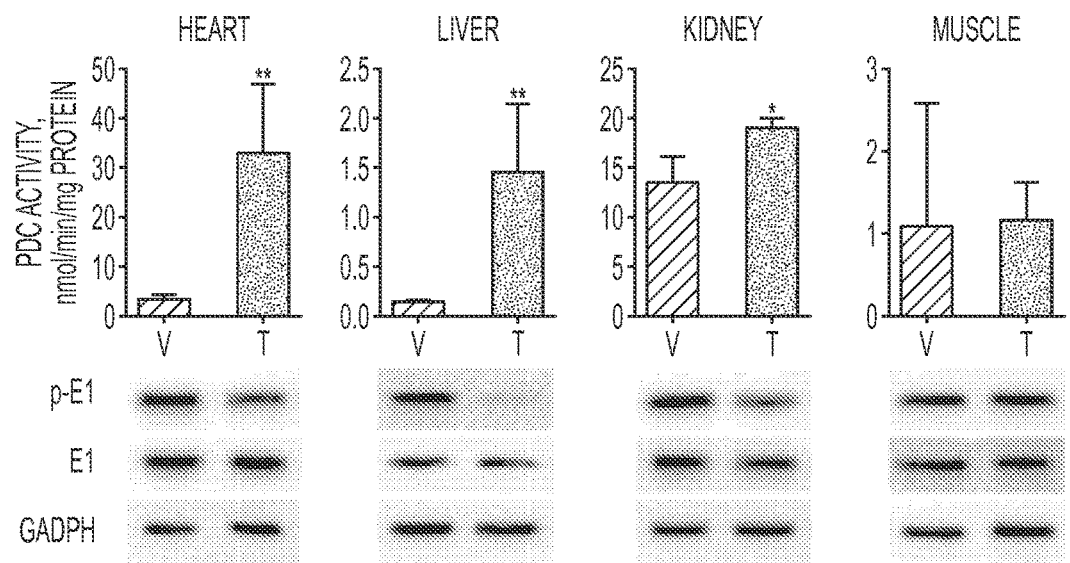
FIGS. 5A-B. Enhanced PDC activity with reduced phosphorylation level in PS10-treated DIO mice.
Figure 5B:
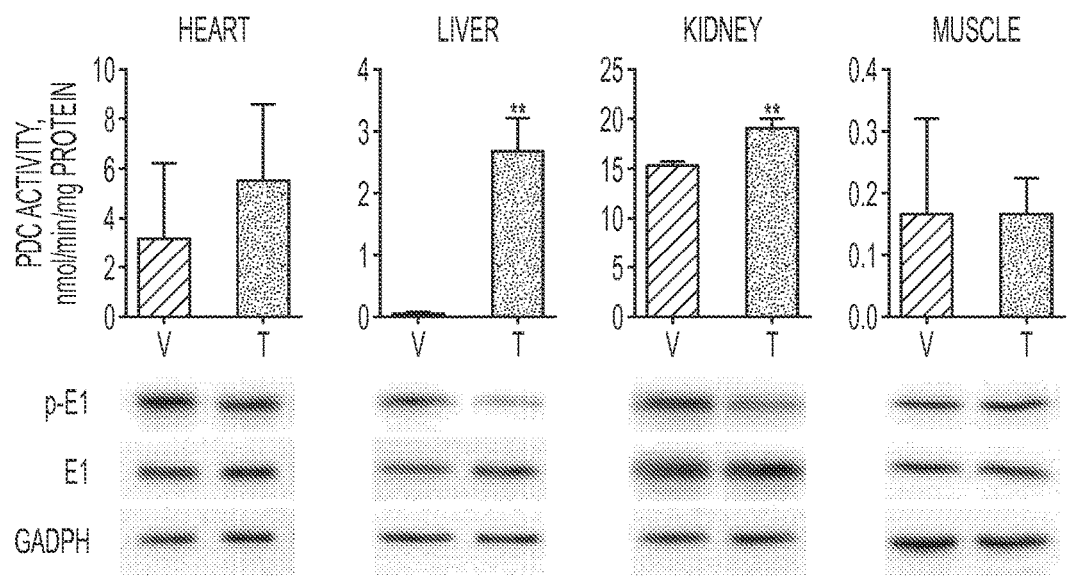

Both PS8 and PS10 show good $IC_{50}$ for the four PDK isoforms (Table 3); however, PS10 was chosen for in vivo studies because of its better solubility in DMSO used in the formulation. Male C57BL/6J mice were fed a high-fat diet for three weeks to produce DIO model with impaired glucose tolerance. These DIO mice were initially treated with a single dose of either vehicle or PS10 (70 mg/kg) by IP injection. The animals were sacrificed 10 h later in the early morning in the fed state. Maximal enhancement of PDC activity by PS10 in tissues was achieved under these conditions. Tissues (heart, liver, kidneys and quadriceps muscle) were harvested and analyzed for PDC activity by the radiochemical assay with $[1-^{14}C]$pyruvate as a substrate. FIG. 5A (top) shows that PDC activity was low in the heart and liver from vehicle-treated DIO mice. PS10 treatments result in 11-fold and 23-fold higher PDC activity in heart and liver, respectively than the vehicle-treated. There is a 1.4-fold enhancement of PDC activity in PS10-treated kidneys compared with vehicle-treated. In contrast, there is no difference of PDC activity in quadriceps muscle between PS10-treated and vehicle-treated DIO mice. The elevated PDC activity correlates with significantly decreased amounts of the phosphorylated E1α subunit in heart and liver of PS10 treated DIO mice compared with vehicle-treated (FIG. 5A, bottom). These results corroborate that PS10 functions as a PDK inhibitor in vivo to attenuate phosphorylation levels of the E1α subunit, leading to stimulated PDC activity in DIO mice. The increased PDC activity is not due to enhanced phosphatase activity, since PS10 at up to 1 mM is without effect on PDP1 activity in vitro. In the next series of experiments, DIO mice were treated with vehicle or PS10 (70 mg/kg/day) for three days and tissues were collected for biochemical studies. As shown in FIG. 5B, except in the heart, PDC activity profiles and the phospho-E1α subunit level are similar between the single-dose and multiple-dose treatments of DIO mice with PS10. In the heart, the prolonged PS10 treatment appears to attenuate the enhancement of PDK activity compared to the single administration of the compound.

PS10 Increases Glucose Tolerance and Lessens Hepatic Steatosis in DIO Mice.

Figure 6A:
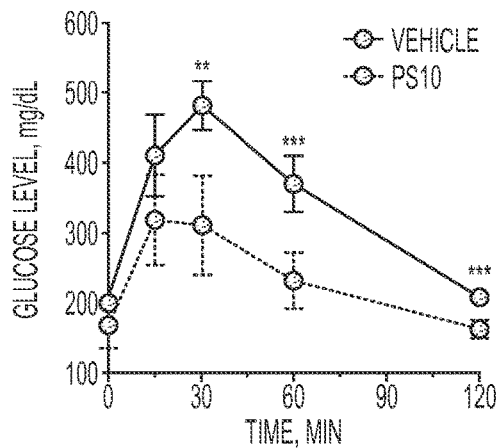
FIGS. 6A-H. Glucose- and lipid-controlling properties of PS10.
Figure 6B:
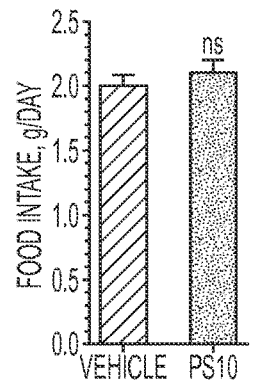
Figure 6C:
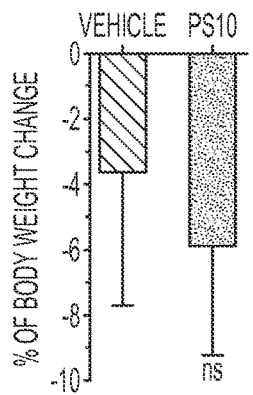
Figure 6D:
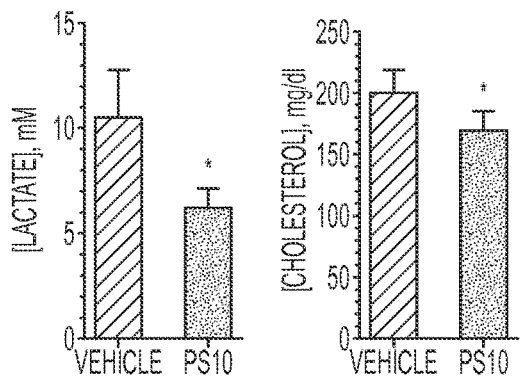
Figure 6E:
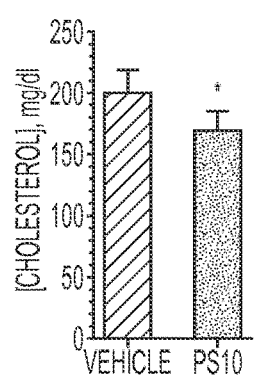
Figure 6F:
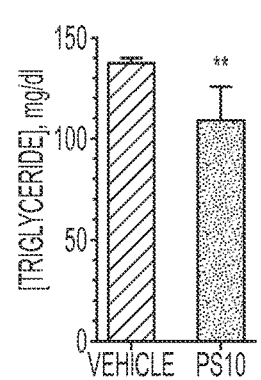
Figure 6G:
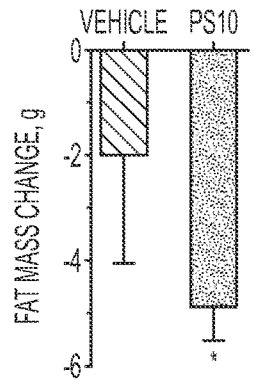
Figure 6H:
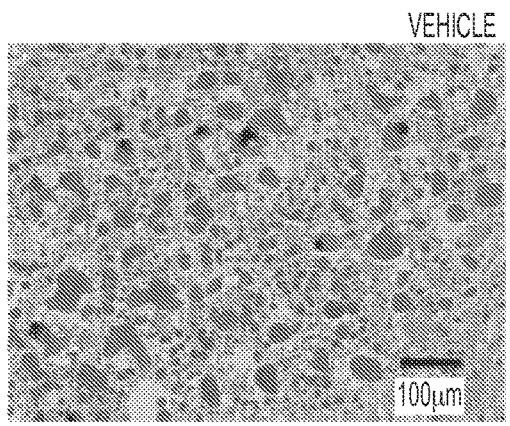
Figure 6H:
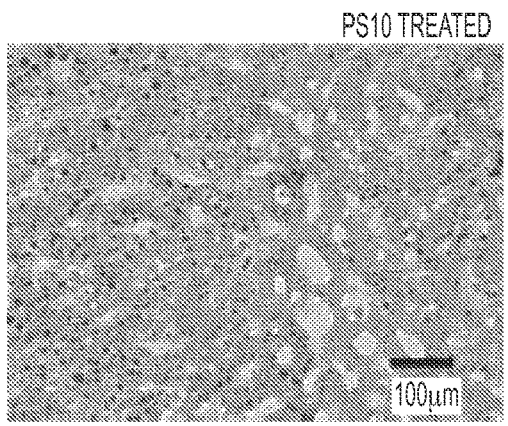

DIO mice on a high fat diet for 10 weeks were treated with vehicle or PS10 (70 mg/kg/day) by IP injections for four additional weeks and subjected to a glucose tolerance test. The vehicle and PS10 treatments were continued for 2 more days and, animals were sacrificed in the early morning while in the fed state, and tissues and blood were collected for biochemical studies. Results from the glucose tolerance tests (FIG. 6A) show that when challenged with 1.5 g/kg of glucose, the plasma glucose level in the vehicle-treated control was at 200 mg/dl at 0 min, peaked at 482 mg/dl at 30 min and reduced to 210 mg/dl at 120 min. In PS10-treated DIO mice, the glucose level at 168 mg/dl at 0 min was lower than that in vehicle-treated animals, reached 312 mg/dl at 30 min and returned to 163 mg/dl at 120 min. The two groups of animals show significant differences in the glucose levels at 30, 60, and 120 min, with lower glucose levels uniformly observed in the PS10-treated DIO mice. The data therefore suggest that the PS10 treatment increases glucose tolerance over vehicle-treated DIO mice. Notably, there are no significant differences in food intake (FIG. 6B) and body weight (FIG. 6C) between the vehicle- and PS10-treated animals. DIO mice treated with PS10 also showed significantly lower plasma lactate (FIG. 6D), cholesterol (FIG. 6E) and triglycerides (FIG. 5F) levels and a reduction in fat-mass (FIG. 6G), compared with the mice treated with vehicle. Moreover, larger amounts of fat were present in the liver of the vehicle-treated DIO mice compared with PS10-treated, when the liver slices were stained with Oil Red O (FIG. 6H). The accumulated hepatic fat was primarily macrovesicular in vehicle-treated DIO mice and became microvesicular in the PS10-treated counterpart.

Molecular Mechanisms for Reduced Hepatic Steatosis in PS10-Treated Mouse Models.

Figure 10A:
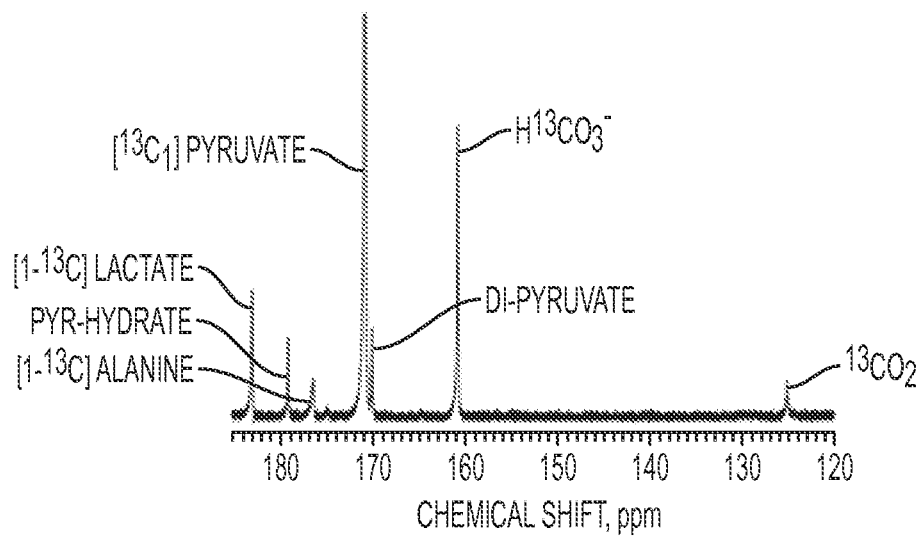
FIGS. 10A-B. PDC flux in perfused hearts from lean and DIO mice detected by hyperpolarized $^{13}$C NMR.
Figure 10B:
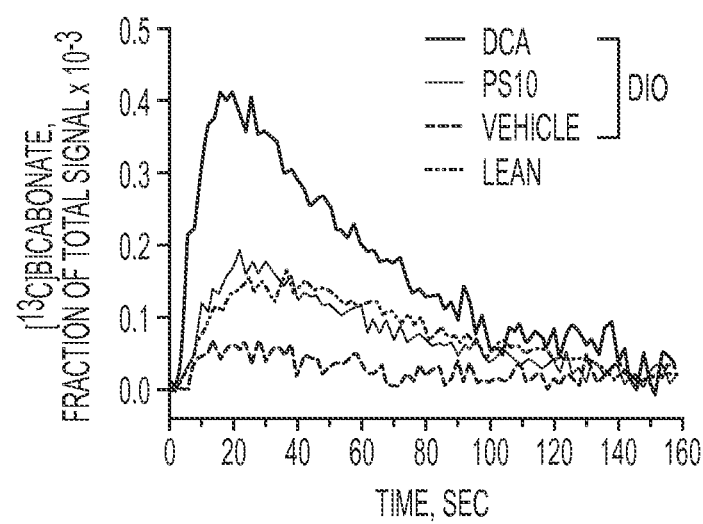

The inventors have employed hyperpolarized (HP) [1-$^{13}$C]pyruvate to directly measure PDC flux in perfused heart by $^{13}$C NMR (Merritt et al., 2011; 2007). This state-of-the-art method enhances the sensitivity of NMR by >10,000-fold and enables the study of cardiac and hepatic metabolism ex vivo. Metabolism of [1-$^{13}$C]pyruvate to [1-$^{13}$C]alanine, [1-$^{13}$C]lactate, H$^{13}$CO$_3^-$ and $^{13}$CO$_2$ were detected in real time by $^{13}$C NMR spectra, following the injection of 2 mM HP [1-$^{13}$C]pyruvate into perfused heart (FIG. 10A). Pyruvate could enter the TCA cycle via pyruvate carboxylation, but pyruvate cycling is negligible in heart (Merritt et al., 2011). Therefore, the appearance of [$^{13}$C]bicarbonate (H$^{13}$CO$_3^-$) directly reflects the flux through PDC (Merritt et al., 2007), which is quantified by the integrated scaled intensity of H$^{13}$CO$_3^-$ as a function of time (FIG. 10B). The result shows that PDC flux directly measured in heart from vehicle-treated diet-induced obese (DIO) mice (blue line) (n=4) is drastically reduced compared to lean control mice (green line) (n=4). The decreased PDC flux is explained by the up-regulation of PDK4 expression in DIO mice (Crewe et al. 2013). The treatment with a single dose of the classic PDK inhibitor dichloroacetate (DCA) (250 mg/kg) (FIG. 1B, black line) results in a marked increase in cardiac PDC flux in DIO mice; the high dose of DCA was used owing to the high IC$_{50}$ value. A smaller increase is obtained with one dose of PS10 (70 mg/kg) (FIG. 10B, red line). These preliminary data suggest that glucose oxidation is markedly reduced in obesity, which can be restored by suppressing PDK activity with DCA or PS10. The small but significant increase of PDC flux in a single-dose PS10-treated heart is consistent with results of the single-dose treatment the inventors reported previously (Tso et al., 2014).

Figure 11A:
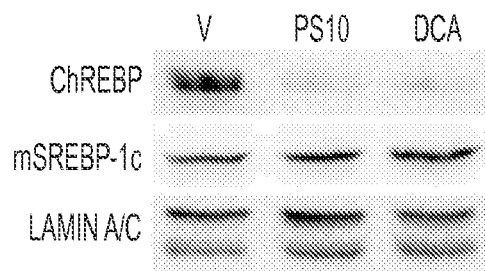
FIGS. 11A-B. Increased glucose oxidation attenuates hepatic ChREBP protein levels in PDK inhibitor-treated DIO mice Animals at 20-22 weeks old were treated with PDK inhibitor PS10 (40 mg/kg/day) or DCA (200 mg/kg/day) by mini-pumps for 5 days. Lamin and GAPDH are loading controls; p-E1, phosphorylated decarboxylase-α subunit of PDC; mSREBP-1c, mature SREBP-1c.
Figure 11B:
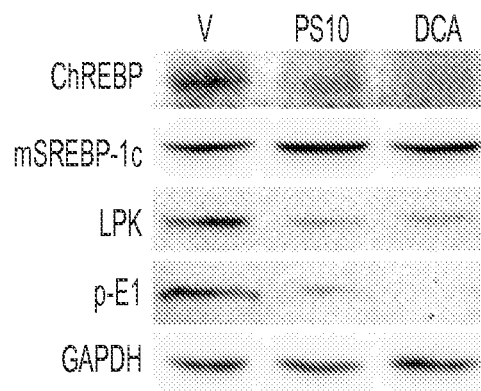
Figure 12A:
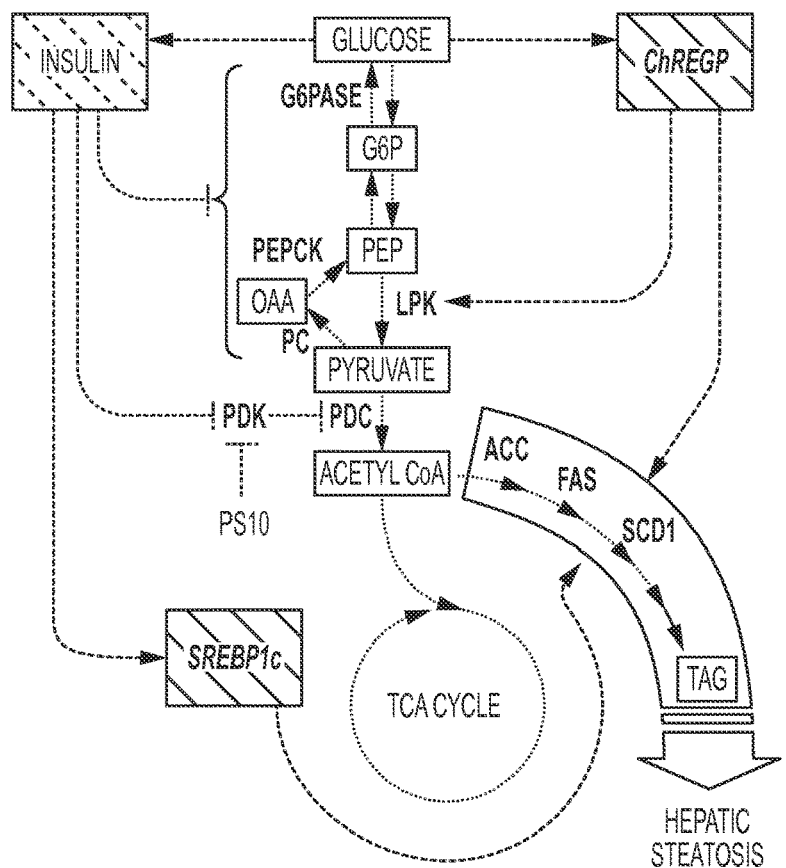
FIGS. 12A-B. Increased glucose oxidation through PDC flux reduces hepatic steatosis by attenuating ChREBP-mediated lipogenesis.
Figure 12B:
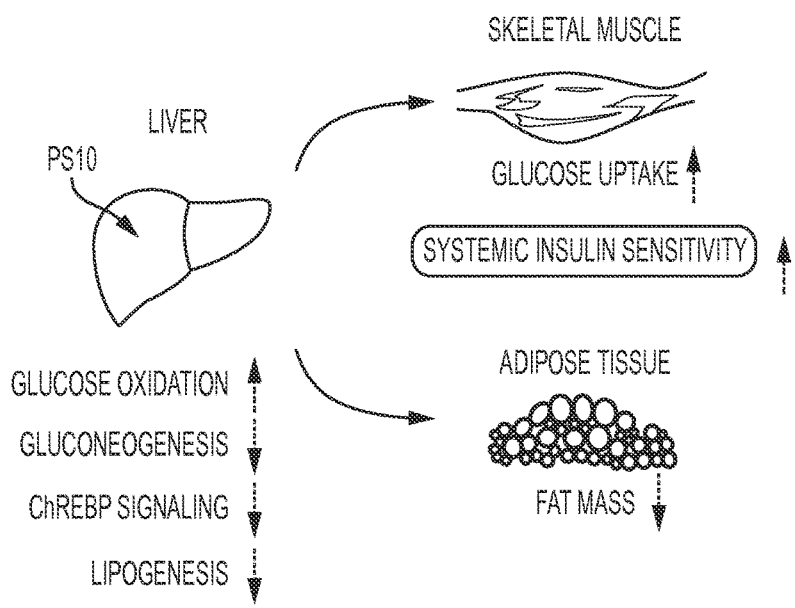

The inventors recently obtained the first evidence that protein levels of the transcription factor carbohydrate response element-binding protein (ChREBP) from the hepatic nuclear fractions are drastically decreased in DIO mice treated with PDK inhibitors PS10 and DCA, whereas the protein level of nuclear mature SREBP-1c is unchanged (FIG. 11A). The antibody (from Santa Cruz) against the 95-kilodalton ChREBP is highly specific; no signal was detected in hepatic nuclear fractions from ChREBP KO mice. The reduced nuclear ChREBP protein levels correlate with curtailed liver-type pyruvate kinase (LPK) (FIG. 11B), the marker glycolytic enzyme tightly regulated by ChREBP[5]. The increased PDC flux is indicated by diminished phosphorylation of the decarboxylase/dehydrogenase (E1)-α subunit of this enzyme complex (FIG. 11B); while the expression of this subunit is not affected (not shown). The glucose-sensitive transcription factor ChREBP discovered and cloned by the Uyeda group in 2001 (Yamashita et al., 2001) has emerged as a central regulator of lipogenesis in liver (Uyeda and Repa, 2006; Filhoulaud et al., 2013; Denechaud et al., 2008) and β-cells (Cha-Molstad et al., 2009; Kibbe et al., 2013) at the transcriptional level (Uyeda and Repa, 2006; Filhoulaud et al., 2013; Denechaud et al., 2008). Interestingly, the deletion of this transcription factor improves hepatic steatosis in ob/ob mice (Iizuka et al., 2006) and augments PDC flux in otherwise wild-type mice through reduced phosphorylation (Burgess et al., 2008), similar to that observed in PS10-treated DIO mice (Tso et al., 2014). Therefore, the inventors propose that increased glucose oxidation through PDC flux lowers hepatic glucose concentrations and attenuates nuclear ChREBP-mediated de novo lipogenesis in liver (FIG. 12A). The liver-targeted inhibition of PDK activities by PS10 offers an opportunity to investigate the putative crosstalk between liver and extra-hepatic tissues (e.g., skeletal muscle and white adipose tissue), which could result in the restoration of systemic insulin sensitivity in obese animal models (FIG. 12B).

Using Structure-Based Strategies to Improve Potency and Selectivity of PDK Inhibitors.

Figures 13A, 13B:
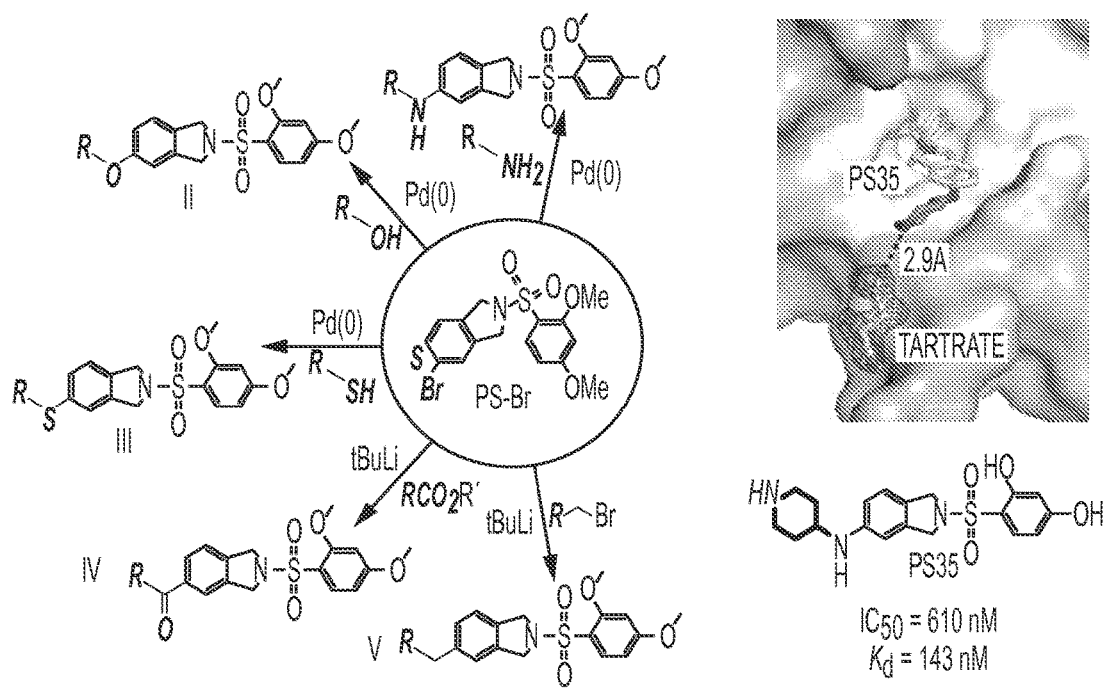
FIGS. 13A-B. Inhibitor designs targeting the entrance region of ATP-binding pocket.

Two approaches are being used to develop new generation of better PDK inhibitors. First, the inventors sough to target the entrance region of the ATP-binding pocket. To expand the repertoire of the PS-series compounds, they have synthesized a new precursor PS—Br (circled), which allows for efficient production of potential new PDK inhibitors (Classes I-V) (FIG. 13A). This can be accomplished through the installation of different R groups to the 5 position of the bicyclic isoindoline moiety using various coupling reagents (R—NH$_2$, R—OH, R—SH, R—COOR', and RCH$_2$Br). Different strategies such as palladium(0)-catalyzed cross-coupling or tert-butyllithium-mediated electrophilic addition will be used for these transformations. One of the PS—Br derivatives PS35 (Class I, R=a piperidine ring) shows IC$_{50}$ of 610 nM and K$_d$ of 143 nM (FIG. 13B), which are significantly better than PS10. In the crystal structure, PS35 binds to ATP-binding pocket (in yellow), with the piperidine ring (in magenta) contacting a small hydrophobic patch at entrance of the pocket (FIG. 13B). On the other hand, PDK2 structures determined in this laboratory invariably show a good electron density for tartrate (FIG. 13B, blue mesh) forming specific hydrogen bonds with residues in an area close to the piperidine ring of bound PS35. During PDK2 crystallization, a high concentration of ammonium tartrate was added to the crystallization buffer. The inventors' strategy is to synthesize conjugates between PS35 and tartrate (or tartrate-like) moieties (FIG. 13B, dotted line). A conjugation of two bound fragments often results in an exponentially amplified binding affinity, according to the principle of fragment-based drug design (Scott et al., 2012). Flexible linkers will be selected which allow the maintenance of an approximately 2.9-Å distance between the piperidine group and the tartrate or a tartrate-like moiety.

Figures 14A, 14B, 14C:
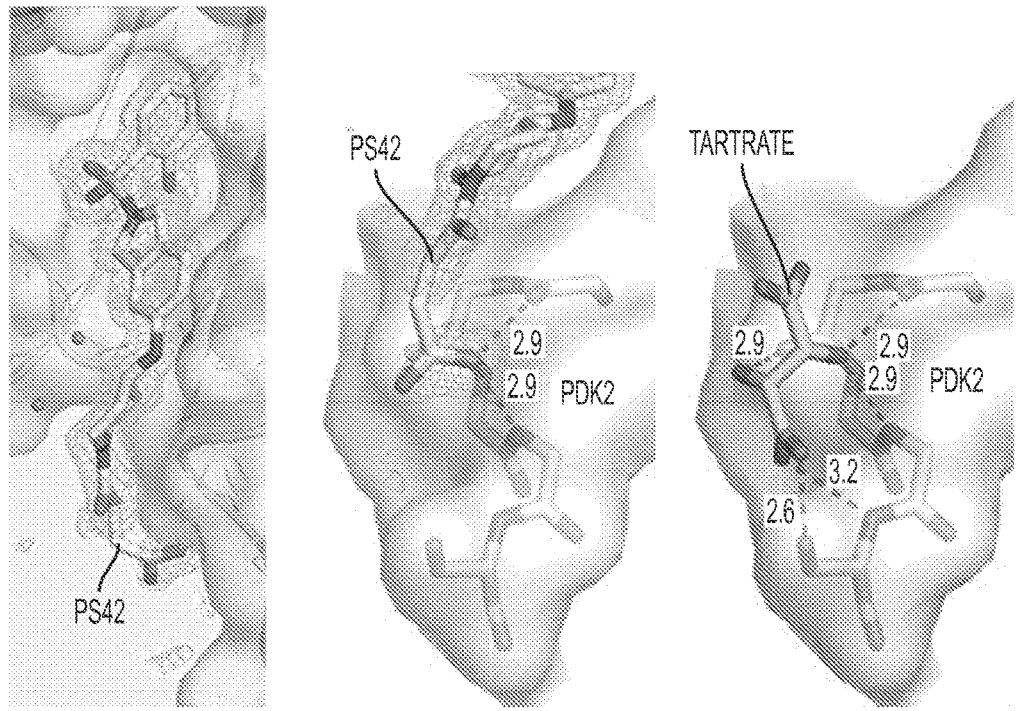
FIGS. 14A-C. Binding of PS42 and tartrate to PDK2.

Several compounds have been synthesized (Table 5) based on this approach and tested. Although none of these new derivatives showed better affinity on PDK2, protein crystal structures with those inhibitors indeed provided useful information for further development. For example, as shown on FIGS. 14A-C, the extended moiety of PS42 is correctly positioned in the pocket and able to re-establish part of the tartrate-PDK2 interaction. Compounds which take the full advantage of that interaction and therefore have better potency are expected to be available in near future.

Second, the inventors have attempted extension into the phosphate region of the ATP-binding pocket. FIG. 15A shows that the bound PS10 spans both the entrance and adenine regions of the ATP-binding pocket in PDK2. The resorcinol ring (dashed circle) of the bound PS10 juxtaposes with the adenine moiety of the superimposed bound ATP. However, the vast positively charged (in blue) phosphate region, which is normally occupied by the triphosphate moiety of ATP, is void in the PDK2-PS10 structure. Thus, a parallel strategy to the approach 1 is to add hydrophilic groups to the PS-series compounds, which could extend into the unoccupied phosphate region. The inventors hypothesize that additional interactions between the inserted well-positioned hydrophilic groups and amino acid residues in the phosphate region will significantly increase binding affinities of the modified PS-series compounds. To add functional groups to the PS-series compounds, the inventors propose to use imino-derived isoindolines as the starting materials for synthesis (FIG. 15B, the upper-left compound). For the Class I synthetic route, the R1 functional group can be an alkyl, carbonyl or carboxyl group, with the installation accomplished by a sec-butyllithium (sBuLi)-mediated nucleophilic substitution. On the Class II path, an aromatic ring is installed on the isoindoline through a palladium(0)-catalyzed cross-coupling with aromatic bromide (ArBr). Upon incorporation of the resorcinol and sulfonyl moieties, both Class I and Class II synthetic routes lead to candidate PDK inhibitors of the PS series with R1 modifications (FIG. 15B, the rectangular box). Finally, the flexible lid regions in PDK structures become partially ordered through interaction with the triphosphate moiety of bound ATP (Kato et al., 2005; Knoechel et al., 2006). A ligand-induced disorder-to-order transition is usually accompanied by the loss of favorable binding entropy[16]. Therefore, the design of R1 modifications will be such that the installed groups do not result in ordering of the ATP-lid region.

Two recent publications have demonstrated the potential of having PDK inhibitor extending into the phosphate region of that pocket by synthesizing such PDK inhibitors with relatively good potency (Meng et al., 2014; Moore et al., 2014). With these newly learned information, list of novel compounds will be synthesized and tested (FIG. 16).

Example 3—Discussion

Figure 7:
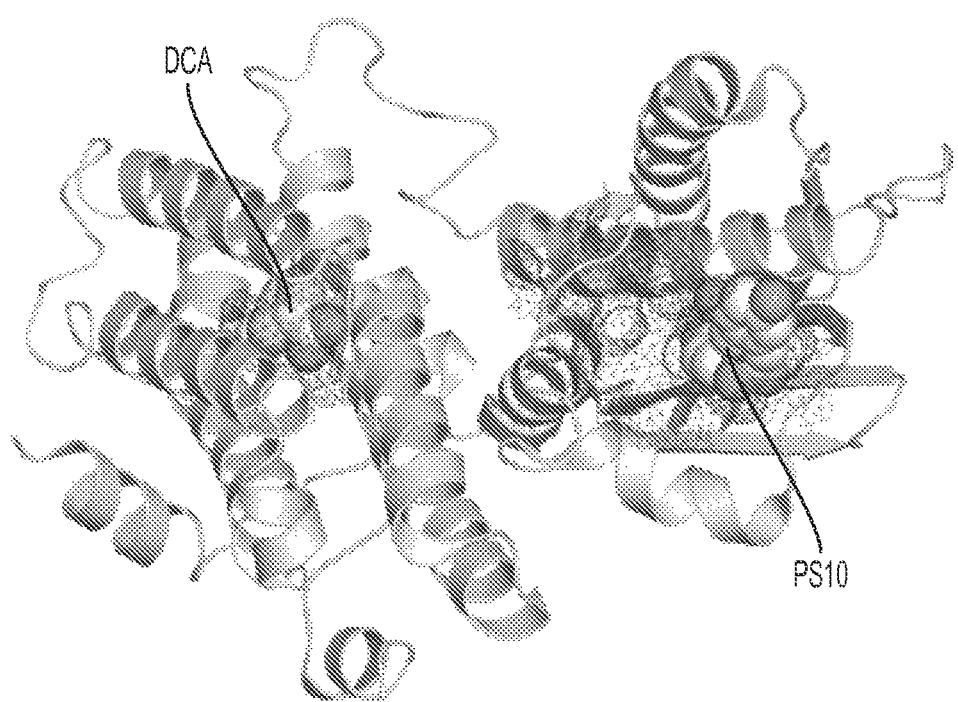
FIG. 7. Calculated volumes of the DCA-binding and ATP-binding pockets in PDK2. The N-terminal domain of the PDK2 monomer with the allosteric site occupied by DCA is derived from coordinates of PDB code: 2BU8. PDK inhibitor PS10 was modeled into the ATP-binding pocket in the C-terminal domain of the same monomer, according to the PS10 coordinates of PDB code: 4MPN from this study. The volumes of the DCA-binding (211 Å3) and ATP-binding (865 Å3) pockets, as represented by blue meshes, were computed using program CASTp (46).
Figure 8A:
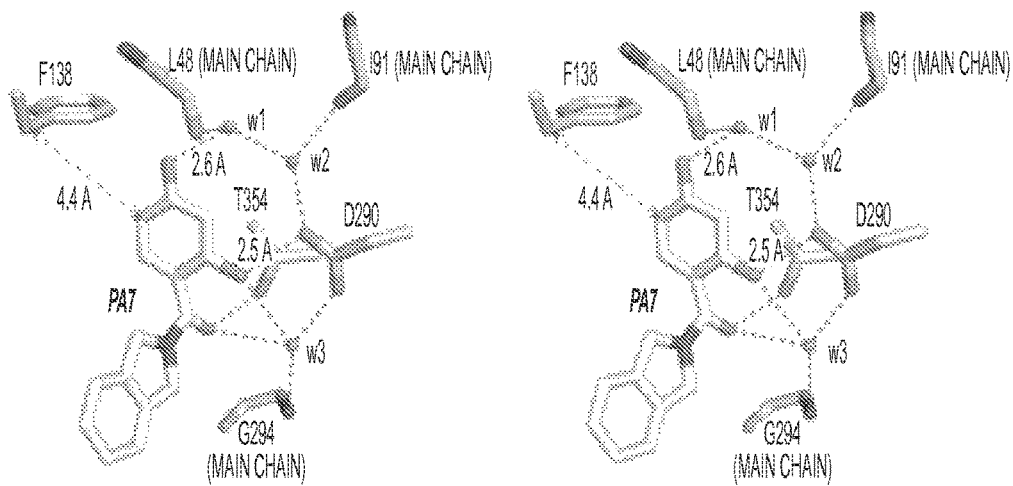
FIGS. 8A-F. Stereo views of inhibitor-binding pockets in PDK2 and Hsp90.
Figure 8B:
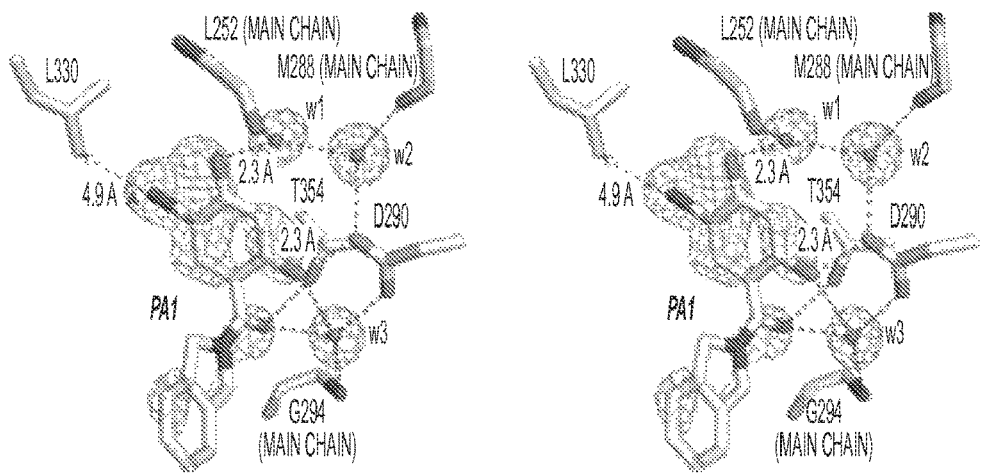
Figure 8C:
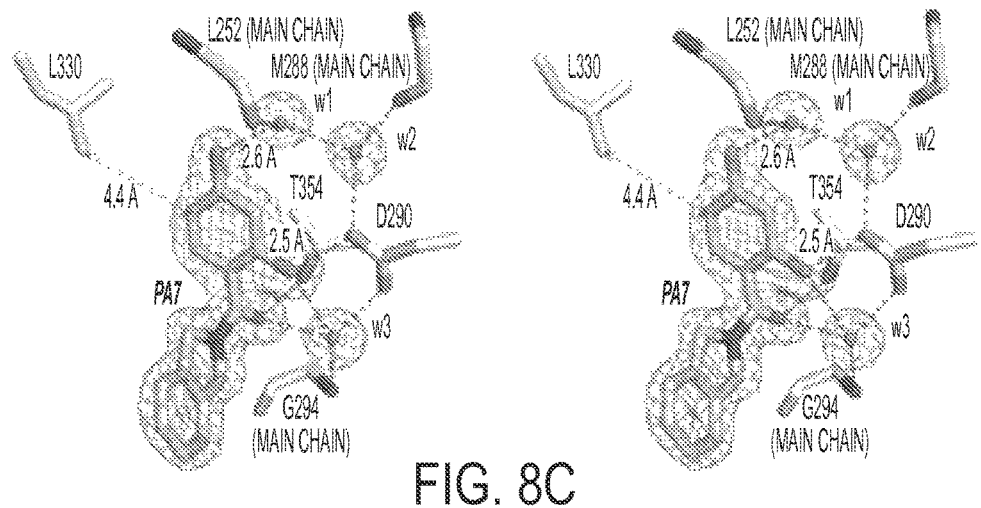
Figure 8D:
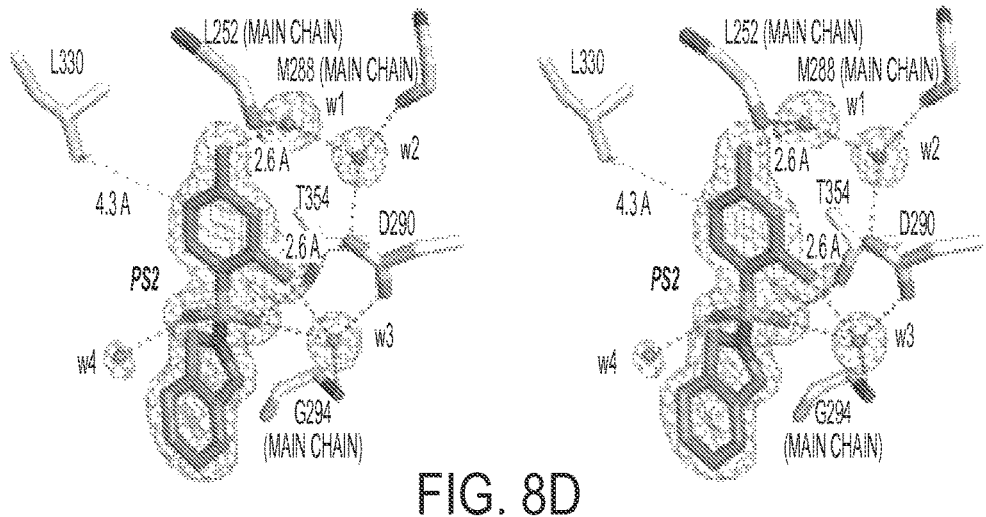
Figure 8E:
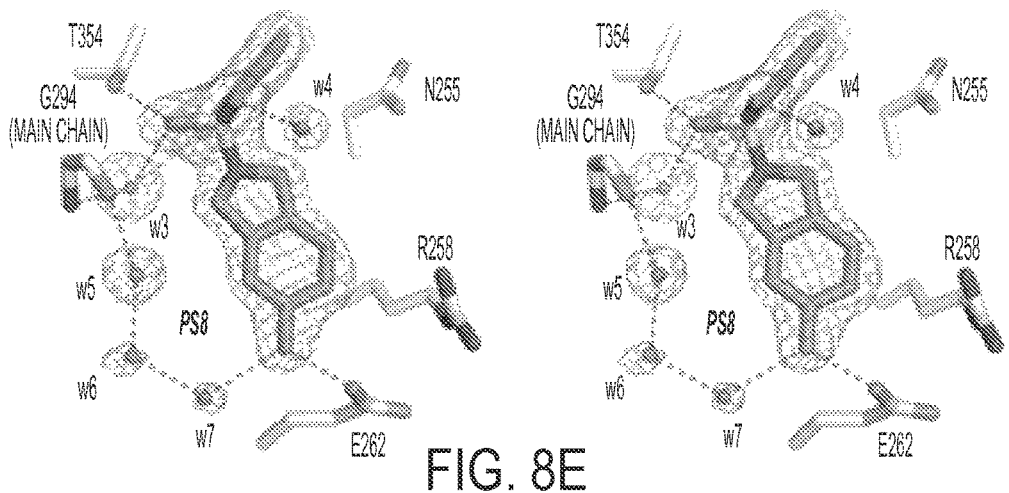
Figure 8F:
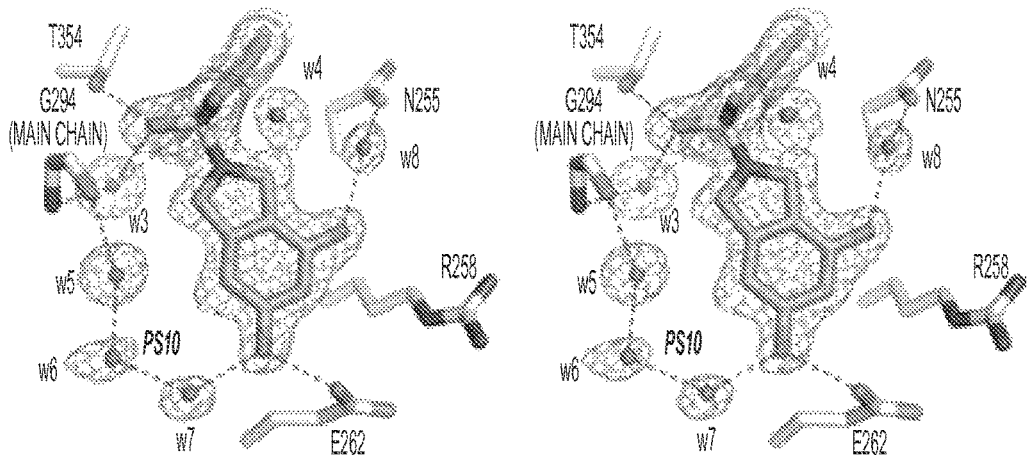

With the increased understanding that PDKs play a pivotal role in controlling glucose oxidation in disease states such as diabetes (Harris et al., 1997, Wu et al., 1999 and Rosa et al., 2003), cancer (Papandreou et al., 2006, Kim et al., 2006, Michelakis et al., 2010, Lu et al., 2008, Hitosugi et al., 2011 and Bonnet et al., 2007) and congestive heart failure, there is growing need for effective PDK inhibitors. The classic PDK inhibitor DCA binds to an enclosed allosteric site in the N-terminal domain, which is the binding site of PDC's substrate pyruvate for the physiological feedback inhibition (Kato et al., 2007 and Knoechel et al., 2006). However, this allosteric site is relatively small (volume=211 Å3), also buried and can only accommodate small ligands such as pyruvate and DCA (FIG. 7). The space limitation in the PDK allosteric site precludes the structure-based modification of DCA to improve its potency as a PDK inhibitor. The strategy of developing PDK inhibitors by targeting the lipoyl-binding pocket was unsuccessful in vivo (Mayers et al., 2003). PDK2 and PDK3 are anchored to lipoyl-bearing domains on the E2/E3BP core of PDC for optimal kinase activity (Kato et al., 2005 and Baker et al., 2000). Dihydrolipoamide mimetics attenuate PDK2 and PDK3 activities by impeding binding of these PDK isoforms to the inner lipoyl-bearing domain of the E3/E3BP core (Tuganova et al., 2007). However, PDK4, which is up-regulated in obesity and diabetes (Harris et al., 1997, Wu et al., 1999 and Rosa et al., 2003) shows robust kinase activity without binding to inner lipoyl-bearing domain of the E2E3BP core. The binding of the dihydrolipoamide mimetic AZD7545 to PDK4 stimulates rather than inhibits its kinase activity considerably (Kato et al., 2008).

In the present study, the inventors undertook a different approach to develop a new generation of PDK inhibitors that dock to the ATP-binding pocket (volume=865 Å3) of PDK2, which is open and four times larger than the allosteric DCA-binding pocket (FIG. 7). The conservation in the ATP-binding pocket between Hsp90 and PDK2, both belonging to the GHKL ATPase/kinase superfamily (Dutta and Inouye, 2000), makes it possible to utilize the chemical scaffold in Hsp90 inhibitors PA1 and PA7 as the starting point for designing the PDK-specific inhibitors. The distinct conformations of the bound PA7 between the Hsp90-PA7 and PDK2-PA7 structures (FIG. 2D) provided the first clue for utilizing structure-based design to develop PDK-specific inhibitors. It is remarkable that a single replacement of the carbonyl group in PA7 with a sulfonyl group in PS2 results in a drastic conversion of an Hsp90 inhibitor (PA7) to a PDK inhibitor (PS2). These results epitomize the feasibility of designing a highly selective kinase inhibitor by taking advantage of the unique structural features in the ATP-binding pocket.

To assess the efficacy of PDK inhibitor PS10 in vivo, DIO mice fed high-fat diet develop symptoms characteristic of the metabolic syndrome and if left on the diet long enough will eventually develop type 2 diabetes (Wang, 2012). PDC activity is low in heart and liver from DIO mice fed a high-fat diet for three weeks (FIGS. 5A and 5B). The effectiveness of PS10 as a PDK inhibitor in vivo is established by higher PDC activity in most tissues from PS10-treated over vehicle-treated DIO mice. The increased PDC flux in liver promotes glucose disposal, leading to improved glucose tolerance in PS10-treated DIO mice (FIG. 6A). The reduced plasma level of the gluconeogenic substrate lactate (FIG. 6D) explains in part the lower glucose concentrations in PS10-treated DIO mice (FIG. 6A). In the heart, a single dose of PS10 treatment results in drastic enhancement of PDC activity (FIG. 5A); however, the prolonged PS10 treatment causes a reduction in the fold increase of PDC activity (FIG. 5B). The results suggest a reset of the cardiac PDC flux during the long-term PS10 dosing. PDK4 expression is up-regulated in right ventricular hypertrophy causing an increase in glycolysis over glucose oxidation (Piao et al., 2013). The increased cardiac PDC flux by PS10 may offer an approach to mitigating impaired glucose oxidation in congenital heart failure.

The above increased glucose disposal through enhanced PDC flux is coupled with decreased lipogenesis in PS10-treated DIO mice, as demonstrated by the lessened hepatic steatosis, lower fat mass and attenuated plasma cholesterol as well as triglycerides levels (FIGS. 6D-H). The combination of reduced lipogenesis and increased glucose oxidation has been reported in acetyl-CoA carboxylase 2 (Choi et al., 2007) or PDK4 (Hwang et al., 2009) knockout mice on high-fat diets. In the liver of PDK4-deficient mice, the expression of both fatty acid synthase and acetyl-CoA carboxylase is reduced, which likely results in reduced lipogenesis with improved hepatic steatosis (Choi et al., 2007). Interestingly, the two transcription factors that promote fatty acid oxidation, i.e., PPARα and PGC-1α (Lin et al., 2005) in PDK4-deficient mice fed the high-fat diet are restored to the levels of the wild-type animals on chow diet (Hwang et al., 2009). The excess acetyl-CoA from both glucose and fatty acid oxidation is converted to ketone bodies, since plasma concentrations of both β-hydroxybutyrate and acetoacetate were considerably elevated in PDK2/PDK4 double knockout mice compared to the wild-type (Jeoung et al., 2012). Taken together, the present results illustrate the therapeutic potentials of PDK inhibitors in increasing hepatic glucose oxidation through PDC flux while suppressing lipogenesis in the liver of diet-induced obesity.

TABLE 1

IC$_{50}$ and dissociation constants of known and novel PDK inhibitors

| Compound | IC$_{50}$, µM for PDK2 | IC$_{50}$, µM for PDK4 | K$_d$, nM for PDK2 | K$_d$, nM for Hsp 90 |
|---|---|---|---|---|
| DCA* | 183 | 80.0 | — | — |
| Radicicol* | 77.8 | — | 18,600 ± 3,200 | 46.3 ± 7.2 |
| DC23 | 3.82 | 0.28 | 6,760 ± 2,040 | 25.0 ± 10.1 |
| PA1 | 6.78 | 1.86 | 3,570 ± 560 | 6.0 ± 2.6 |
| PA7 | 5.68 | 1.05 | 1,827 ± 179 | 27.3 ± 2.5 |
| PS2 | 2.11 | 2.20 | 711 ± 33 | 50,900 ± 9,200 |
| PS8 | 1.07 | 1.10 | 426 ± 32 | 60,100 ± 1,300 |
| PS10 | 0.80 | 0.76 | 239 ± 16 | 47,000 ± 5,200 |

PDK activity was assayed with increasing concentrations (31.6 nM to 1 mM) of the inhibitor as described in Experimental procedures. IC$_{50}$ values were obtained by the curve fitting of inhibition isotherms using program Prism 6 (GraphPad software, Inc.). Dissociation constants (K$_d$) were determined by ITC as also described in Experimental procedures.
*Known PDK inhibitor.

TABLE 3

IC$_{50}$ value for the inhibition of the four PDK isoforms by PS8 and PS10

|  | IC$_{50}$ of PS8, µM |  | IC$_{50}$ of PS10, µM |
|---|---|---|---|
| E2/E3BP | − | + | − |
| PDK1 | 2.50 ± 0.14 | 2.14 ± 0.33 | 2.07 |
| PDK2 | 1.07 ± 0.14 | 0.71 ± 0.14 | 0.80 |
| PDK3 | 13.72 ± 2.08 | 2.55 ± 0.38 | 21.30 |
| PDK4 | 1.10 ± 0.21 | 0.84 ± 0.08 | 0.77 |

PDK activity was assayed with increasing concentrations (31.6 nM to 1 mM) of the inhibitor in the presence or absence of the E2/E3BP core of PDC as described in Experimental procedures. IC$_{50}$ values were obtained by the curve fitting of inhibition isotherms using program Prism 6 (GraphPad Software, Inc.).

TABLE 2

Crystallographic data collection and refinement statistics (molecular replacement)

|  | PDK2 + PA1 | PDK2 + PA7 | PDK2 + PS2 | PDK2 + PS8 | PDK2 + PS10 |
|---|---|---|---|---|---|
| PDB ID | 4MP2 | 4MP7 | 4MPC | 4MPE | 4MPN |
| Data collection | | | | | |
| Space group | I4$_1$22, 1 molecular per asymmetric unit, ~70% solvent content | | | | |
| Cell dimensions | | | | | |
| a, b (Å) | 110.32 | 110.01 | 110.63 | 110.42 | 110.62 |
| c (Å) | 229.52 | 227.74 | 228.57 | 228.62 | 228.74 |
| α, β, γ (°) | α = β = γ = 90 | α = β = γ = 90 | α = β = γ = 90 | α = β = γ = 90 | α = β = γ = 90 |
| Resolution (Å) | 50-1.75 (1.78-1.75)* | 50-1.80 (1.83-1.80) | 50-1.70 (1.73-1.70) | 50-1.95 (1.98-1.95) | 50-1.75 (1.78-1.75) |
| R$_{merge}$ | 4.6 (71.7) | 6.7 (91.1) | 4.9 (84.5) | 6.9 (82.7) | 5.0 (75.6) |
| I/σI | 40.3 (3.1) | 30.9 (2.6) | 42.1 (2.1) | 29.8 (2.4) | 53.3 (3.5) |
| Completeness (%) | 99.1 (100.0) | 99.9 (100.0) | 99.5 (100.0) | 99.9 (100.0) | 99.9 (100.0) |
| Redundancy | 7.9 (8.0) | 10.3 (10.3) | 7.8 (7.1) | 9.3 (9.4) | 14.1 (14.2) |
| Refinement | | | | | |
| Resolution (Å) | 1.75 | 1.80 | 1.70 | 1.95 | 1.75 |
| No. reflections | 70461 | 64713 | 77555 | 51386 | 118280 |
| R$_{work}$/R$_{free}$ (%) | 20.4/21.9 | 19.1/20.5 | 19.9/21.8 | 19.2/20.4 | 18.7/20.2 |
| No. atoms | | | | | |
| Protein | 3000 | 2965 | 3040 | 2958 | 3011 |
| Inhibitor | 20 | 19 | 20 | 21 | 22 |
| Tratrate | 10 | 10 | 10 | 10 | 10 |
| Water | 212 | 213 | 197 | 184 | 179 |
| B-factors | | | | | |
| Protein | 36.4 | 35.3 | 36.4 | 41.2 | 27.0 |
| Inhibitor | 47.7 | 22.8 | 24.4 | 29.7 | 14.7 |
| Tartrate | 55.5 | 53.6 | 52.9 | 62.0 | 48.8 |
| Water | 44.0 | 41.9 | 41.5 | 44.3 | 29.2 |
| R.m.s. deviations | | | | | |
| Bond lengths (Å) | 0.006 | 0.006 | 0.006 | 0.007 | 0.007 |
| Bond angles (°) | 1.093 | 1.018 | 1.099 | 1.037 | 1.043 |

*Values in parentheses are for highest-resolution shell.

TABLE 4

Pharmacokinetic parameters for PS8 and PS10.

| | PS8 | PS10 |
|---|---|---|
| Dose | 20 mg/kg IP | 70 mg/kg IP |
| Terminal $T_{1/2}$ | 93.3 min | 161 min |
| $C_{max}$ | 7,600 ng/ml | 32,400 ng/ml |
| $T_{max}$ | 10 min | 10 min |
| $AUC_{last}$ | 310,035 min · ng/ml | 1,905,136 min · ng/ml |
| $V_z/F$ | 209 ml | 172 ml |
| CL/F | 1.55 ml/min | 0.741 ml/min |

Terminal $T_{1/2}$, half-life of the terminal phase;
$C_{max}$, observed maximum plasma concentration;
$T_{max}$, time to reach $C_{max}$;
$AUC_{last}$, area under the concentration-time curve from 0 to the last measured point;
$V_z/F$, apparent volume of distribution during terminal phase; and
CL/F, volume of plasma cleared of the drug per unit time, where F is the fraction bioavailable as compared to an IV dose, which is not known.

TABLE 5

SAR of PS35 derivatives on affinity to PDK2

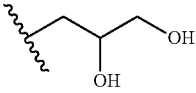 [SMILES: *CC(O)CO]

| cpds | R | PDK2 $K_d$ (nM) |
|---|---|---|
| PS35 | H | 143 |
| PS37 | ` | 445 |
| PS38 | 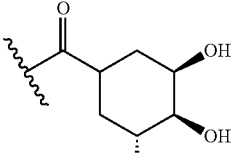 | 188 |
| PS39 | 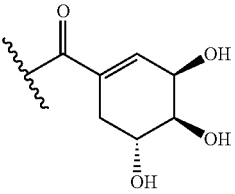 [SMILES: *C(=O)C1=C[C@@H](O)[C@@H](O)[C@H](O)C1] | 338 |
| PS40 | 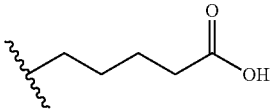 [SMILES: *CCCCC(=O)O] | 403 |
| PS41 | 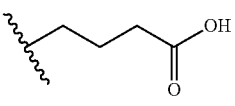 [SMILES: *CCCC(=O)O] | 1397 |
| PS42 | | 917 |

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

Aicher et al., *J Medicinal Chemistry* 43, 236-249, 2000.
Baker et al., *J Biological Chemistry* 275, 15773-15781, 2000.
Bonnet et al., *Cancer Cell* 11, 37-51, 2007.
Bundgaard, *Drugs of the Future*, 16:443-458, 1991.
Bundgaard, In: Design of Prodrugs, 7-9; 21-24, Elsevier, Amsterdam, 1985.
Burgess et al., *The Journal of biological chemistry* 283, 1670-1678, 2008.
Cha-Molstad et al., *The Journal of biological chemistry* 284, 16898-16905, 2009.
Choi et al., *Proceedings National Academy Sciences USA* 104, 16480-16485, 2007.
Crewe et al., *PLoS One* 8, e77280, 2013.
Denechaud et al., *FEBS letters* 582, 68-73, 2008.
Dutta and Inouye, *Trends Biochemical Sciences* 25, 24-28, 2000.
Dymock et al., *J Medicinal Chemistry* 48, 4212-4215, 2005.
Ferriero et al., *Science Translational Medicine* 5, 175ra131, 2013.
Filhoulaud et al., *Trends in endocrinology and metabolism: TEM* 24, 257-268, 2013.
Freire et al., *Drug Discovery Today* 13, 869-874, 2008.
Greene and Wuts, In: Protecting Groups in Organic Synthesis, 3rd ed., John Wiley & Sons, Inc., 1999.
Handbook of Pharmaceutical Salts: Properties, Selection and Use, Stahl and Wermuth (Eds.), Verlag Helvetica Chimica Acta, 2002.
Harris et al., *Adv Enzyme Regul* 37, 271-293, 1997.
Hitosugi et al., *Molecular Cell* 44, 864-877, 2011.
Hwang et al., *Biochem J* 423, 243-252, 2009.
Iannitti et al., *Drugs in R&D* 11, 227-249, 2011.
Iizuka et al., *American journal of physiology. Endocrinology and metabolism* 291, E358-364, 2006.
Jeoung et al., *Biochem J* 443, 829-839, 2012.
Jiang et al., *Nature Genetics* 45, 72-75, 2013.
Kaplon et al., *Nature* 498, 109-112, 2013.
Kato et al., *Structure* 15, 992-1004, 2007.
Kato et al., *Structure* 16, 1849-1859, 2008.
Kato et al., *EMBO J* 24, 1763-1774, 2005.
Kibbe et al., *The Journal of biological chemistry* 288, 23194-23202, 2013.
Kim et al., *Cell Metabolism* 3, 177-185, 2006.
Knoechel et al., *Biochemistry* 45, 402-415, 2006.
Korotchkina et al., *Free Radical Res* 38, 1083-1092, 2004.

Kukimoto-Niino et al., Section D, *Biological Crystallography* 67, 763-773, 2011.
Kung et al., *J Medicinal Chemistry* 53, 499-503, 2010.
Kuzuya et al., *Biochemical Biophysical Research Comm* 373, 94-98, 2008.
Lin et al., *Cell Metabolism* 1, 361-370, 2005.
Lu et al., *J Biological Chemistry* 283, 28106-28114, 2008.
Mayers et al., *Biochemical Society Transactions* 31, 1165-1167, 2003.
Meng et al., *Journal of medicinal chemistry*, doi:10.1021/jm5010144 (2014).
Merritt et al., *Proceedings of the National Academy of Sciences of the United States of America* 108, 19084-19089, 2011.
Merritt et al., *Proceedings of the National Academy of Sciences of the United States of America* 104, 19773-19777, 2007.
Michelakis et al., *Science Translational Medicine* 2, 31ra34, 2010.
Moore et al., *Oncotarget*, (2014).
Murray et al., *J Medicinal Chemistry* 53, 5942-5955, 2010.
Papandreou et al., *Cell Metabolism* 3, 187-197, 2006.
Piao et al., *J Mol Med (Berl)* 91, 333-346, 2013.
Randle, *Proceedings Nutrition Society* 54, 317-327, 1995.
Reed, *J Bological Chemistry* 276, 38329-38336, 2001.
Rosa et al., *Obesity Research* 11, 176-182, 2003.
Scott et al., *Biochemistry* 51, 4990-5003, 2012.
Steussy et al., *J Biological Chemistry* 276, 37443-37450, 2001.
Tso et al., *The Journal of biological chemistry* 289, 4432-4443, 2014.
Tuganova et al., *Biochemistry* 46, 8592-8602, 2007.
Uyeda, K. & Repa, J. J., *Cell metabolism* 4, 107-110, 2006.
Vaxillaire and Froguel, *Endocr Rev,* 29:254-264, 2008.
Wang et al., *Diabetologia,* 50:348-358, 2007.
Wang et al., *J Biol Chem,* 277:17564-17570, 2002.
Wang et al., *Proceedings National Academy Sciences USA,* 106:1427-1432, 2009.
Wang, *Methods Mol Biol* 821, 421-433, 2012.
White et al., *Diabetes,* 57:654-668, 2008.
Whitehouse and Randle, *Biochem J* 134, 651-653, 1973.
Wicksteed et al., *Cell Metab,* 5:221-227, 2007.
Wilson et al., *Mech Dev,* 120:65-80, 2003.
Wu et al., *Diabetes* 48, 1593-1599, 1999.
Wynn et al., *J Biol Chem.* 283(37):25305-15, 2008.
Yamashita et al., *Proceedings of the National Academy of Sciences of the United States of America* 98, 9116-9121, 2001.

What is claimed is:
1. A compound of the formula:

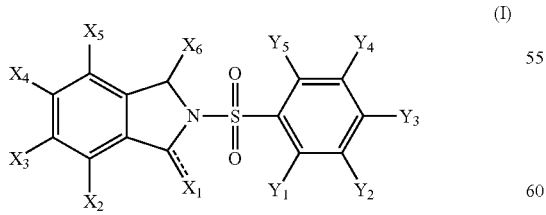

(I)

wherein:
$X_1$ is hydrogen, halogen, hydroxy, amino, cyano, nitro, or oxo, or $alkyl_{(C\leq12)}$, $alkenyl_{(C\leq12)}$, $alkynyl_{(C\leq12)}$, $aryl_{(C\leq18)}$, $aralkyl_{(C\leq18)}$, $heterocycloalkyl_{(C\leq12)}$, $heteroaryl_{(C\leq12)}$, $acyl_{(C\leq12)}$, —C(O)-$alkoxy_{(C\leq12)}$, $alkoxy_{(C\leq12)}$, $alkenyloxy_{(C\leq12)}$, $alkynyloxy_{(C\leq12)}$, $aryloxy_{(C\leq18)}$, $aralkyloxy_{(C\leq18)}$, $heterocycloalkyloxy_{(C\leq12)}$, $heteroaryloxy_{(C\leq12)}$, $acyloxy_{(C\leq12)}$, $alkylamino_{(C\leq12)}$, $dialkylamino_{(C\leq12)}$, $alkenylamino_{(C\leq12)}$, $alkynylamino_{(C\leq12)}$, $arylamino_{(C\leq18)}$, $aralkylamino_{(C\leq18)}$, $heterocycloalkylamino_{(C\leq12)}$, $heteroarylamino_{(C\leq12)}$, $amido_{(C\leq12)}$, -$arenediyl_{(C\leq6)}$-$heteroaryl_{(C\leq12)}$, or a substituted version of any of these groups, or is taken together with $X_6$ as defined below;

$X_2$ and $X_5$ are each independently hydrogen, hydroxy, nitro, cyano, or amino, or $alkyl_{(C\leq12)}$, $alkenyl_{(C\leq12)}$, $alkynyl_{(C\leq12)}$, $aryl_{(C\leq18)}$, $aralkyl_{(C\leq18)}$, $heterocycloalkyl_{(C\leq12)}$, $heteroaryl_{(C\leq12)}$, $acyl_{(C\leq12)}$, $alkoxy_{(C\leq12)}$, $alkenyloxy_{(C\leq12)}$, $alkynyloxy_{(C\leq12)}$, $aryloxy_{(C\leq18)}$, $aralkyloxy_{(C\leq18)}$, $heterocycloalkyloxy_{(C\leq12)}$, $heteroaryloxy_{(C\leq12)}$, $acyloxy_{(C\leq12)}$, $alkylthio_{(C\leq12)}$, $alkenylthio_{(C\leq12)}$, $alkynylthio_{(C\leq12)}$, $arylthio_{(C\leq18)}$, $aralkylthio_{(C\leq18)}$, $heterocycloalkylthio_{(C\leq12)}$, $heteroarylthio_{(C\leq12)}$, $acylthio_{(C\leq12)}$, $alkylamino_{(C\leq12)}$, $dialkylamino_{(C\leq12)}$, $alkenylamino_{(C\leq12)}$, $alkynylamino_{(C\leq12)}$, $arylamino_{(C\leq18)}$, $aralkylamino_{(C\leq18)}$, $heterocycloalkylamino_{(C\leq12)}$, $heteroarylamino_{(C\leq12)}$, $amido_{(C\leq12)}$, -$alkanediyl_{(C\leq6)}$-$heterocycloalkyl_{(C\leq12)}$, or a substituted version of any of these groups; or

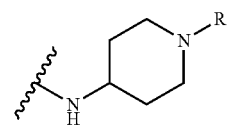

wherein:
R is hydrogen; or
$alkyl_{(C\leq12)}$, $alkenyl_{(C\leq12)}$, $acyl_{(C\leq12)}$, $aryl_{(C\leq12)}$, $aralkyl_{(C\leq12)}$, or a substituted version of any of these groups;

$X_3$ and $X_4$ are each independently hydrogen, hydroxy, or amino, or $alkoxy_{(C\leq12)}$, $alkenyloxy_{(C\leq12)}$, $alkynyloxy_{(C\leq12)}$, $aryloxy_{(C\leq18)}$, $aralkyloxy_{(C\leq18)}$, $heterocycloalkyloxy_{(C\leq12)}$, $heteroaryloxy_{(C\leq12)}$, $acyloxy_{(C\leq12)}$, $alkylamino_{(C\leq12)}$, $dialkylamino_{(C\leq12)}$, $alkenylamino_{(C\leq12)}$, $alkynylamino_{(C\leq12)}$, $arylamino_{(C\leq18)}$, $aralkylamino_{(C\leq18)}$, $heterocycloalkylamino_{(C\leq12)}$, $heteroarylamino_{(C\leq12)}$, $amido_{(C\leq12)}$, -$alkanediyl_{(C\leq6)}$-$heterocycloalkyl_{(C\leq12)}$, or a substituted version of any of these groups; or

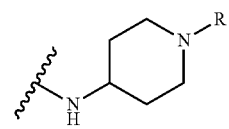

wherein:
R is hydrogen; or
$alkyl_{(C\leq12)}$, $alkenyl_{(C\leq12)}$, $acyl_{(C\leq12)}$, $aryl_{(C\leq12)}$, $aralkyl_{(C\leq12)}$, or a substituted version of any of these groups;

$X_6$ is hydrogen, halogen, hydroxy, amino, nitro, or cyano, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, alkenylamino$_{(C\leq12)}$, alkynylamino$_{(C\leq12)}$, arylamino$_{(C\leq18)}$, aralkylamino$_{(C\leq18)}$, heterocycloalkylamino$_{(C\leq12)}$, heteroarylamino$_{(C\leq12)}$, or amido$_{(C\leq12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, or a substituted version of any of these groups;

$X_1$ and $X_6$ when taken together have the formula:

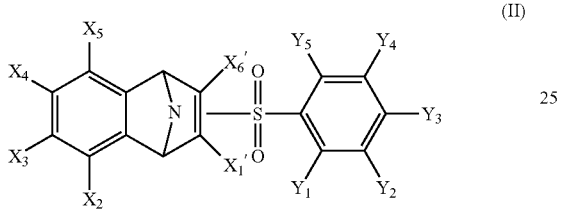

(II)

wherein:

$X_1'$ and $X_6'$ are each independently hydrogen, hydroxy, halo, or amino;

alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, acyl$_{(C\leq12)}$, or a substituted version of any of these groups;

provided that at least one of $Y_1$, $Y_2$, $Y_3$, $Y_4$, or $Y_5$ are hydroxy or alkoxy$_{(C\leq12)}$ and that $X_2$, $X_3$, $X_4$, and $X_5$ are not all hydrogen, or that when $X_1$ is oxo then $X_6$ is not aryl$_{(C\leq8)}$;

or a pharmaceutically acceptable salt thereof.

2. A compound of claim 1, wherein the compound is further defined by the formula:

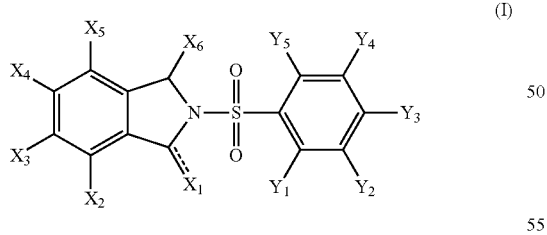

(I)

wherein:

$X_1$ is hydrogen, hydroxy, amino, or oxo, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, —C(O)-alkoxy$_{(C\leq12)}$, alkylamino$_{(C\leq12)}$, dialkylamino$_{(C\leq12)}$, -arenediyl$_{(C\leq6)}$-heteroaryl$_{(C\leq12)}$, or a substituted version of any of these groups, or is taken together with $X_6$ as defined below;

$X_2$ and $X_5$ are each independently hydrogen, hydroxy, or amino, or alkyl$_{(C\leq12)}$, alkoxy$_{(C\leq12)}$, heterocycloalkoxy$_{(C\leq12)}$, alkylthio$_{(C\leq12)}$, heterocycloalkylthio$_{(C\leq12)}$, alkylamino$_{(C\leq12)}$, dialkylamino$_{(C\leq12)}$, heterocycloalkylamino$_{(C\leq12)}$, -alkanediyl$_{(C\leq6)}$-heterocycloalkyl$_{(C\leq12)}$, or a substituted version of any of these groups; or

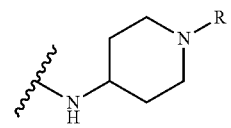

wherein:

R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups;

$X_3$ and $X_4$ are each independently hydrogen, hydroxy, or amino, or alkoxy$_{(C\leq12)}$, alkylamino$_{(C\leq12)}$, heterocycloalkylamino$_{(C\leq12)}$, or a substituted version of any of these groups; or

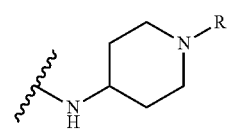

wherein:

R is hydrogen; or alkyl$_{(C\leq12)}$, alkenyl$_{(C\leq12)}$, acyl$_{(C\leq12)}$, aryl$_{(C\leq12)}$, aralkyl$_{(C\leq12)}$, or a substituted version of any of these groups;

$X_6$ is hydrogen, hydroxy, amino, or alkyl$_{(C\leq12)}$, alkenyl$_{(C\leq12)}$, alkynyl$_{(C\leq12)}$, aryl$_{(C\leq18)}$, aralkyl$_{(C\leq18)}$, heterocycloalkyl$_{(C\leq12)}$, heteroaryl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq18)}$, aralkyloxy$_{(C\leq18)}$, heterocycloalkyloxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, alkenylamino$_{(C\leq12)}$, alkynylamino$_{(C\leq12)}$, arylamino$_{(C\leq18)}$, aralkylamino$_{(C\leq18)}$, heterocycloalkylamino$_{(C\leq12)}$, heteroarylamino$_{(C\leq12)}$, or amido$_{(C\leq12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, or a substituted version of any of these groups;

$X_1$ and $X_6$ when taken together have the formula:

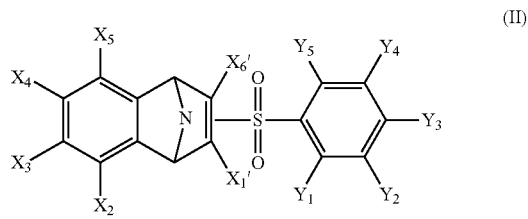

(II)

wherein:

X₁' and X₆' are each independently hydrogen, hydroxy, halo, or amino;

alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, acyl$_{(C≤12)}$, or a substituted version of any of these groups;

provided that at least one of Y₁, Y₂, Y₃, Y₄, or Y₅ are hydroxy or alkoxy$_{(C≤12)}$ and that X₂, X₃, X₄, and X₅ are not all hydrogen, or that when X₁ is oxo then X₆ is not aryl$_{(C≤8)}$;

or a pharmaceutically acceptable salt thereof.

3. The compound of claim 1, wherein X₁ is hydrogen.

4. The compound of claim 1, wherein X₁ is oxo.

5. The compound according to claim 1, wherein X₂ and X₅ are each independently hydrogen.

6. The compound according to claim 1, wherein X₂ and X₅ are each independently hydroxy or alkoxy$_{(C≤12)}$.

7. The compound according to claim 1, wherein X₂ and X₅ are each independently methoxy.

8. The compound according to claim 1, wherein X₃ and X₄ are each independently hydrogen.

9. The compound according to claim 1, wherein X₃ and X₄ are each independently hydroxy or alkoxy$_{(C≤12)}$.

10. The compound according to claim 1, wherein X₃ and X₄ are each independently methoxy.

11. The compound according to claim 1, wherein X₃ and X₄ are each independently amino, alkylamino$_{(C≤12)}$, heterocycloalkylamino$_{(C≤12)}$, substituted alkylamino$_{(C≤12)}$, or substituted heterocycloalkylamino$_{(C≤12)}$.

12. The compound of claim 11, wherein X₃ and X₄ are each independently amino, cyclohexylamine, or

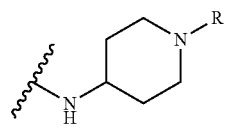

wherein: R is hydrogen; or alkyl$_{(C≤12)}$, alkenyl$_{(C≤12)}$, acyl$_{(C≤12)}$, aryl$_{(C≤12)}$, aralkyl$_{(C≤12)}$, or a substituted version of any of these groups.

13. The compound according to claim 1, wherein X₆ is hydrogen.

14. The compound according to claim 1, wherein X₆ is alkyl$_{(C≤12)}$, alkenyl$_{(C≤12)}$, aryl$_{(C≤12)}$, or a substituted version of any of these groups.

15. The compound according to claim 1, wherein Y₁, Y₂, Y₃, Y₄, and Y₅ are each independently hydrogen.

16. The compound according to claim 1, wherein Y₁, Y₂, Y₃, Y₄, and Y₅ are each independently halo, hydroxy, or alkoxy$_{(C≤12)}$.

17. The compound of claim 16, wherein Y₁, Y₂, Y₃, Y₄, and Y₅ are each independently hydroxy.

18. The compound of claim 16, wherein Y₁, Y₂, Y₃, Y₄, and Y₅ are each independently methoxy.

19. The compound of claim 16, wherein Y₁ and Y₃ are both hydroxy or methoxy.

20. The compound of claim 1, wherein the compound is further defined as:

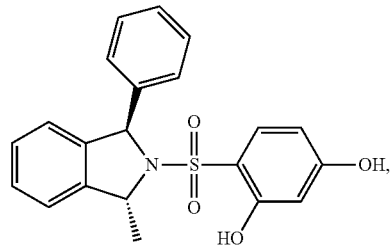

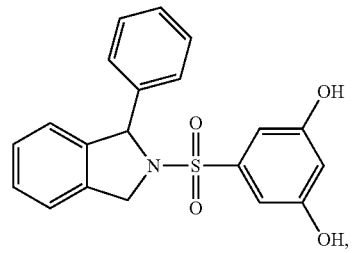

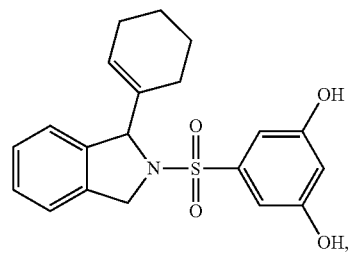

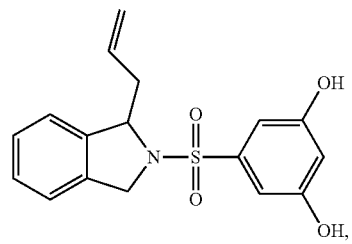

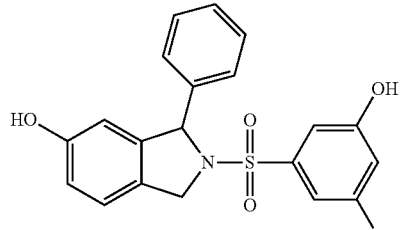

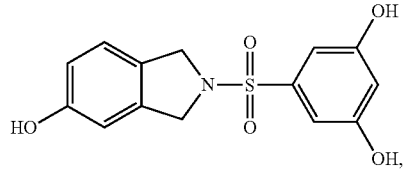

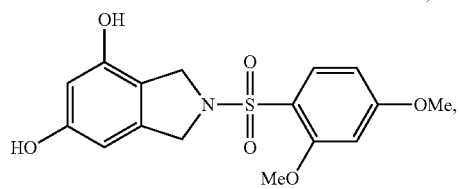

-continued
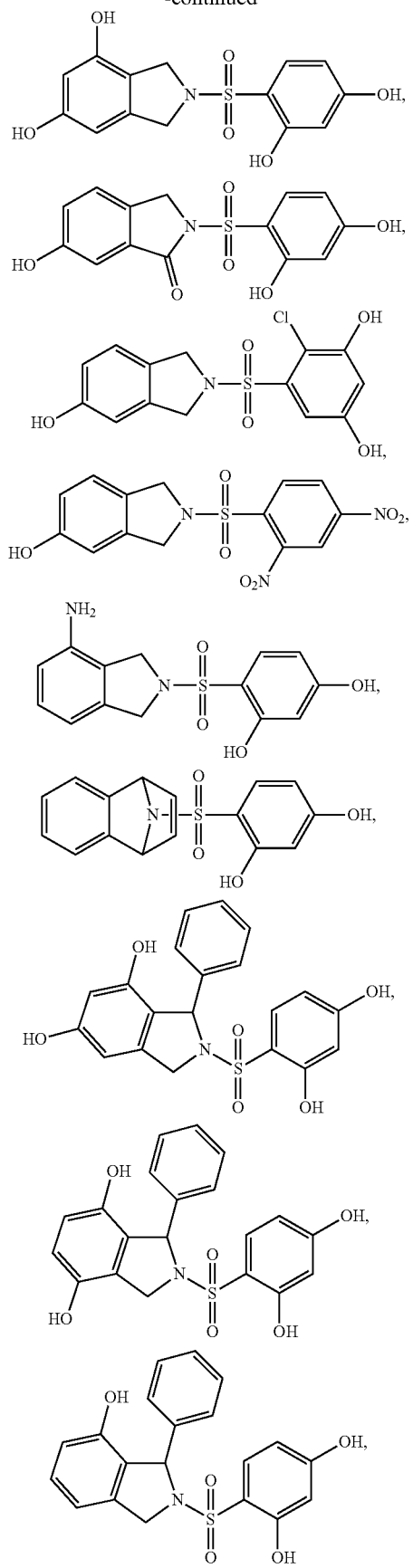
-continued
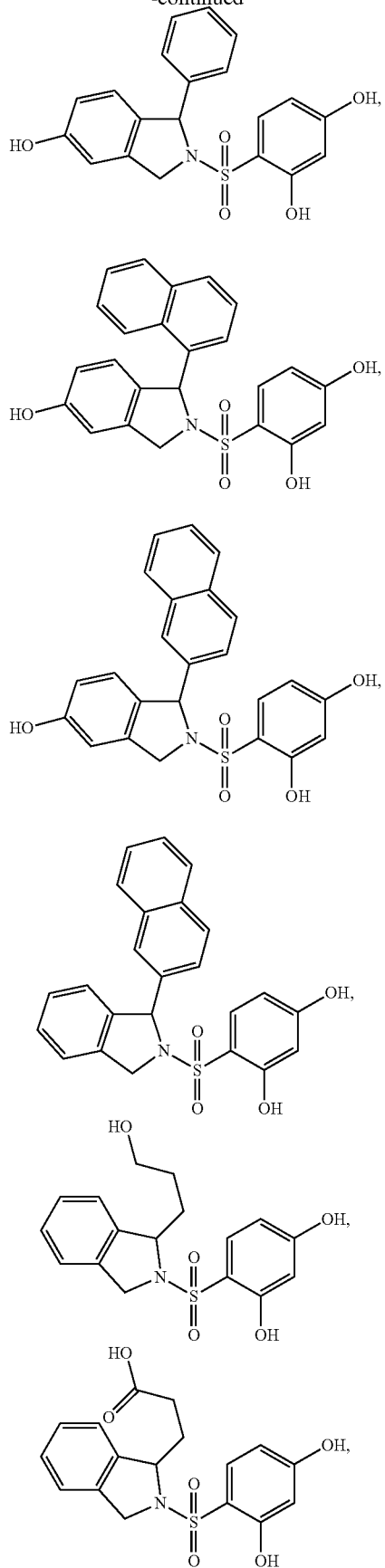

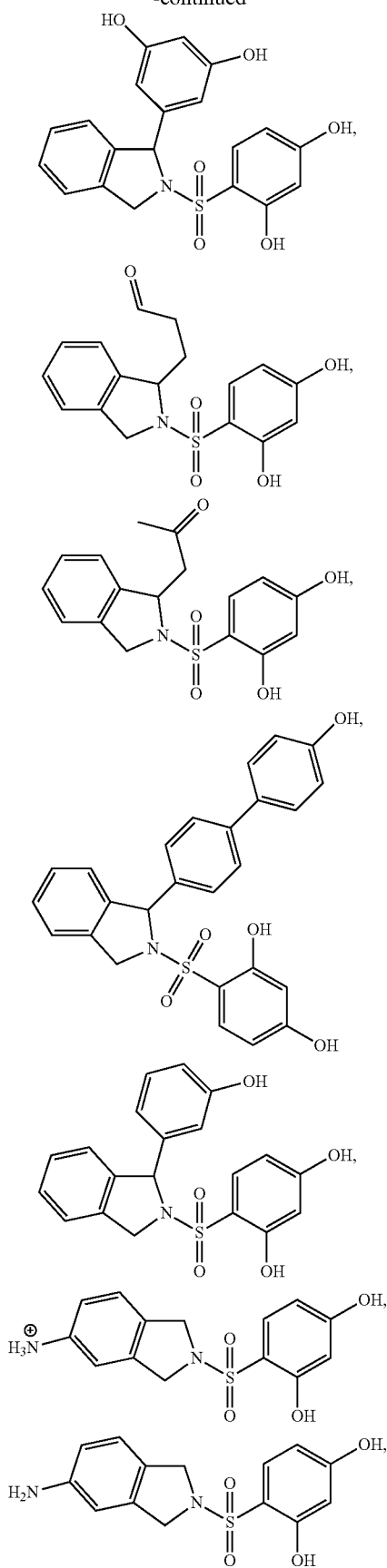
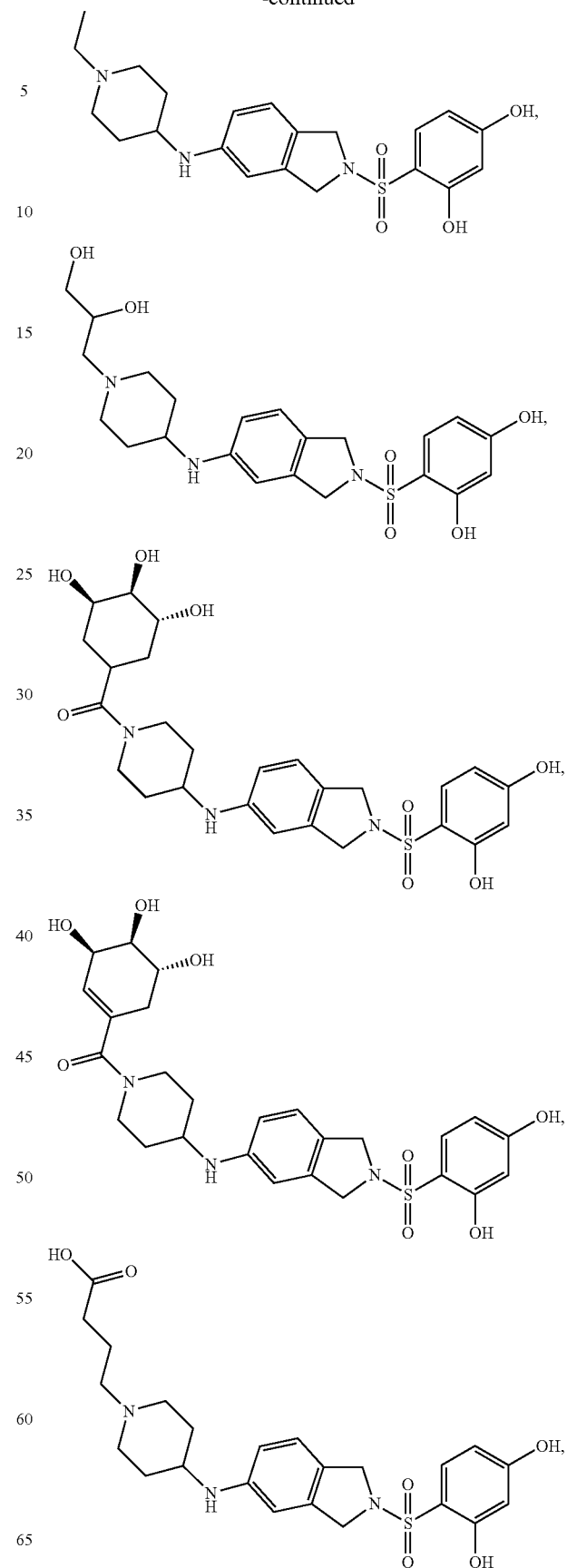

139

-continued

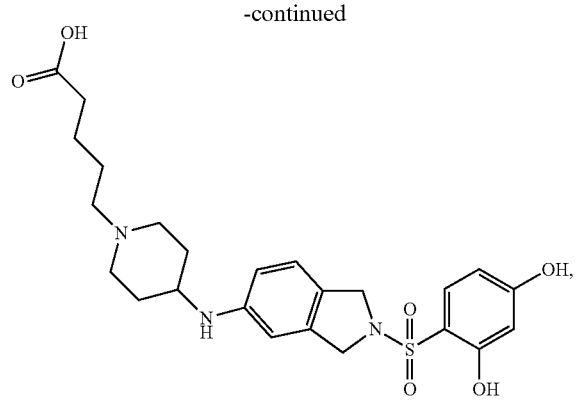

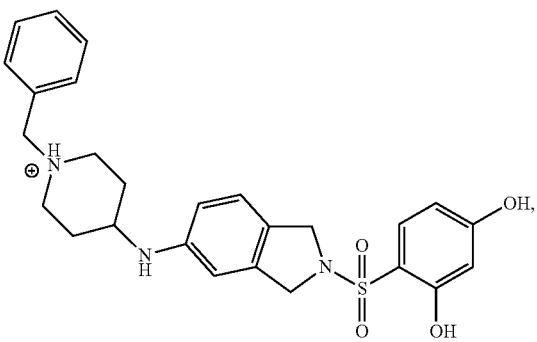

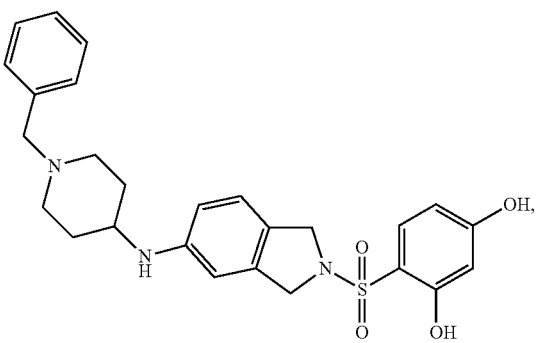

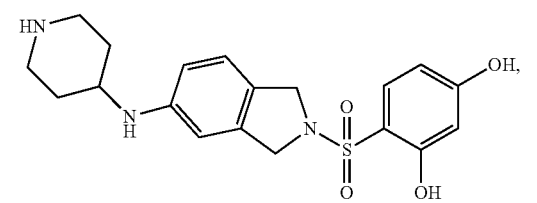

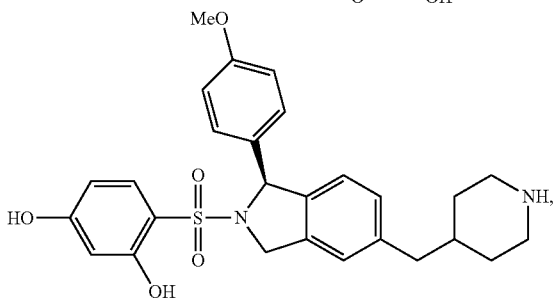

140

-continued

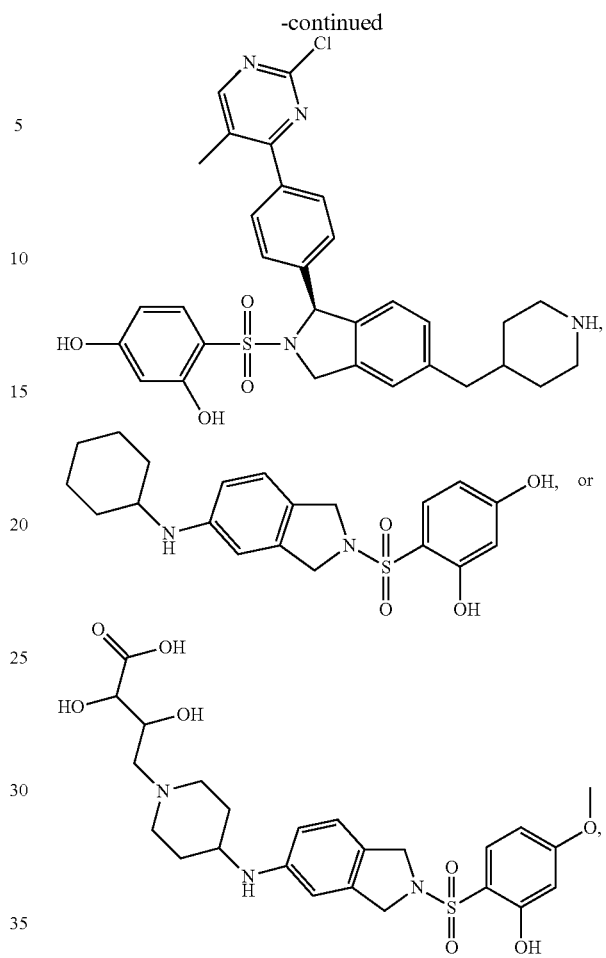

or a pharmaceutically acceptable salt, thereof.

21. A method for inhibiting the activity of a pyruvate dehydrogenase kinase comprising administering a compound of the formula:

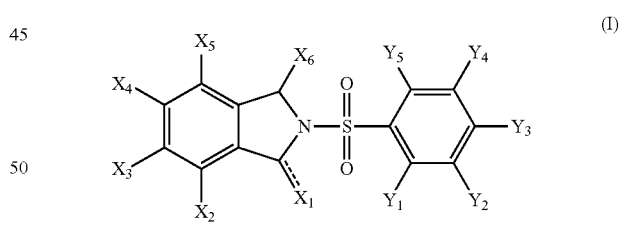

(I)

wherein:

$X_1$ is hydrogen, halogen, hydroxy, amino, cyano, nitro, or oxo, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, —C(O)-alkoxy$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylamino$_{(C≤12)}$, dialkylamino$_{(C≤12)}$, alkenylamino$_{(C≤12)}$, alkynylamino$_{(C≤12)}$, arylamino$_{(C≤18)}$, aralkylamino$_{(C≤18)}$, heterocycloalkylamino$_{(C≤12)}$, heteroarylamino$_{(C≤12)}$, amido$_{(C≤12)}$, -arenediyl$_{(C≤6)}$- heteroaryl$_{(C≤12)}$, or a substituted version of any of these groups, or is taken together with $X_6$ as defined below;

$X_2$, $X_3$, $X_4$, $X_5$ are each independently hydrogen, halogen, hydroxy, nitro, cyano, or amino, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylthio$_{(C≤12)}$, alkenylthio$_{(C≤12)}$, alkynylthio$_{(C≤12)}$, arylthio$_{(C≤18)}$, aralkylthio$_{(C≤18)}$, heterocycloalkylthio$_{(C≤12)}$, heteroarylthio$_{(C≤12)}$, acylthio$_{(C≤12)}$, alkylamino$_{(C≤12)}$, dialkylamino$_{(C≤12)}$, alkenylamino$_{(C≤12)}$, alkynylamino$_{(C≤12)}$, arylamino$_{(C≤18)}$, aralkylamino$_{(C≤18)}$, heterocycloalkylamino$_{(C≤12)}$, heteroarylamino$_{(C≤12)}$, amido$_{(C≤12)}$, or a substituted version of any of these groups; or

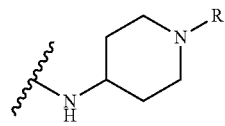

wherein:
R is hydrogen; or
alkyl$_{(C≤12)}$, alkenyl$_{(C≤12)}$, acyl$_{(C≤12)}$, aryl$_{(C≤12)}$, aralkyl$_{(C≤12)}$, or a substituted version of any of these groups;

$X_6$ is hydrogen, halogen, hydroxy, amino, nitro, or cyano, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylamino$_{(C≤12)}$, dialkylamino$_{(C≤12)}$, alkenylamino$_{(C≤12)}$, alkynylamino$_{(C≤12)}$, arylamino$_{(C≤18)}$, aralkylamino$_{(C≤18)}$, heterocycloalkylamino$_{(C≤12)}$, heteroarylamino$_{(C≤12)}$, or amido$_{(C≤12)}$, or a substituted version of any of these groups, or is taken together with $X_1$ as defined below;

$Y_1$, $Y_2$, $Y_3$, $Y_4$, and $Y_5$ are each independently hydrogen, amino, cyano, halo, hydroxy, or nitro, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, or a substituted version of any of these groups;

$X_1$ and $X_6$ when taken together have the formula:

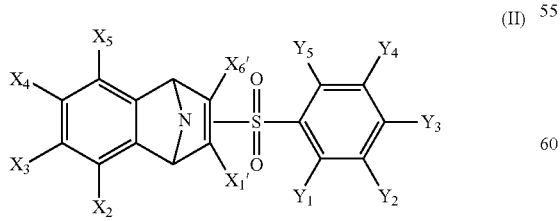

(II)

wherein:
$X_1'$ and $X_6'$ are each independently hydrogen, hydroxy, halo, or amino;

alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, acyl$_{(C≤12)}$, or a substituted version of any of these groups;
or a pharmaceutically acceptable salt thereof.

22. A method for treating diabetes in a subject comprising administering to the subject a therapeutically effective amount of a compound of the formula:

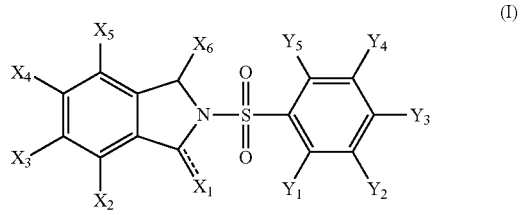

(I)

wherein:
$X_1$ is hydrogen, halogen, hydroxy, amino, cyano, nitro, or oxo, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, —C(O)-alkoxy$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylamino$_{(C≤12)}$, dialkylamino$_{(C≤12)}$, alkenylamino$_{(C≤12)}$, alkynylamino$_{(C≤12)}$, arylamino$_{(C≤18)}$, aralkylamino$_{(C≤18)}$, heterocycloalkylamino$_{(C≤12)}$, heteroarylamino$_{(C≤12)}$, amido$_{(C≤12)}$, -arenediyl$_{(C≤6)}$-heteroaryl$_{(C≤12)}$, or a substituted version of any of these groups, or is taken together with $X_6$ as defined below;

$X_2$, $X_3$, $X_4$, $X_5$ are each independently hydrogen, hydroxy, nitro, cyano, or amino, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylthio$_{(C≤12)}$, alkenylthio$_{(C≤12)}$, alkynylthio$_{(C≤12)}$, arylthio$_{(C≤18)}$, aralkylthio$_{(C≤18)}$, heterocycloalkylthio$_{(C≤12)}$, heteroarylthio$_{(C≤12)}$, acylthio$_{(C≤12)}$, alkylamino$_{(C≤12)}$, dialkylamino$_{(C≤12)}$, alkenylamino$_{(C≤12)}$, alkynylamino$_{(C≤12)}$, arylamino$_{(C≤18)}$, aralkylamino$_{(C≤18)}$, heterocycloalkylamino$_{(C≤12)}$, heteroarylamino$_{(C≤12)}$, amido$_{(C≤12)}$, -alkanediyl$_{(C≤6)}$-heterocycloalkyl$_{(C≤12)}$, or a substituted version of any of these groups; or

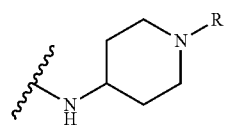

wherein:
R is hydrogen; or
alkyl$_{(C≤12)}$, alkenyl$_{(C≤12)}$, acyl$_{(C≤12)}$, aryl$_{(C≤12)}$, aralkyl$_{(C≤12)}$, or a substituted version of any of these groups;

$X_6$ is hydrogen, halogen, hydroxy, amino, nitro, or cyano, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylamino$_{(C≤12)}$, dialkylamino$_{(C≤12)}$, alkenylamino$_{(C≤12)}$, alkynylamino$_{(C≤12)}$, arylamino$_{(C≤18)}$, aralkylamino$_{(C≤18)}$, heterocycloalkylamino$_{(C≤12)}$, heteroarylamino$_{(C≤12)}$, or amido$_{(C≤12)}$, or a substituted version of any of these groups, or is taken together with $X_1$ as defined below;

$Y_2$, $Y_3$, $Y_4$, and $Y_5$ are each independently hydrogen, amino, cyano, halo, hydroxy, or nitro, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, or a substituted version of any of these groups;

$X_1$ and $X_6$ when taken together have the formula:

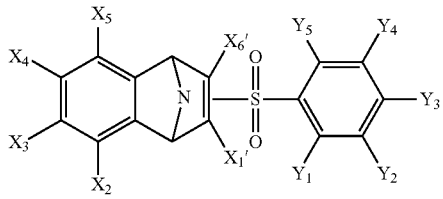

(II)

wherein:

$X_1'$ and $X_6'$ are each independently hydrogen, hydroxy, halo, or amino;

alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, acyl$_{(C≤12)}$, or a substituted version of any of these groups;

provided that when $X_1$ is oxo, then $X_6$ is not aryl$_{(C≤8)}$; or a pharmaceutically acceptable salt thereof.

23. A method for treating heart disease in a subject comprising administering to the subject a therapeutically effective amount of a compound of the formula:

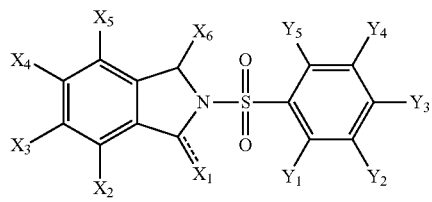

(I)

wherein:

$X_1$ is hydrogen, halogen, hydroxy, amino, cyano, nitro, or oxo, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, —C(O)-alkoxy$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylamino$_{(C≤12)}$, dialkylamino$_{(C≤12)}$, alkenylamino$_{(C≤12)}$, alkynylamino$_{(C≤12)}$, arylamino$_{(C≤18)}$, aralkylamino$_{(C≤18)}$, heterocycloalkylamino$_{(C≤12)}$, heteroarylamino$_{(C≤12)}$, amido$_{(C≤12)}$, -arenediyl$_{(C≤6)}$-heteroaryl$_{(C≤12)}$, or a substituted version of any of these groups, or is taken together with $X_6$ as defined below;

$X_2$, $X_3$, $X_4$, $X_5$ are each independently hydrogen, halogen, hydroxy, nitro, cyano, or amino, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylthio$_{(C≤12)}$, alkenylthio$_{(C≤12)}$, alkynylthio$_{(C≤12)}$, arylthio$_{(C≤18)}$, aralkylthio$_{(C≤18)}$, heterocycloalkylthio$_{(C≤12)}$, heteroarylthio$_{(C≤12)}$, acylthio$_{(C≤12)}$, alkylamino$_{(C≤12)}$, dialkylamino$_{(C≤12)}$, alkenylamino$_{(C≤12)}$, alkynylamino$_{(C≤12)}$, arylamino$_{(C≤18)}$, aralkylamino$_{(C≤18)}$, heterocycloalkylamino$_{(C≤12)}$, heteroarylamino$_{(C≤12)}$, amido$_{(C≤12)}$, -alkanediyl$_{(C≤6)}$-heterocycloalkyl$_{(C≤12)}$, or a substituted version of any of these groups; or

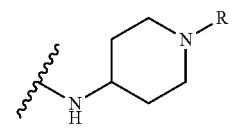

wherein:

R is hydrogen; or alkyl$_{(C≤12)}$, alkenyl$_{(C≤12)}$, acyl$_{(C≤12)}$, aryl$_{(C≤12)}$, aralkyl$_{(C≤12)}$, or a substituted version of any of these groups;

$X_6$ is hydrogen, halogen, hydroxy, amino, nitro, or cyano, or alkyl$_{(C≤12)}$, alkenyl$_{(C≤12)}$, alkynyl$_{(C≤12)}$, aryl$_{(C≤18)}$, aralkyl$_{(C≤18)}$, heterocycloalkyl$_{(C≤12)}$, heteroaryl$_{(C≤12)}$, acyl$_{(C≤12)}$, alkoxy$_{(C≤12)}$, alkenyloxy$_{(C≤12)}$, alkynyloxy$_{(C≤12)}$, aryloxy$_{(C≤18)}$, aralkyloxy$_{(C≤18)}$, heterocycloalkyloxy$_{(C≤12)}$, heteroaryloxy$_{(C≤12)}$, acyloxy$_{(C≤12)}$, alkylamino$_{(C≤12)}$, dialkylamino$_{(C≤12)}$, alkenylamino$_{(C≤12)}$, alkynylamino$_{(C≤12)}$, arylamino$_{(C≤18)}$, aralkylamino$_{(C≤18)}$, heterocycloalkylamino$_{(C≤12)}$, heteroarylamino$_{(C≤12)}$, or amido$_{(C≤12)}$, or a substituted version of any of these groups, or is taken together with $X_1$ as defined below;

$Y_2$, $Y_3$, $Y_4$, and Ys are each independently hydrogen, amino, cyano, halo, hydroxy, or nitro, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, or a substituted version of any of these groups;

$X_1$ and $X_6$ when taken together have the formula:

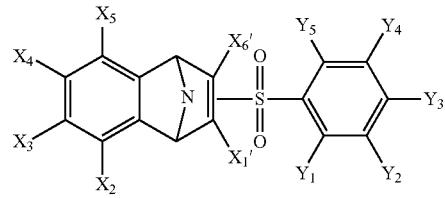

(II)

wherein:

$X_1'$ and $X_6'$ are each independently hydrogen, hydroxy, halo, or amino;

alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, acyl$_{(C\leq 12)}$, or a substituted version of any of these groups;
or a pharmaceutically acceptable salt thereof.

* * * * *

UNITED STATES PATENT AND TRADEMARK OFFICE
CERTIFICATE OF CORRECTION

PATENT NO. : 10,167,258 B2  
APPLICATION NO. : 15/103619  
DATED : January 1, 2019  
INVENTOR(S) : David T. Chuang et al.

Page 1 of 1

It is certified that error appears in the above-identified patent and that said Letters Patent is hereby corrected as shown below:

In the Claims

In Claim 22, Column 143, Line 12, before "$Y_2$", insert --$Y_1$,--.

In Claim 23, Column 144, Line 46, before "$Y_2$", insert --$Y_1$,--.

In Claim 23, Column 144, Line 46, delete "$Y_8$", insert --$Y_5$-- therefor.

Signed and Sealed this
Fourteenth Day of May, 2019

Andrei Iancu
*Director of the United States Patent and Trademark Office*